(12) United States Patent
Ghoroghchian et al.

(10) Patent No.: US 11,730,826 B2
(45) Date of Patent: Aug. 22, 2023

(54) AMPHIPHILIC NANOPARTICLES FOR DELIVERY OF CRISPR BASED THERAPY

(71) Applicant: Massachusetts Institute of Technology, Cambridge, MA (US)

(72) Inventors: Paiman Peter Ghoroghchian, Boston, MA (US); Haihua Xiao, Cambridge, MA (US); Ruogu Qi, Houston, TX (US); Ting Li, Xi'an (CN)

(73) Assignee: Massachusetts Institute of Technology, Cambridge, MA (US)

( * ) Notice: Subject to any disclaimer, the term of this patent is extended or adjusted under 35 U.S.C. 154(b) by 1624 days.

(21) Appl. No.: 15/584,309

(22) Filed: May 2, 2017

(65) Prior Publication Data

US 2018/0078657 A1  Mar. 22, 2018

Related U.S. Application Data

(60) Provisional application No. 62/489,111, filed on Apr. 24, 2017, provisional application No. 62/330,684,
(Continued)

(51) Int. Cl.
*A61K 9/00* (2006.01)
*A61K 48/00* (2006.01)
(Continued)

(52) U.S. Cl.
CPC .......... *A61K 48/0041* (2013.01); *A61K 9/107* (2013.01); *A61K 31/282* (2013.01); *A61K 31/555* (2013.01); *A61K 33/243* (2019.01); *A61K 47/10* (2013.01); *A61K 47/34* (2013.01); *A61K 47/60* (2017.08); *A61K 47/646* (2017.08); *A61K 47/6907* (2017.08); *A61K 47/6935* (2017.08); *A61K 48/005* (2013.01); *C07K 2/00* (2013.01); *C08G 69/10* (2013.01);
(Continued)

(58) Field of Classification Search
CPC .................................................. A61K 48/0041
See application file for complete search history.

(56) References Cited

U.S. PATENT DOCUMENTS

| 4,534,881 A | 8/1985 | Sikes et al. |
| 5,877,158 A | 3/1999 | Bosslet et al. |
(Continued)

FOREIGN PATENT DOCUMENTS

| CN | 102525882 A | 7/2012 |
| CN | 102120036 B | 7/2013 |
(Continued)

OTHER PUBLICATIONS

Yin, Therapeutic genome editing by combined viral and non-viral delivery of CRISPR system components in vivo, Nat. Biotechnol., 2016, 34(3), 328-333 (Year: 2016).*
(Continued)

*Primary Examiner* — Paul W Dickinson
(74) *Attorney, Agent, or Firm* — Foley Hoag LLP; Alexander Akhiezer; Lawrence P. Tardibono

(57) ABSTRACT

Disclosed are copolymer micelles for simultaneous delivery of Cas9 mRNA and guide RNA for Cas9 CRISPR gene editing. Also disclosed are copolymer micelles for simultaneous delivery of a therapeutic or diagnostic nucleic acid and a cross-linking or alkylating anticancer agent.

28 Claims, 44 Drawing Sheets

Related U.S. Application Data filed on May 2, 2016, provisional application No. 62/330,697, filed on May 2, 2016.

(51) Int. Cl.

| | |
|---|---|
| A61K 47/60 | (2017.01) |
| A61K 47/64 | (2017.01) |
| C12N 15/113 | (2010.01) |
| A61K 33/243 | (2019.01) |
| A61K 47/69 | (2017.01) |
| A61K 31/555 | (2006.01) |
| C08G 81/00 | (2006.01) |
| C12N 15/11 | (2006.01) |
| A61K 9/107 | (2006.01) |
| A61K 31/282 | (2006.01) |
| A61K 47/34 | (2017.01) |
| C07K 2/00 | (2006.01) |
| C08G 69/10 | (2006.01) |
| C12N 15/90 | (2006.01) |
| A61K 47/10 | (2017.01) |
| A61K 39/00 | (2006.01) |
| C12N 15/09 | (2006.01) |
| G01N 21/47 | (2006.01) |

(52) U.S. Cl.
CPC .............. *C08G 81/00* (2013.01); *C12N 15/11* (2013.01); *C12N 15/113* (2013.01); *C12N 15/90* (2013.01); *A61K 2039/585* (2013.01); *C12N 15/09* (2013.01); *C12N 2310/20* (2017.05); *G01N 21/47* (2013.01)

(56) References Cited

U.S. PATENT DOCUMENTS

| | | |
|---|---|---|
| 6,815,167 B2 | 11/2004 | Crothers et al. |
| 6,977,153 B2 | 12/2005 | Kumar et al. |
| 8,575,330 B2 | 11/2013 | Tan |
| 8,647,604 B2 | 2/2014 | VanVeggel et al. |
| 9,161,993 B2 | 10/2015 | Jolck et al. |
| 9,227,917 B2 | 1/2016 | Anderson et al. |
| 9,241,898 B2 | 1/2016 | Saltzman et al. |
| 9,260,471 B2 | 2/2016 | Cancilla et al. |
| 9,295,685 B2 | 3/2016 | Gombotz et al. |
| 9,295,689 B2 | 3/2016 | de Fougerolles et al. |
| 9,472,694 B2 | 10/2016 | Dionne et al. |
| 9,555,132 B2 | 1/2017 | Vinogradov et al. |
| 10,751,423 B2 | 8/2020 | Ghoroghchian et al. |
| 2012/0009267 A1 | 1/2012 | Cho et al. |
| 2014/0308363 A1 | 10/2014 | Zale |
| 2017/0362609 A1 | 12/2017 | Ghoroghchian et al. |
| 2018/0008687 A1 | 1/2018 | Ghoroghchian et al. |
| 2018/0021453 A1 | 1/2018 | Bazzill et al. |
| 2018/0078657 A1 | 3/2018 | Ghoroghchian et al. |

FOREIGN PATENT DOCUMENTS

| | | |
|---|---|---|
| WO | WO-2007/008300 A2 | 1/2007 |
| WO | WO-2008/137733 A2 | 11/2008 |
| WO | WO-2011/110694 A2 | 9/2011 |
| WO | WO-2013/142969 A1 | 10/2013 |
| WO | WO-2014/066912 A1 | 5/2014 |
| WO | WO-2014/093343 A2 | 6/2014 |
| WO | WO-2014/145749 A1 | 9/2014 |
| WO | WO-2015/051349 A1 | 4/2015 |
| WO | WO-2015/069926 A1 | 5/2015 |
| WO | WO-2016/037165 A1 | 3/2016 |
| WO | WO-2017/192512 A2 | 11/2017 |
| WO | WO-2017/192544 A1 | 11/2017 |
| WO | WO-2017/192573 A1 | 11/2017 |

OTHER PUBLICATIONS

Qi, Biodegradable copolymers with identical cationic segments and their performance in siRNA delivery, Journal of Controlled Release, 2012, 152, 251-260 (Year: 2012).*

Cao et al., "A novel cationic triblock copolymer as noncovalent coating for the separation of proteins by CE," Electrophoresis, 32(20):2874-2883 (2011).

Cordeiro et al., "Novel cationic triblock copolymer of poly[2-(dimethylamino)ethyl methacrylate]-block-poly(β-amino ester)-block-poly[2-(dimethylamino)ethyl methacrylate]: a promising non-viral gene delivery system," Macromol Biosci, 15(2):215-228 (2015).

Gallon et al., "Triblock copolymer nanovesicles for pH-responsive targeted delivery and controlled release of siRNA to cancer cells," Biomacromolecules, 16(7):1924-1937 (2015).

Hinton et al., "Inhibition of influenza virus in vivo by siRNA delivered using ABA triblock copolymer synthesized by reversible addition-fragmentation chain-transfer polymerization," Nanomedicine, 9(8):1141-1154 (2014).

Jansson et al., "Small-angle X-ray scattering, light scattering, and NMR study of PEO-PPO-PEO triblock copolymer/cationic surfactant complexes in aqueous solution," J Phys Chem B, 109:7073-7083 (2005).

Jones et al., "Folate Receptor Targeted Delivery of siRNA and Paclitaxel to Ovarian Cancer Cells via Folate Conjugated Triblock Copolymer to Overcome TLR4 Driven Chemotherapy Resistance," Biomacromolecules, 17(1):76-87 (2016).

Kim et al., "siRNA delivery from triblock copolymer micelles with spatially-ordered compartments of PEG shell, siRNA-loaded intermediate layer, and hydrophobic core," Biomaterials, 35:4548-4556 (2014).

Mao et al., "A biodegradable amphiphilic and cationic triblock copolymer for the delivery of siRNA targeting the acid ceramidase gene for cancer therapy," Biomaterials, 32:3124-3133 (2011).

Qi et al., "Design and delivery of camplatin to overcome cisplatin drug resistance," J Mater Chem B, 3:176-179 (2015).

Qian et al., "Triblock copolymer-encapsulated nanoparticles with outstanding colloidal stability for siRNA delivery," ACS Appl Mater Interfaces, 5:2845-2852 (2013).

Segura et al., "Synthesis and in vitro characterization of an ABC triblock copolymer for siRNA delivery," Bioconjugate Chem, 18:736-745 (2007).

Song et al., "Multifunctional Pt(IV) pro-drug and its micellar platform: to kill two birds with one stone," J Mater Chem B, 1:762-772 (2013).

Xiao et al., "A dual-targeting hybrid platinum(IV) prodrug for enhancing efficacy ," Chem Commun, 48:10730-10732 (2012).

Yang et al., "Thermoresponsive behavior of cationic polyrotaxane composed of multiple pentaethylenehexamine-grafted alpha-cyclodextrins threaded on poly(propylene oxide)-poly(ethylene oxide)-poly(propylene oxide) triblock copolymer," J Phys Chemistry B, 113:682-690 (2009).

Yoncheva et al., "Cationic triblock copolymer micelles enhance antioxidant activity, intracellular uptake and cytotoxicity of curcumin," Int J Pharmaceut, 490:298-307 (2015).

Zhao et al., "Self-assembly nanomicelles based on cationic mPEG-PLA-b-Polyarginine(R15) triblock copolymer for siRNA delivery," Biomaterials, 33:6793-6807 (2012).

Final Office Action for U.S. Appl. No. 15/584,516, "Nanoparticle Conjugates of Highly Potent Toxins and Intraperitoneal Administration of Nanoparticle," dated Mar. 18, 2019.

Non-Final Office Action for U.S. Appl. No. 15/584,516, "Nanoparticle Conjugates of Highly Potent Toxins and Intraperitoneal Administration of Nanoparticle," dated Sep. 21, 2018.

Requirement for Restriction/Election for U.S. Appl. No. 15/584,516, "Nanoparticle Conjugates of Highly Potent Toxins and Intraperitoneal Administration of Nanoparticle," dated Mar. 8, 2018.

International Preliminary Report on Patentability for International Application No. PCT/US2017/030541 dated Nov. 6, 2018.

International Preliminary Report on Patentability for International Application No. PCT/US2017/030578 dated Nov. 6, 2018.

International Preliminary Report on Patentability for International Application No. PCT/US2017/030618 dated Nov. 6, 2018.

Blencowe et al., "Self-immolative linkers in polymeric delivery systems," Polym Chem, 2:773-790 (2011).

(56) References Cited

OTHER PUBLICATIONS

Creixell et al., "Co-delivery of siRNA and therapeutic agents using nanocarriers to overcome cancer resistance," Nano Today, 7(4):367-379 (2012).
Emoto et al., "Antitumor effect and pharmacokinetics of intraperitoneal NK105, a nanomicellar paclitaxel formulation for peritoneal dissemination," Cancer Sci, 103(7):1304-1310 (2012).
Gorris et al., "Surface modification and characterization of photon-upconverting nanoparticles for bioanalytical applications," Chem Soc Rev, 44(6): 1526-1560 (2015).
Huynh et al., "Acid degradable cross-linked micelles for the delivery of cisplatin: a comparison with nondegradable cross-linker," Chem Mater, 24(16):3197-3211 (2012).
International Search Report and Written Opinion for International Application No. PCT/US2017/030541 dated Nov. 8, 2017.
International Search Report and Written Opinion for International Application No. PCT/US2017/030578 dated Aug. 21, 2017.
International Search Report and Written Opinion for International Application No. PCT/US2017/030618 dated Oct. 17, 2017.
Juetten, "Self-immolative linkers for chemical amplification application," Graduate Theses and Dissertations, Iowa State University (2013).
Kren et al., "Nanocapsule-delivered Sleeping Beauty mediates therapeutic Factor VIII expression in liver sinusoidal endothelial cells of hemophilia A mice," J Clin Invest, 119(7):2086-2099 (2009).
Li et al., "Challenges in CRISPR/CAS9 delivery: Potential roles of nonviral vectors," Hum Gene Ther, 26(7): 452-462 (2015).
Liu et al., "A mPEG-PLGA-b-PLL copolymer carrier for adriamycin and siRNA delivery," Biomaterials, 33(17): 4403-4412 (2012).
Liu et al., "Nanoparticle tumor localization, disruption of autophagosomal trafficking, and prolonged drug delivery improve survival in peritoneal mesothelioma," Biomaterials, 102: 175-186 (2016).
Lu et al., "Paclitaxel nanoparticle inhibits growth of ovarian cancer xenografts and enhances lymphatic targeting," Cancer Chemother Pharmacol, 59(2):175-181 (2007).
Miyata et al., Polyplexes from poly(aspartamide) bearing 1,2-diaminoethane side chains induce pH-selective, endosomal membrane destabilization with amplified transfection and negligible cytotoxicity, J Am Chem Soc, 130(48): 16287-16294 (2008).
O'Reilly et al., "Cross-linked block copolymer micelles: functional nanostructures of great potential and versatility," Chem Soc Rev, 35(11): 1068-1083 (2006).
Osada et al., "Polymeric micelles from poly(ethylene glycol)-poly(amino acid) block copolymer for drug and gene delivery," J R Soc Interface, 6(Suppl 3):S325-S339 (2009).
Partial International Search Report for International Application No. PCT/US2017/030618, dated Aug. 16, 2017.

Qi et al., "Biodegradable copolymers with identical cationic segments and their performance in siRNA delivery," J Control Release, 159(2):251-260 (2012).
Riber et al., "Self-immolative linkers literally bridge disulfide chemistry and the realm of thiol-free drugs," Adv Healthc Mater, 4(12): 1887-1890 (2015).
Schumann et al., "Generation of knock-in primary human T cells using Cas9 ribonucleoproteins," Proc Natl Acad Sci USA, 112(33):10437-10442 (2015).
Shen et al., "Antiproliferative activity of polymer-bound, monoamine-coordinated platinum complexes against LNCaP human metastatic prostate adenocarcinoma cells," J Inorg Organomet Polym, 10(1): 51-60 (2000).
Shen et al., "Co-delivery of platinum drug and siNotch1 with micelleplex for enhanced hepatocellular carcinoma therapy," Biomaterials, 70:71-83 (2015).
Sheng, "Self-immolative chemistry: structural features and applications in designing smart materials," (2014).
Sun et al., "Self-assembled DNA nanoclews for the efficient delivery of CRISPR-Cas9 for genome editing," Angew Chem Int Ed Engl, 54(41):12029-12033 (2015).
Thevenaz et al., "Luminescent Nanoparticles with Lanthanide-Containing Poly(ethylene glycol-Polycaprolactone) Block Copolymers," Biomacromolecules, 15(11): 3994-4001 (2014).
Weninger et al., "Combinatorial optimization of CRISPR/Cas9 expression enables precision genome engineering in the methylotrophic yeast *Pichia pastoris*," J Biotechnol, 235:139-149 (2016).
Xiao et al., "Biodegradable polymer—cisplatin (IV) conjugate as a pro-drug of cisplatin (II)," Biomaterials, 32(30):7732-7739 (2011).
Xu et al., "Co-delivery of doxorubicin and P-glycoprotein siRNA by multifunctional triblock copolymers for enhanced anticancer efficacy in breast cancer cells," J Mater Chem B, 3(10):2215-2228 (2015).
Xu et al., "Enhancing tumor cell response to chemotherapy through nanoparticle-mediated codelivery of siRNA and cisplatin prodrug," Proc Natl Acad Sci U S A, 110(46): 18638-18643 (2013).
Yin et al., "Therapeutic genome editing by combined viral and non-viral delivery of CRISPR system components in vivo," Nat Biotechnol, 34(3):328-333 (2016).
Zheng et al., "Polypeptide cationic micelles mediated co-delivery of docetaxel and siRNA for synergistic tumor therapy," Biomaterials, 34(13):3431-3438 (2013).
Zhu et al., "Co-delivery of siRNA and paclitaxel into cancer cells by biodegradable cationic micelles based on PDMAEMA-PCL-PDMAEMA triblock copolymers," Biomaterials, 31(8):2408-2416 (2010).
Zuris et al., "Efficient Delivery of Genome-Editing Proteins In Vitro and In Vivo," Nat Biotechnol, 33(1): 73-80 (2015).
Qi et al., "Synthesis of biodegradable cationic triblock copolymer mPEG-PCL-PLL for siRNA delivery," J Controlled Release, 152:e133-e91 (Abstract) (2011).
U.S. Appl. No. 15/584,516, Pending.
U.S Appl. No. 15/584,496, Pending.

* cited by examiner

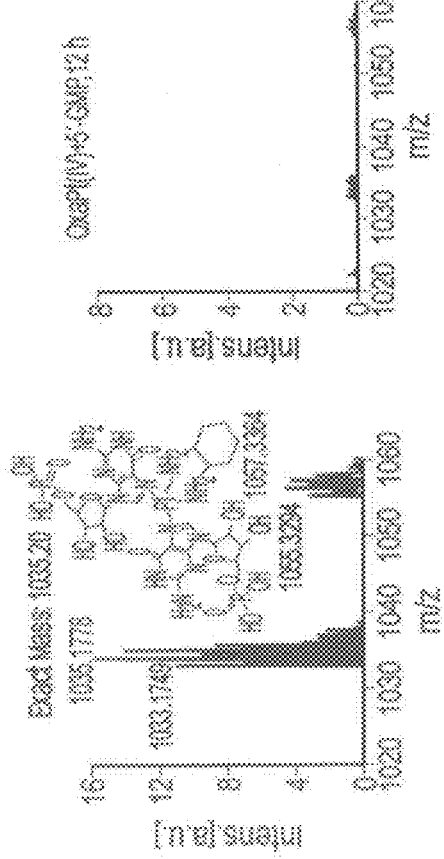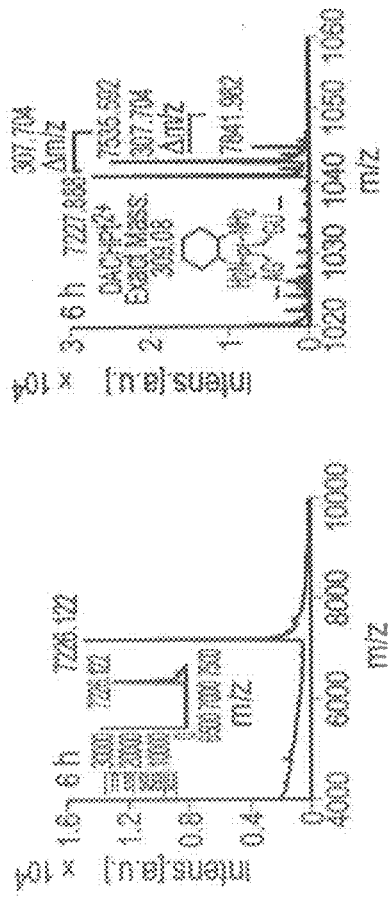

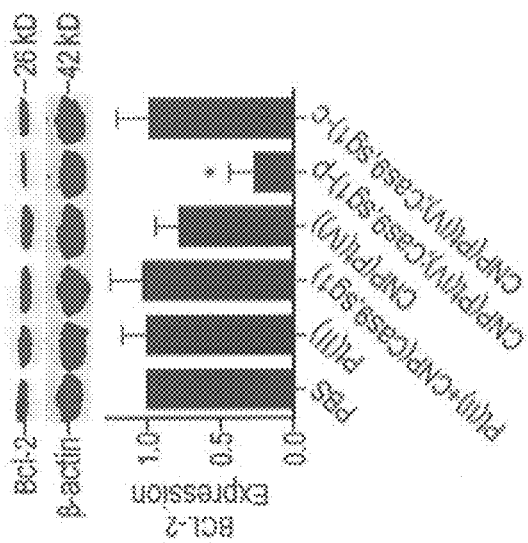
FIG. 33H
FIG. 33I
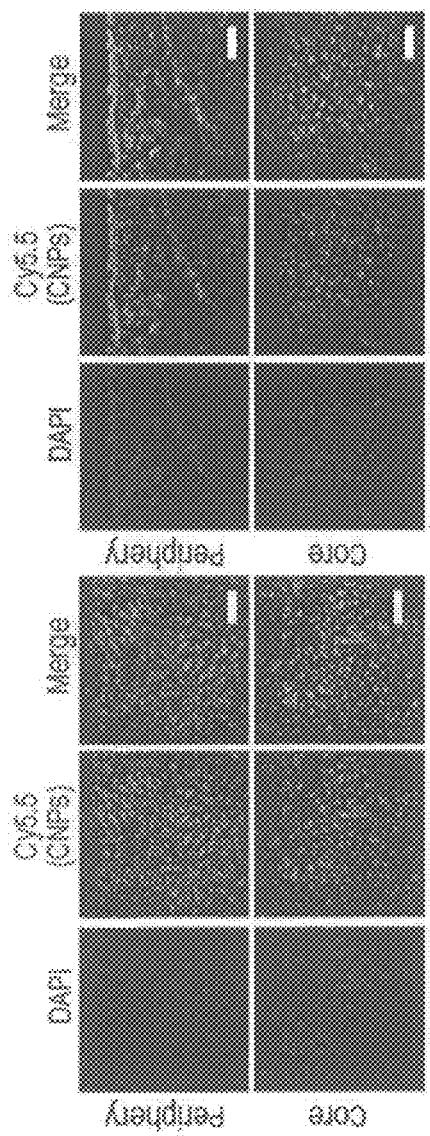
FIG. 33F
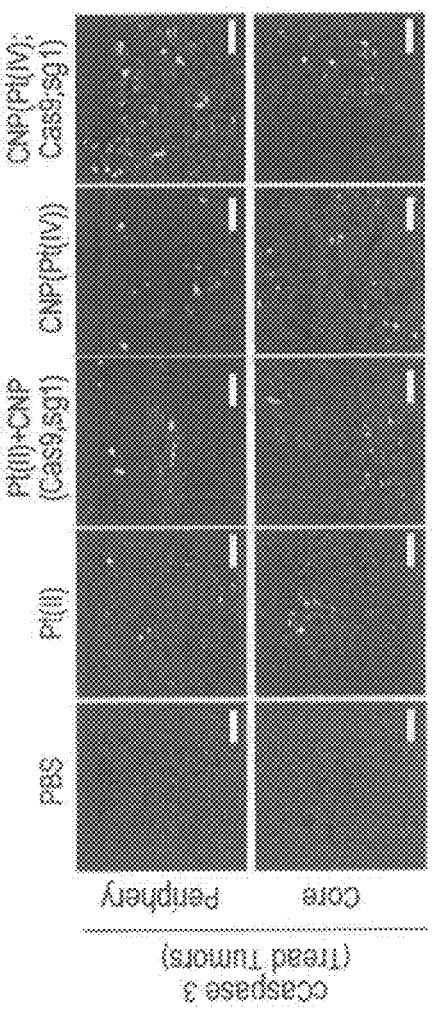
FIG. 33G

Figure 34

| RNA | Code | Sequence |
|---|---|---|
| SMAD4[1] sgRNA | SMAD4 | 5'-ACAACTCGTTCGTAGTGATAGUUUUAGAGCUAGAAAUAGCAAGUUAAAAUAAG<br><br>GCUAGUCCGUUAUCAACUUGAAAAAGUGGCACCGAGUCGGUGCUUUUUU-3' |
| Seed region of SMAD4 sgRNA[1] | s-SMAD4 | 5'-ACA ACU CGU UCG UAG UGA UA-3' |
| Cas9 mRNA[2] | Cas9 | N.A. |
| Cy5.5-labeled Cas9 mRNA[3] | Cy5.5-Cas9 | N.A. |
| Cy5-labeled EGFP mRNA[4] | Cy5 - EGFP | N.A. |
| BCL-2 sgRNA[1] | sg1 | 5'-GTCGCAGAGGGGCTACGAGTGUUUUAGAGCUAGAAAUAGCAAGUUAAAAUAAG<br><br>GCUAGUCCGUUAUCAACUUGAAAAAGUGGCACCGAGUCGGUGCUUUUUU-3' |
| | sg2 | 5'-CCATTATAAGCTGTCGCAGAGUUUUAGAGCUAGAAAUAGCAAGUUAAAAUAAG<br><br>GCUUCAACUUGAAAAAGUGGCACCGAGUCGGUGCUUUUUU-3' |
| | sg3 | 5'-CATTATAAGCTGTCGCAGAGGUUUUAGAGCUAGAAAUAGCAAGUUAAAAUAAG<br><br>GCUAGUCCGUUAUCAACUUGAAAAAGUGGCACCGAGUCGGUGCUUUUUU-3' |

1: Invitrogen; custom synthesis.
2: Trilink Biotechnologies, USA; Lot number: L-6125
3: Cas9 mRNA obtained from Trilink (Lot number L-6125), labeled with Cy5.5 using EDC/NHS chemistry, and purified by column washing
4: Trilink Biotechnologies, USA; Lot number: L-6402

Figure 35

| Name | Description |
|---|---|
| NP | Nanoparticles of mPEG-b-PZLL-b-PASP(DET) |
| NP(Pt(IV)) | NPs conjugated to Pt(IV) |
| NP(Cas9,SMAD4) | NPs complexed with Cas9 mRNA and SMAD4 sgRNA |
| NP(Cas9,sg1) | NPs complexed with Cas9 mRNA and BCL-2 sgRNA (sequence 1) |
| NP(Cas9,sg2) | NPs complexed with Cas9 mRNA and BCL-2 sgRNA (sequence 2) |
| NP(Cas9,sg3) | NPs complexed with Cas9 mRNA and BCL-2 sgRNA (sequence 3) |
| NP(Cas9,NC sgRNA) | NPs complexed with Cas9 mRNA and NC sgRNA (negative control) |
| NP(Pt(IV));Cas9,sg1) | NPs containing Pt(IV), Cas9 mRNA and BCL-2 sgRNA (sequence 1) |
| NP(Pt(IV));Cas9,sg3) | NPs containing Pt(IV), Cas9 mRNA and BCL-2 sgRNA (sequence 3) |
| NP(Pt(IV));Cas9,NC sgRNA) | NPs containing Pt(IV), Cas9 mRNA, and NC sgRNA (negative control) |
| NP(Pt(IV);Cy5 EGFP,sgRNA) | NPs containing Pt(IV), Cy5-labeled EGFP mRNA and BCL-2 sgRNA (sequence 1) |
| NP(FITC,Pt(IV));Cy5 EGFP,sgRNA) | NPs containing Pt(IV), Cy5-labeled EGFP mRNA and BCL-2 sgRNA (sequence 1) in which the core NP is labeled with FITC. |
| CNP(Pt(IV)) | mPEG-b-PGA coated NPs conjugated to Pt(IV) |
| CNP(Cas9,sg1) | mPEG-b-PGA coated NPs complexed with Cas9 mRNA and BCL-2 sgRNA (sequence 1) |
| CNP(Pt(IV));Cas9,sg1) | mPEG-b-PGA coated NPs containing Pt(IV), Cas9 mRNA, and BCL-2 sgRNA (sequence 1) |
| CNP(Pt(IV),iFluor™ 405,5-FAM;Cy5.5 Cas9,sgRNA) | mPEG-b-PGA coated NPs containing Pt(IV), Cy5.5-labeled Cas9 mRNA, and BCL-2 sgRNA (sequence 1) in which the core NP is labeled with iFluor™ 405 and the shell polymer is conjugated to 5-FAM. |
| CNP(Pt(IV),Cy7.5;Cy5-EGFP,sgRNA) | mPEG-b-PGA coated NPs containing Pt(IV), Cy5-labeled EGFP mRNA, and BCL-2 sgRNA (sequence 1) in which the core NP is further conjugated to Cy7.5 |
| CNP(Pt(IV),Cy7.5,Cy5.5,Cas9,sgRNA) | mPEG-b-PGA coated NPs containing Pt(IV), Cas9 mRNA, and BCL-2 sgRNA (sequence 1) in which the core NP is labeled with Cy5.5 and the shell polymer is conjugated to Cy7.5 |

AMPHIPHILIC NANOPARTICLES FOR DELIVERY OF CRISPR BASED THERAPY

RELATED APPLICATIONS

This application claims the benefit of priority to U.S. Patent Application Ser. No. 62/330,684, filed May 2, 2016, U.S. Patent Application Ser. No. 62/330,697, filed May 2, 2016, and U.S. Patent Application Ser. No. 62/489,111, filed Apr. 24, 2017, the contents of each of which are hereby incorporated by reference.

BACKGROUND

Co-Delivery of Anticancer Agents and siRNA

Since the late 1970's, platinum(II)-containing small molecules, including cisplatin, carboplatin and oxaliplatin, have become the most common class of agents used for cancer therapy worldwide. While initial clinical response rates to platinum-containing regimens are high, the durations of activity in patients with metastatic tumors are generally short. The various mechanisms by which these cancers develop "platinum resistance," and the specific DNA mutations that enable evasion of cellular checkpoint and DNA repair pathways, are areas of very active investigation. To that end, RNAi approaches have been extensively employed to elucidate cellular responses and to identify novel therapeutic targets for combination treatments. The fidelity of these results is implicitly reliant on the assumption that the RNAi transcript remains active, even for a few hours, when utilized in combination with platinum therapies.

Platinum(II)-containing small molecules interact with oligonucleotides of DNA, forming DNA intra- and inter-strand crosslinks through the generation of Pt-DNA adducts with the $N_7$ positions of both guanine (G) and/or adenine (A) bases; the most common crosslinks that are formed included (GpG) (i.e. the 1, 2-guanine-guanine intra-strand cross link) and d(GpA) (i.e. the 1, 2-guanine-adenine intra-strand cross link), which account for 47-50% and 23-28% of adducts, respectively. With increasing quantities of intracellular Pt-DNA adducts, cell cycle arrest and eventual apoptosis ensue. Given the base homology between RNA and DNA, recent investigations have sought to determine the presence, as well as to ascertain the biological consequences, of Pt-RNA adducts that may be similarly generated.

Cytoplasmic RNA is the major binding pool for platinum (II)-containing small molecules, and the concentrations of Pt-RNA adducts that are formed are 5-6 times that of Pt-DNA adducts upon intracellular uptake of cisplatin. Platinum(II)-containing agents readily form bidentate GG, GA/AG, and GXG (X≠G) adducts with siRNA and miRNA. While platination of neither the sense strand nor the seed portions of the antisense strand seem to abrogate silencing activity, Pt-RNA adducts that are formed in non-seed regions of the antisense strand induce thermal destabilization of the duplex of siRNA (or miRNA). This leads to decreased silencing of its complementary target mRNA. The results of these investigations raise important questions as to whether the concentrations of Pt-RNA adducts that are formed during short incubation times are sufficient to influence in vitro cell culture experiments that employ combinations of RNAi and platinum-based chemotherapies. RNAi transcript inactivation through Pt-RNA adduct formation could have implications for the results of numerous preclinical studies that have utilized such approaches for either discovery or therapeutic intervention.

Thus, there is an unmet need for compositions and delivery methods for combining RNAi and platinum therapies in order to prevent premature siRNA inactivation and to maximize the synergistic activity of these reactive species.

Delivery of Cas9 CRISPR Components

With the development of new and affordable methods for whole-genome sequencing, and the design and implementation of large genome annotation projects, scientists are poised to deliver upon the promises of the genomic revolution to transform basic science and personalized medicine. The resulting wealth of information presents researchers with a new primary challenge of converting this enormous amount of data into functionally and clinically relevant knowledge. Central to this problem is the need for efficient and reliable methods that enable investigators to determine how genotype influences phenotype. Targeted gene inactivation via homologous recombination is a powerful method capable of providing conclusive information for evaluating gene function. However, the use of this technique has been hampered by several factors, including the low efficiency at which engineered constructs are correctly inserted into the chromosomal target site, the need for time-consuming and labor-insensitive selection/screening strategies, and the potential for adverse mutagenic effects. Targeted gene knockdown by RNAi has provided researchers with a rapid, inexpensive, and high-throughput alternative to homologous recombination. However, knockdown by RNAi is incomplete, varies between experiments and laboratories, has unpredictable off-target effects, and provides only temporary inhibition of gene function. These restrictions impede researchers' ability to link directly phenotype to genotype and limit the practical application of RNAi technology.

In the past decade, a new approach has emerged that enables investigators to manipulate virtually any gene in a diverse range of cell types and organisms. This core technology—commonly referred to as 'genome editing'—is based on the use of engineered nucleases composed of sequence-specific DNA-binding domains fused to a nonspecific DNA cleavage module. These chimeric nucleases enable efficient and precise genetic modifications by inducing targeted DNA double-strand breaks (DSBs) that stimulate the cellular DNA repair mechanisms, including error-prone nonhomologous end joining (NHEJ) and homology-directed repair (HDR). The versatility of this approach is facilitated by the programmability of the DNA-binding domains that are derived from zinc-finger and transcription activator-like effector (TALE) proteins. This combination of simplicity and flexibility has catapulted zinc-finger nucleases (ZFNs), transcription activator-like effector nucleases (TALENs), and clustered regulatory interspaced short palindromic repeats CRISPR/Cas (CRISPR-associated)-based RNA-guided DNA endonucleases to the forefront of genetic engineering.

The CRISPR/Cas system has recently emerged as a potentially facile and efficient alternative to ZFNs and TALENs for inducing targeted genetic alterations. In bacteria, the CRISPR system provides acquired immunity against invading foreign DNA via RNA-guided DNA cleavage. In the type II CRISPR/Cas system, short segments of foreign DNA, termed 'spacers' are integrated within the CRISPR genomic loci and transcribed and processed into short CRISPR RNA (crRNA). These crRNAs anneal to transactivating crRNAs (tracrRNAs) and direct sequence-specific cleavage and silencing of pathogenic DNA by Cas proteins. Recent work has shown that target recognition by the Cas9 protein requires a 'seed' sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. Significantly, the CRISPR/Cas system has been shown to be directly portable to human cells by co-delivery of plasmids expressing the Cas9 endonuclease and the necessary crRNA components. These programmable RNA-guided DNA endonucleases have demonstrated multiplexed gene disruption capabilities and targeted integration in iPS cells. Cas9 endonucleases have also been converted into nickases, enabling an additional level of control over the mechanism of DNA repair.

However, questions remain regarding the optimal methods for delivering these nucleases into cells and organisms. In particular, although adenoviral vectors can accommodate and deliver full-length TALEN genes into human cells, lentiviral plasmid vectors harboring TALEN sequences are prone to rearrangements after transduction. Furthermore, the large size of TALENs may limit their delivery by size-restricted vectors such as recombinant adeno-associated virus (AAV), which has been shown to accommodate ZFN genes.

Thus, there is an unmet need for compositions and delivery methods for CRISPR/Cas, ZFN, and TALEN gene editing tools to maximize transduction and improve delivery efficiency.

SUMMARY

In certain embodiments, the invention relates to a composition comprising, consisting essentially of, or consisting of:
   an agent, wherein the agent is (a) a nuclease selected from the group consisting of Cas9, TALEN, and zinc finger, or (b) a nucleic acid encoding a nuclease selected from the group consisting of Cas9, TALEN, and zinc finger;
   an optional pharmaceutically acceptable carrier;
   an optional DNA editing template; and
   a block copolymer comprising:
   (i) a first block comprising a plurality of first monomers, wherein each first monomer is hydrophilic;
   (ii) a second block comprising a plurality of second monomers, wherein each second monomer is hydrophobic; and
   (iii) a third block comprising a plurality of third monomers, wherein each third monomer is positively charged at a pH from about 6.8 to about 7.4,
      wherein
      the agent is non-covalently associated with the block copolymer; and
      the DNA editing template, when present, is non-covalently associated with the block copolymer.

In certain embodiments, the invention relates to a composition comprising:
   an optional pharmaceutically acceptable carrier;
   a Cas9 mRNA;
   a guide RNA; and
   a block copolymer comprising:
   (i) a first block comprising a plurality of first monomers, wherein each first monomer is hydrophilic;
   (ii) a second block comprising a plurality of second monomers, wherein each second monomer is hydrophobic; and
   (iii) a third block comprising a plurality of third monomers, wherein each third monomer is positively charged at a pH from about 6.8 to about 7.4,
      wherein
      the Cas9 mRNA is non-covalently associated with the block copolymer; and
      the guide RNA is non-covalently associated with the block copolymer.

In certain embodiments, the invention relates to a block polymer having the structure:

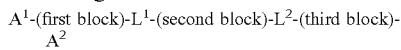

wherein
   the first block comprises a plurality of first monomers; each first monomer is selected from the group consisting of ethylene glycol, propylene glycol, and vinyl alcohol;
   the second block comprises a plurality of second monomers; each second monomer is side-chain N-protected lysine;
   the third block comprises a plurality of third monomers; each third monomer is selected from the group consisting of arginine, lysine, side-chain aminoalkyl-functionalized asparagine, and side-chain aminoalkyl-functionalized aspartamide;
   $A^1$ is OH or —O—$(C_1$-$C_6)$alkyl;
   $A^2$ is H, an amine protecting group, or an amino acid;
   $L^1$ is a covalent bond or a first linker; and
   $L^2$ is a covalent bond or a second linker.

In certain embodiments, the invention relates to a composition comprising:
   a pharmaceutically acceptable carrier;
   a first block copolymer comprising:
   (i) a first block comprising a plurality of first monomers, wherein each first monomer is hydrophilic;
   (ii) a second block comprising a plurality of second monomers, wherein each second monomer is hydrophobic; and
   (iii) a third block comprising a plurality of third monomers, wherein each third monomer is positively charged at a pH from about 6.8 to about 7.4; and
   a second block copolymer comprising:
   (i) a fourth block comprising a plurality of fourth monomers, wherein each fourth monomer has a pKa less than or equal to about 6 in water; and
   (ii) a fifth block comprising a plurality of first monomers, wherein the second block copolymer is non-covalently associated with the first block copolymer.

In certain embodiments, the invention relates to a composition comprising:
   an optional pharmaceutically acceptable carrier;
   an siRNA;
   an anticancer agent; and
   a block copolymer comprising:
   (i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
   (ii) a second block comprising a plurality of second monomers, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate; and (iii) a third block comprising a plurality of third monomers, wherein each third monomer is selected from the group consisting of lysine, side-chain aminoalkyl-functionalized lysine, asparagine, side-chain aminoalkyl-functionalized asparagine, arginine, aspartamide, side-chain aminoalkyl-functionalized aspartamide, and ethyleneimine, wherein the siRNA is non-covalently associated with the block copolymer; and the anticancer agent is associated with the block copolymer.

In certain embodiments, the invention relates to a method of treating cancer comprising administering to a subject in need thereof a therapeutically effective amount of any one of the compositions described herein.

BRIEF DESCRIPTION OF THE FIGURES

FIG. 4A is a representative ESI-MS spectrum (intensity (a.u.) vs. m/z) of solutions of 10 mM 5'-GMP at 12 h after incubation with 5 mM OxaPt(II) at 37° C. The presence of the DACHPt(5'-GMP)$_2$ adduct was monitored over time by measuring changes in the relative height of the peak at m/z=1035.1778; the structure and molecular weight of any bis-adducts are shown in the inset. Note: other peaks in the ESI spectra correspond to adducts formed with Na+ and K+.

FIG. 4B is a representative ESI-MS spectrum (intensity (a.u.) vs. m/z) of solutions of 10 mM 5'-GMP at 12 h after incubation with 5 mM OxaPt(IV) at 37° C. The presence of the DACHPt(5'-GMP)$_2$ adduct was monitored over time by measuring changes in the relative height of the peak at m/z=1035.1778; the structure and molecular weight of any bis-adducts are shown in the inset. Note: other peaks in the ESI spectra correspond to adducts formed with Na+ and K+.

FIG. 4C is a plot of % platinum binding to 5'-GMP as a function of time. These data show the kinetics of DACHPt (5'-GMP)$_2$ adduct formation, depicted as the molar percentage of the total 5'-GMP pool in solution, as determined by $^1$HNMR.

FIG. 4D is a representative MALDI-TOF-MS spectrum (intensity (a.u.) vs. m/z) of the products formed after 6 h of incubation of (50 μM) BCL-2 siRNA with 500 uM OxaPt(II) at 37° C. Three major peaks are attributed to unmodified BCL-2 siRNA (m/z=7227.8888), BCL-2 siRNA with one DACHPt$^{2+}$ adduct (m/z=7535.592), and BCL-2 siRNA with two DACHPt$^{2+}$ adducts (m/z=7841.982). Note, the molecular weight of DACHPt is 309.08 and the Δm/z upon formation of the siRNA-DACHPt$^{2+}$ mono adduct is 307.704; RNA loses two H$^+$ to keep it at +1 charge state.

FIG. 4E is a representative MALDI-TOF-MS spectrum (intensity (a.u.) vs. m/z) of the products formed after 6 h of incubation of (50 μM) BCL-2 siRNA with 500 uM OxaPt (IV) at 37° C. Three major peaks are attributed to unmodified BCL-2 siRNA (m/z=7227.8888), BCL-2 siRNA with one DACHPt$^{2+}$ adduct (m/z=7535.592), and BCL-2 siRNA with two DACHPt$^{2+}$ adducts (m/z=7841.982). Note, the molecular weight of DACHPt is 309.08 and the Δm/z upon formation of the siRNA-DACHPt$^{2+}$ mono adduct is 307.704; RNA loses two H$^+$ to keep it at +1 charge state. Unmodified BCL-siRNA displays a mass peak at m/z=7226.12 (inset).

FIG. 4F is a plot of RNA binding (ng Pt/μg RNA) as a function of time. These data show the binding kinetics of OxaPt(II) and OxaPt(IV) to double-stranded BCL-2 siRNA as measured by AAS. Data are expressed as "ng Pt atoms per μg RNA".

Signals generated from the untreated (blank) cells are included for reference. Data shown are expressed as mean values±standard deviation of the mean (n=3 experimental replicates per condition).

Figures 13A, 13B:
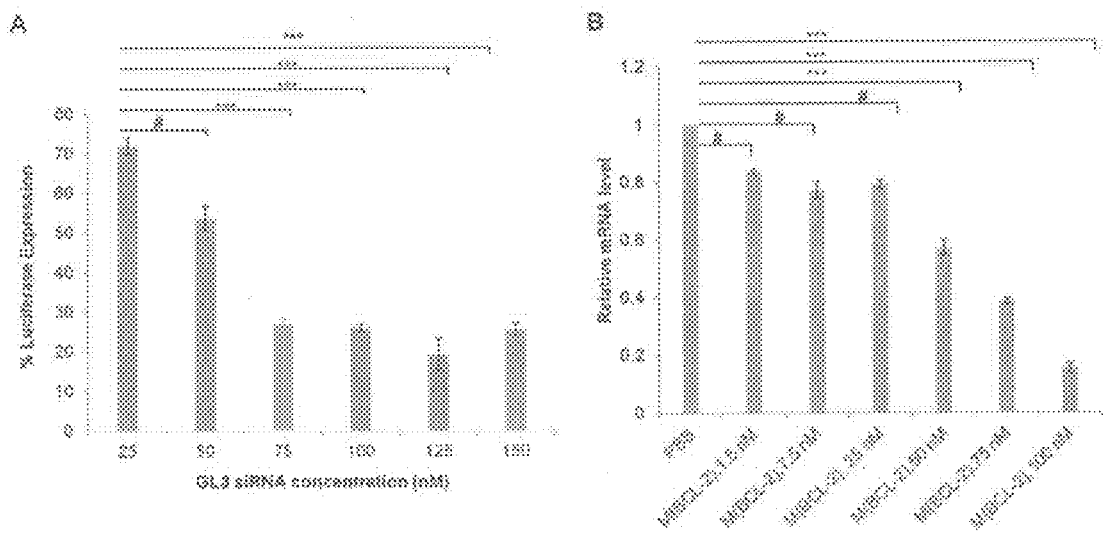

FIG. 13A is a bar graph showing the relative expression of luciferase in LUC$^+$ MCF-7 in MCF-7 breast cancer cells treated with different concentrations of anti-luciferase GL3 siRNA. Note, the siRNA was transfected using polymeric micelles comprised of mPEG-b-PCL-b-PLL formed at a fixed N/P ratio=8:1 anionic siRNA to cationic polymer. Significance is defined as p<0.01 and *p<0.001. Note, # denotes p>0.05.

FIG. 13B is a bar graph showing the relative BCL-2 mRNA levels in MCF-7 breast cancer cells treated with different concentrations of BCL-2 siRNA. Note, the siRNA was transfected using polymeric micelles comprised of mPEG-b-PCL-b-PLL formed at a fixed N/P ratio=8:1 anionic siRNA to cationic polymer. Significance is defined as p<0.01 and *p<0.001. Note, # denotes p>0.05.

Figure 14A:
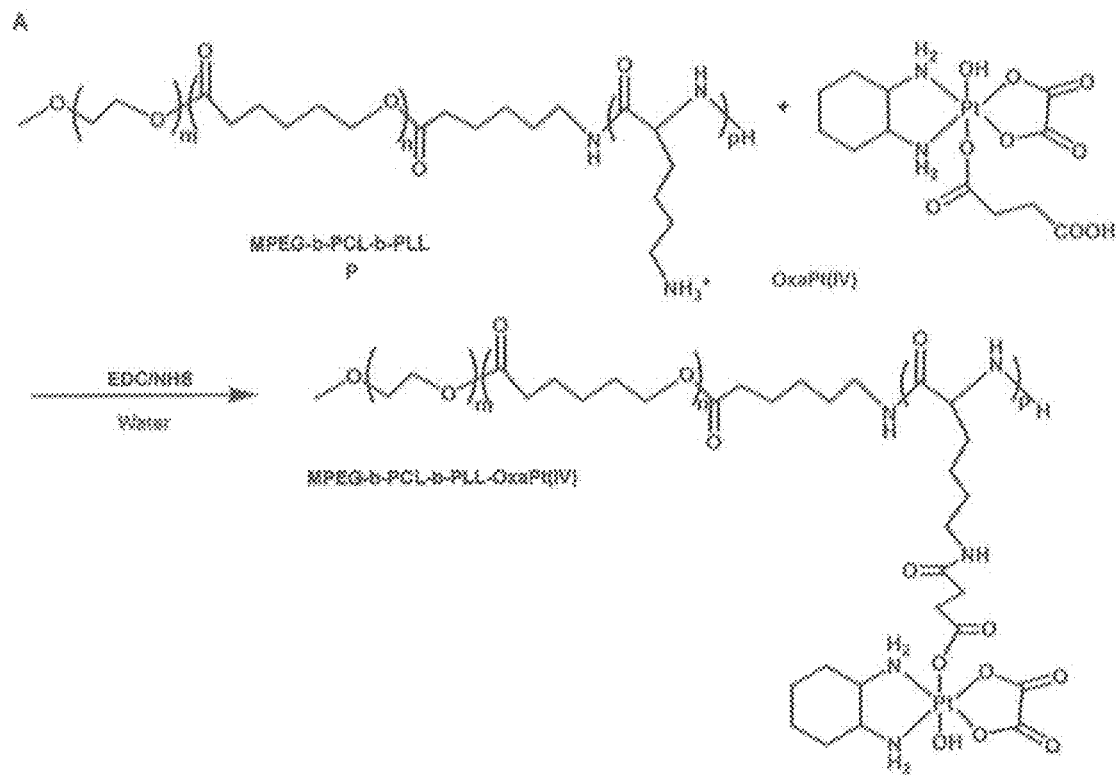

FIG. 14A is a schematic representation of a synthesis of mPEG-b-PCL-b-PLL-OxaPt(IV).

Figure 14B:
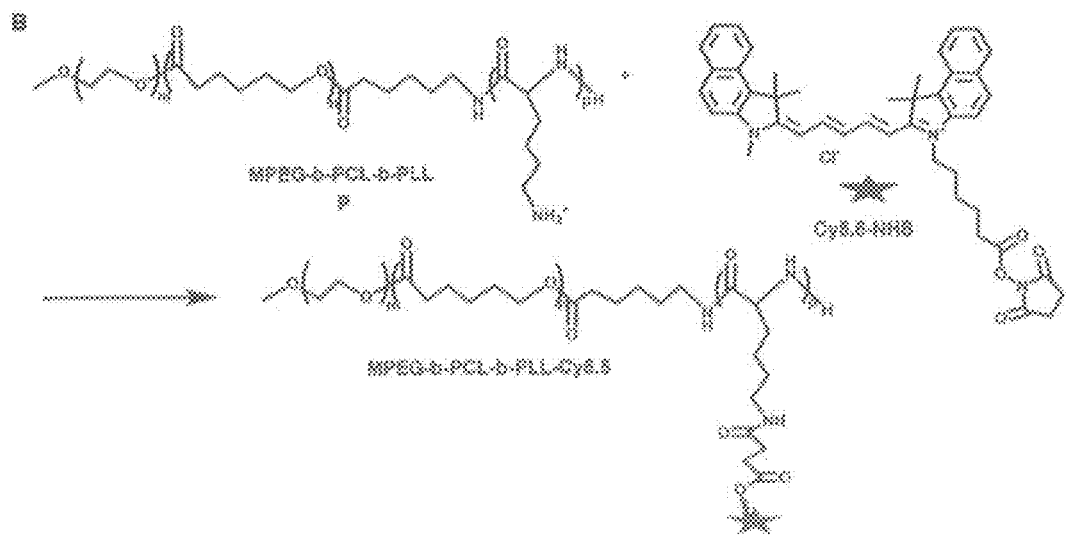

FIG. 14B is a schematic representation of conjugation of the polymer from FIG. 14A to Cy5.5.

Figure 15:
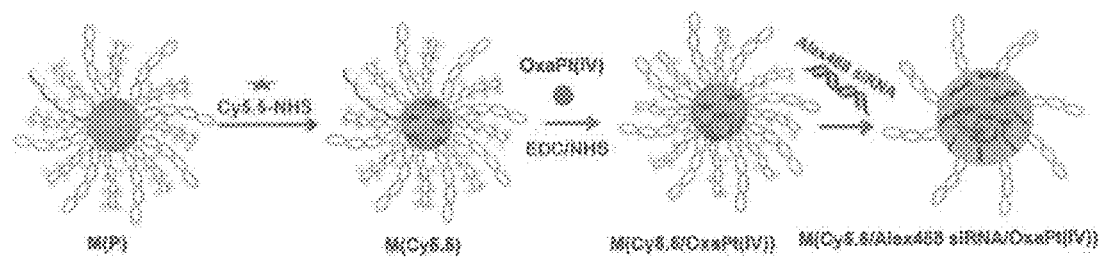

FIG. 15 is a schematic representation of a preparation of Cy5.5-conjugated polymeric micelles that contain OxaPt (IV) and Alex-488 labeled siRNA. Cy5.5-NHS (Lumiprobe, FL, USA) was conjugated to mPEG-b-PCL-b-PLL, yielding fluorescently labeled micelles in solution (i.e. M(Cy5.5)). Blending of the same polymer with mPEG-b-PCL-b-PLL-OxaPt(IV) generates dual-labeled micelles (i.e. M(Cy5.5/OxaPt(IV)). Further complexation with Alexa-488 labeled siRNA yields M(Cy5.5/Alexa488 siRNA/OxaPt(IV)), which enables independent monitoring of each species within the micelle (e.g. polymer and siRNA by fluorescence and platinum by GFAAS/ICP-MS).

Figures 16A, 16B, 16C:
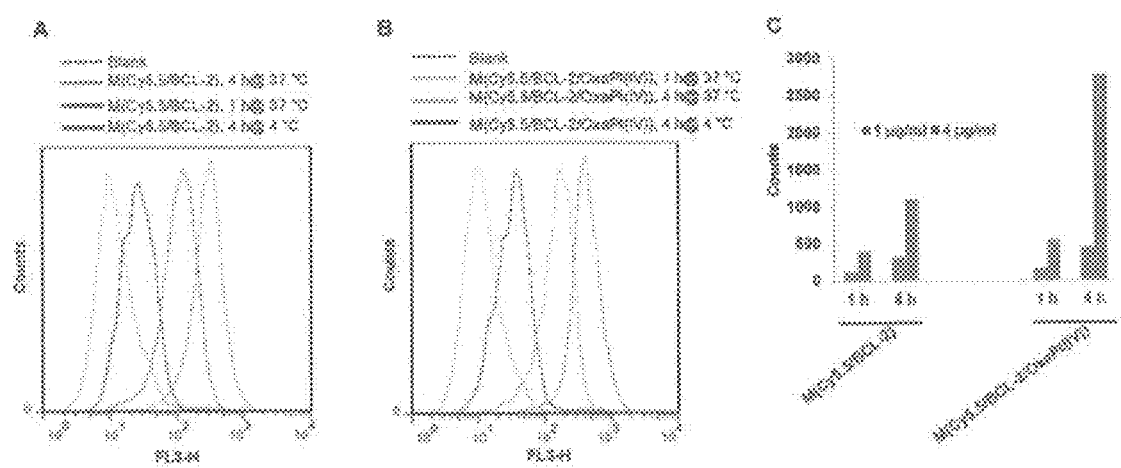

FIG. 16A is a plot of the intracellular uptake of BCL-2 siRNA-containing micelles by OVCAR4 ovarian cancer cells, as determined by flow cytometry for Cy5.5-labeled polymer. OVCAR4 cells were seeded in 6-well plates at a density of $4 \times 10^5$ cells/well. After attachment overnight, the cells were then treated with M(Cy5.5/BCL-2) at 1 µg or 4 µg Cy5.5/mL. The cells were incubated with each micellar formulation for 1 or 4 h and at either 37 or 4° C. prior to flow measurements of labeled populations.

FIG. 16B is a plot of the intracellular uptake of BCL-2 siRNA-containing micelles by OVCAR4 ovarian cancer cells, as determined by flow cytometry for Cy5.5-labeled polymer. OVCAR4 cells were seeded in 6-well plates at a density of $4 \times 10^5$ cells/well. After attachment overnight, the cells were then treated with M(Cy5.5/BCL-2/OxaPt(IV)) at 1 µg or 4 µg Cy5.5/mL. The cells were incubated with each micellar formulation for 1 or 4 h and at either 37 or 4° C. prior to flow measurements of labeled populations.

FIG. 16C is a bar graph showing the peak fluorescence intensities of Cy5.5 within OVCAR4 cells at various time points after incubation with the different micellar formulations from FIG. 16A and FIG. 16B.

Figures 17A, 17B, 17C:
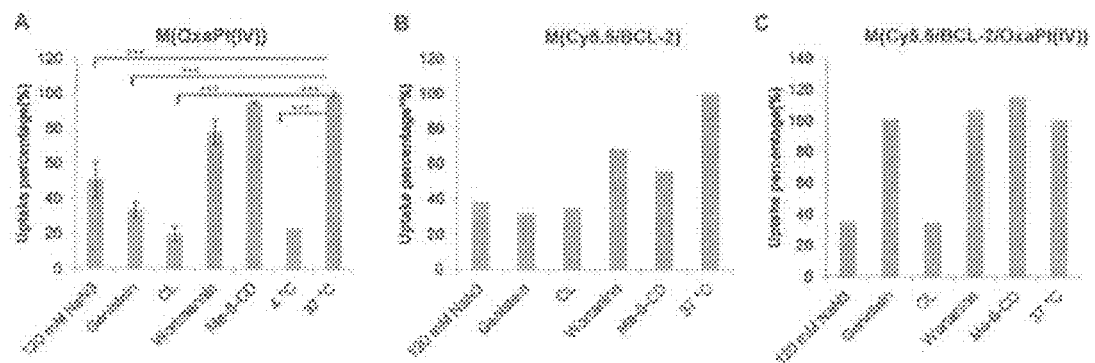

FIG. 17A is a bar graph showing the % cellular uptake for various polymeric micelles. MCF-7 cells were seeded in 6-well plates at a density of $1 \times 10^6$ cells/well. After attachment overnight, the cells were then treated with media containing different small molecule inhibitors of specific endocytosis pathways, including NaN$_3$ (120 mM), genistein (200 µg/mL), chlorpromazine (CL) (20 µg/mL), wortmannin (0.2 µM), or methyl-1-cyclodextrin (Me-β-CD) (200 µM). Note, CL was utilized as an inhibitor of clathrin-dependent (CDE) endocytosis; Me-β-CD and genistein were used as inhibitors of clathrin-independent (CIE) endocytosis; and, wortmannin is a known inhibitor of macropinocytosis. Control cells were similarly plated with fresh media and incubated at either 4 (positive control) or 37° C. (negative control). 1 h after media exchange, cells were treated with M(OxaPt(IV)) at a fixed Pt (10 µM) and Cy5.5 concentrations (1 µg/mL). After 4 h, all cells were washed with (×5) PBS and lysed with HNO$_3$/H$_2$O$_2$; the concentrations of internalized micelles were determined by either ICP-MS (for quantification of Pt) or by flow cytometry (for quantification of Cy5.5-conjugated polymer) and data were normalized to the average values for the negative control. Data are presented as mean values±the standard deviations of the mean for n=3 technical replicates per condition. Significance is denoted by ***p.<0.001.

FIG. 17B is a bar graph showing the % cellular uptake for various polymeric micelles. MCF-7 cells were seeded in 6-well plates at a density of $1 \times 10^6$ cells/well. After attachment overnight, the cells were then treated with media containing different small molecule inhibitors of specific endocytosis pathways, including NaN$_3$ (120 mM), genistein (200 µg/mL), chlorpromazine (CL) (20 µg/mL), wortmannin (0.2 µM), or methyl-β-cyclodextrin (Me-β-CD) (200 µM). Note, CL was utilized as an inhibitor of clathrin-dependent (CDE) endocytosis; Me-β-CD and genistein were used as inhibitors of clathrin-independent (CIE) endocytosis; and, wortmannin is a known inhibitor of macropinocytosis. Control cells were similarly plated with fresh media and incubated at either 4 (positive control) or 37° C. (negative control). 1 h after media exchange, cells were treated with M(Cy5.5/BCL-2) at a fixed Pt (10 µM) and Cy5.5 concentrations (1 µg/mL). After 4 h, all cells were washed with (×5) PBS and lysed with HNO$_3$/H$_2$O$_2$; the concentrations of internalized micelles were determined by either ICP-MS (for quantification of Pt) or by flow cytometry (for quantification of Cy5.5-conjugated polymer) and data were normalized to the average values for the negative control. Data are presented as mean values±the standard deviations of the mean for n=3 technical replicates per condition. Significance is denoted by ***p.<0.001.

FIG. 17C is a bar graph showing the % cellular uptake for various polymeric micelles. MCF-7 cells were seeded in 6-well plates at a density of $1 \times 10^6$ cells/well. After attachment overnight, the cells were then treated with media containing different small molecule inhibitors of specific endocytosis pathways, including NaN$_3$ (120 mM), genistein (200 µg/mL), chlorpromazine (CL) (20 µg/mL), wortmannin (0.2 µM), or methyl-β-cyclodextrin (Me-β-CD) (200 µM). Note, CL was utilized as an inhibitor of clathrin-dependent (CDE) endocytosis; Me-β-CD and genistein were used as inhibitors of clathrin-independent (CIE) endocytosis; and, wortmannin is a known inhibitor of macropinocytosis. Control cells were similarly plated with fresh media and incubated at either 4 (positive control) or 37° C. (negative control). 1 h after media exchange, cells were treated with M(Cy5.5/BCL-2/OxaPt(IV)) at a fixed Pt (10 µM) and Cy5.5 concentrations (1 µg/mL). After 4 h, all cells were washed with (×5) PBS and lysed with HNO$_3$/H$_2$O$_2$; the concentrations of internalized micelles were determined by either ICP-MS (for quantification of Pt) or by flow cytometry (for quantification of Cy5.5-conjugated polymer) and data were normalized to the average values for the negative control. Data are presented as mean values±the standard deviations of the mean for n=3 technical replicates per condition. Significance is denoted by ***p.<0.001.

Figure 18:
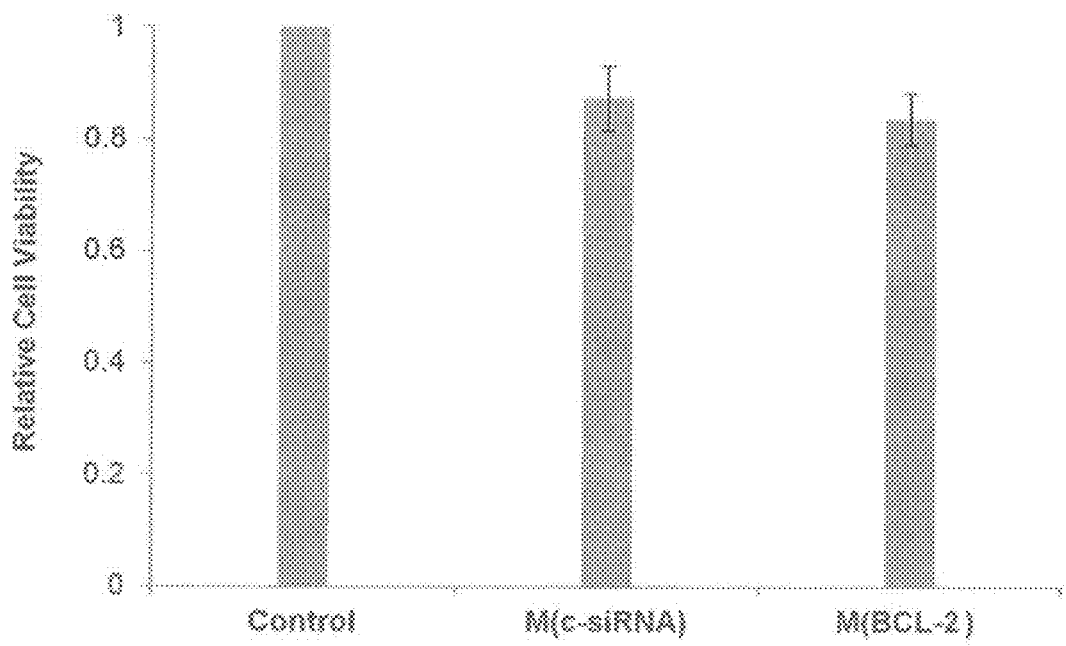

FIG. 18 is a bar graph showing relative cell viability of MCF-7 cells treated with various siRNA-containing polymeric micelles. mPEG-b-PCL-b-PLL micelles containing either control siRNA (M(c-siRNA)) or BCL-2 siRNA (M(BCL-2)) were formed at an N/P ratio of 8:1 anionic siRNA to cationic polymer. The treatment concentration of each siRNA species was 100 nM. Fresh media served as a control treatment. Data are presented as mean values±standard deviation of the mean for an n=4 technical replicates per condition.

Figures 19A, 19B, 19C, 19D, 19E, 19F:
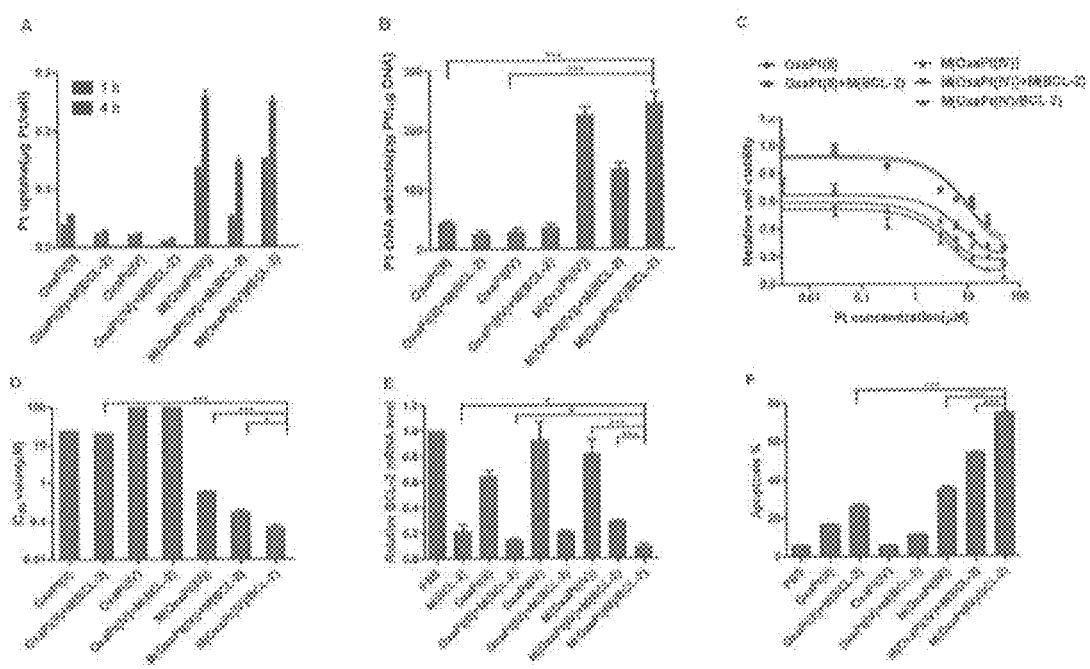

FIG. 19A is a bar graph showing platinum uptake (µg Pt/cell) for various compositions. These data show that co-encapsulation of OxaPt(IV) and BCL-2 siRNA within a single micellar transfection reagent (i.e. M(oxaPt(IV)/BCL-2) quantitatively maximizes the intracellular uptake of oxaliplatin, the numbers of Pt-DNA adducts that are formed, the suppression of BCL-2 mRNA, and cytotoxicity to MCF-7 cells through augmentation of cellular apoptosis. Oxaliplatin uptake into MCF-7 cells after 1 h and 4 h of cellular exposure to various treatments. The platinum concentration was 10 LM and 100 nmol of siRNA was used in each experimental group. Cells were lyzed after treatment and the determination of intracelluar platinum content was conducted by ICP-MS. Experiments were performed in triplicate. Data are displayed as the mean value±standard deviation of the mean. $IC_{50}$ values were derived from three independent experiments each with four technical replicates per condition.

FIG. 19B is a bar graph showing the total number of Pt-DNA adducts (pg Pt/µg DNA) as assessed after 24 h of incubation with each treatment group, as defined in the description of FIG. 19A. DNA was isolated after cellular lysis and the content of DNA-bound Pt was determined by ICP-MS. Experiments were performed in triplicate. Data are displayed as the mean value±standard deviation of the mean. $IC_{50}$ values were derived from three independent experiments each with four technical replicates per condition. Only mean values are displayed. In all cases, significance is defined as $*p<0.05$, $p<0.01$, and $*p<0.001$.

FIG. 19C is a plot of relative cell viability (as determined by the MTT cell viability assay, which was performed 48 h after incubation with each treatment group as defined in the description of FIG. 19A) as a function of platinum concentration (µM). Experiments were performed in triplicate. Data are displayed as the mean value±standard deviation of the mean. $IC_{50}$ values were derived from three independent experiments each with four technical replicates per condition. Only mean values are displayed. In all cases, significance is defined as $*p<0.05$, $p<0.01$, and $*p<0.001$.

FIG. 19D is a bar graph showing $IC_{50}$ values (µM) for cellular toxicity as determined by the MTT cell viability assay, which was performed 48 h after incubation with each treatment group as defined in the description of FIG. 19A. Only mean values are displayed. In all cases, significance is defined as $*p<0.05$, $p<0.01$, and $*p<0.001$.

FIG. 19E is a bar graph showing relative BCL-2 mRNA levels, as determined by qRT-PCR conducted 48 h after treatment with each experimental combination as defined in the description of FIG. 19A. Experiments were performed in triplicate. Data are displayed as the mean value±standard deviation of the mean. $IC_{50}$ values were derived from three independent experiments each with four technical replicates per condition.

FIG. 19F is the a bar graph showing total percentage of MCF-7 cells that underwent apoptosis as determine by flow cytometry after 36 h of treatment with various conditions. Equivalent platinum (10 uM) and siRNA concentration (100 nM) were used for each condition as defined in the description of FIG. 19A. 48 h after incubation, the fraction of MCF-7 cells undergoing apoptosis was detected by flow cytometry using the Annexin V-FITC Apoptosis Detection Kit I (BD Biosciences, San Jose, Calif.) and analyzed using WinMDI 2.9 software. Only mean values are displayed. In all cases, significance is defined as $*p<0.05$, $p<0.01$, and $*p<0.001$.

Figure 20:
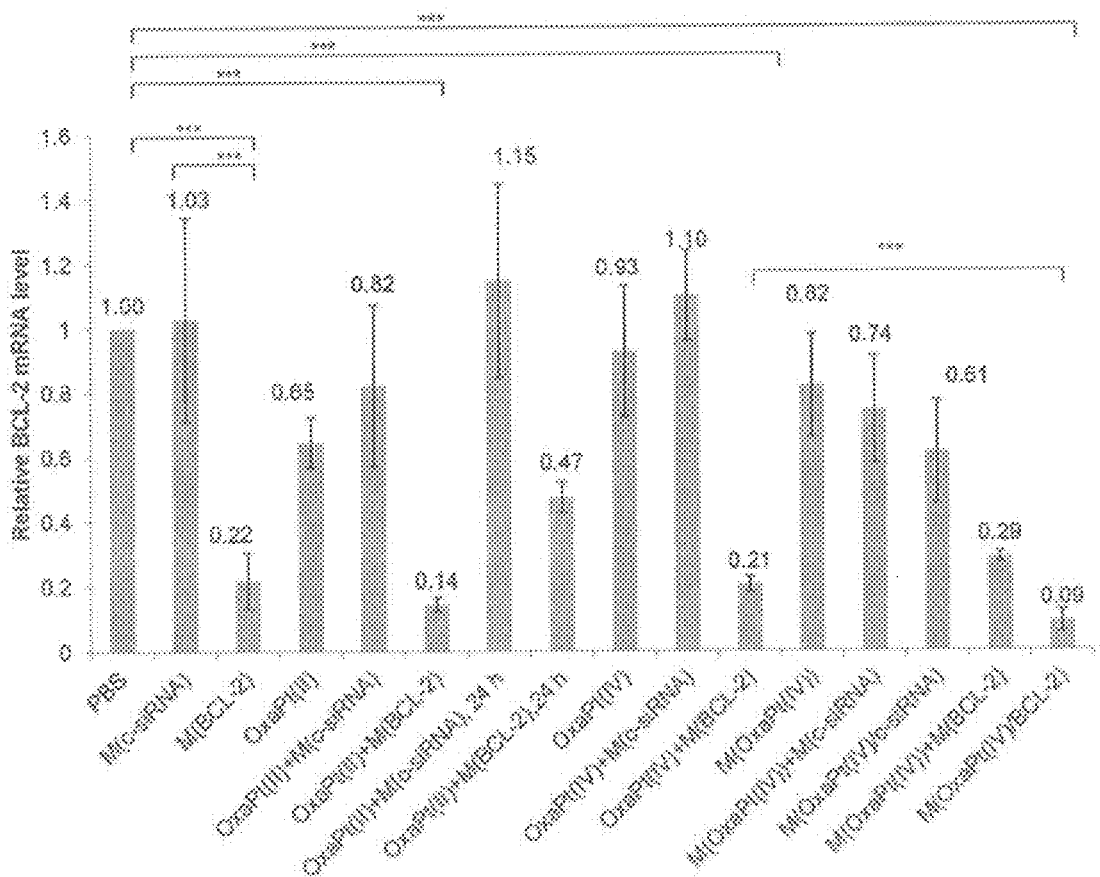

FIG. 20 is a bar graph showing relative BCL-2 mRNA levels after 48 h of treatment with various compositions. These data indicate the effectiveness of different strategies for combining Pt and BCL-2 siRNA to induce maximal BCL-2 RNAi. Various Pt species were administered to cells in 6-well plates at equal Pt concentrations (10 µM); 100 nM of either control (c-siRNA) or BCL-2 siRNA were added in each siRNA containing treatment. Two additional groups were compared in which OxaPt(II) was preincubated with either M(BCL-2) or M(c-siRNA) for 24 h at 37° C. prior to cellular addition. Cells were incubated with all treatment groups for 48 h and were then subject to RNA extraction followed by RT-qPCR to determine relative BCL-2 mRNA levels. Data are displayed as mean values±the standard deviation of the mean (n=3 replicates per condition). Significance is defined as $***p<0.001$.

Figures 21A, 21B, 21C:
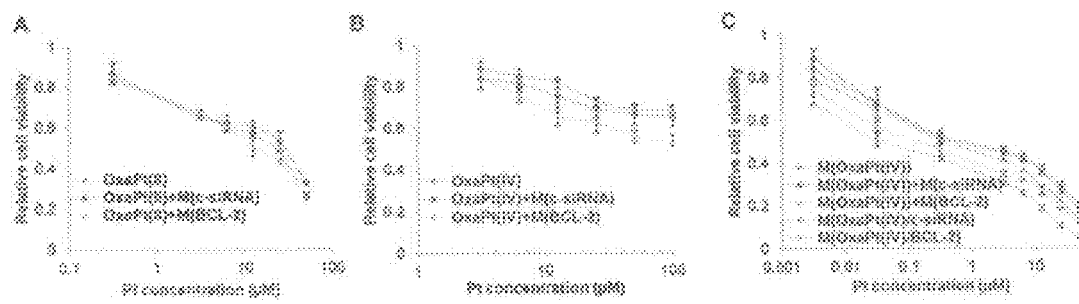

FIG. 21A is a plot of the relative in vitro viability of MCF-7 cells as a function of platinum concentration (µM). Cells were incubated with OxaPt(II) containing treatments, with and without micellar-complexed control (i.e. M(c-siRNA)) or BCL-2 siRNA (i.e. M(BCL-2)) for 72 h. Viability was measured using the MTT colorimetric assay.

FIG. 21B is a plot of the relative in vitro viability of MCF-7 cells as a function of platinum concentration (µM). Cells were incubated with OxaPt(IV) containing treatments, with and without micellar-complexed control (i.e. M(c-siRNA)) or BCL-2 siRNA (i.e. M(BCL-2)) for 72 h. Viability was measured using the MTT colorimetric assay.

FIG. 21C is a plot of the relative in vitro viability of MCF-7 cells as a function of platinum concentration (µM). Cells were incubated with M(OxaPt(IV)) containing treatments, with and without micellar-complexed control (i.e. M(c-siRNA)) or BCL-2 siRNA (i.e. M(BCL-2)) for 72 h. Viability was measured using the MTT colorimetric assay.

Figure 22A:
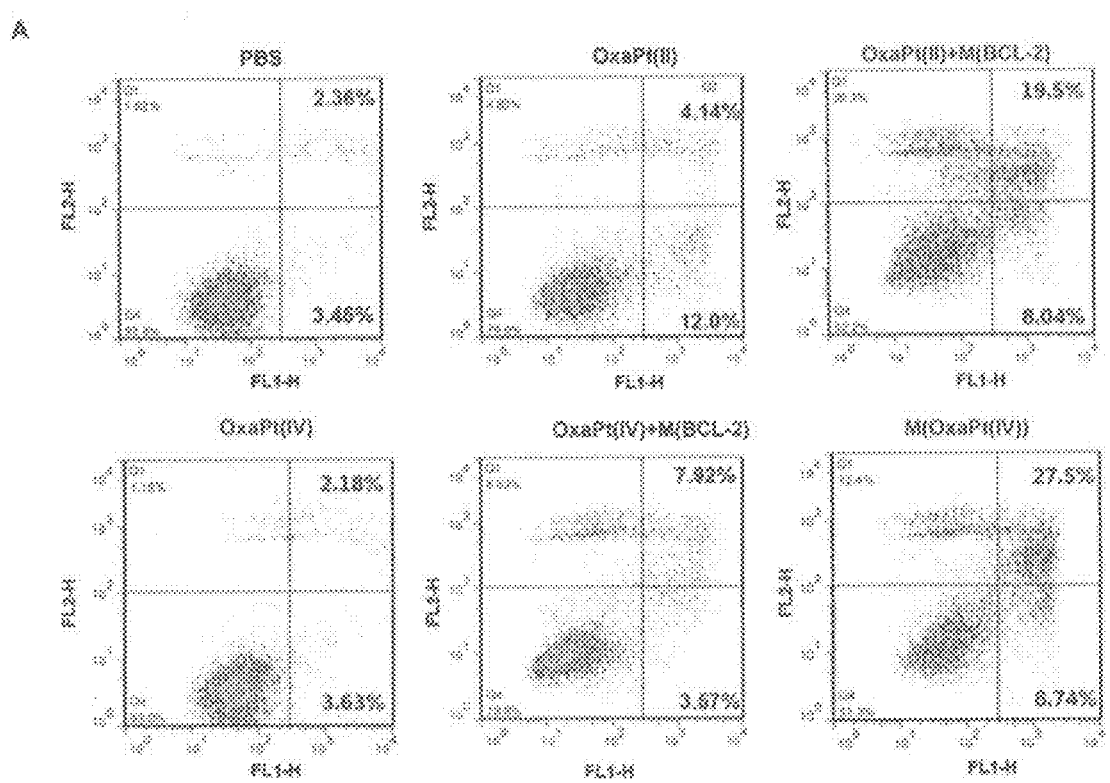

FIG. 22A is a series of plots showing the results of flow cytometry histograms (FL2-H vs. FL1-H). These data are a comparison of the effectiveness of different strategies for combining oxaliplatin species and BCL-2 siRNA to induce maximal cellular apoptosis. Oxaliplatin species were administered to MCF-7 cells in 6-well plates at equal Pt concentrations (10 µM); 100 nM of either micellar-complex c-siRNA or BCL-2 siRNA were added in each siRNA containing treatment. Apart from the various OxaPt(II) and OxaPt(IV) containing groups, as well as the single siRNA groups (i.e. M(c-siRNA) and M(BCL-2)), two additional groups were included in which OxaPt(II) was preincubated with either M(BCL-2) or M(c-siRNA) for 24 h at 37° C. prior to cellular addition. Cells were incubated with all treatment groups for 48 h and the cellular fractions undergoing apoptosis were detected by flow cytometry using the Annexin V-FITC Apoptosis Detection Kit I; the results were analyzed using WinMDI 2.9 software. Flow cytometry histograms of cells treated with different combinations of oxaliplatin species and/or BCL-2 siRNA; early apoptotic events are captured in the upper right panel of each graph while late events are found in the lower right panel.

Figure 22B:
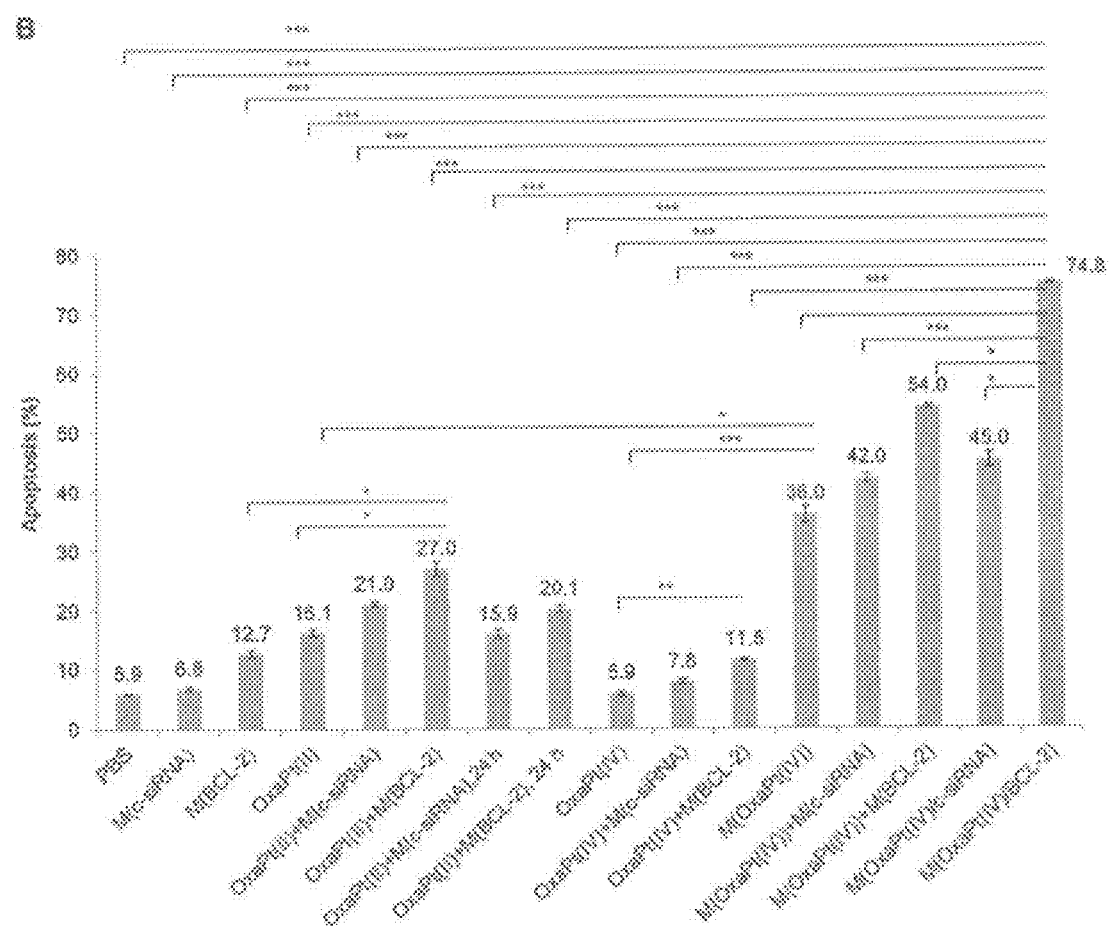

FIG. 22B is a bar graph of the total percentages of MCF-7 cells undergoing apoptosis after 48 h of treatment with each experimental group as defined in the description of FIG. 22A. Data are displayed as mean values±the standard deviation of the mean (n=3 technical replicates). Significance is defined as *p<0.05, p<0.01, *p<0.001.

Figure 23A:
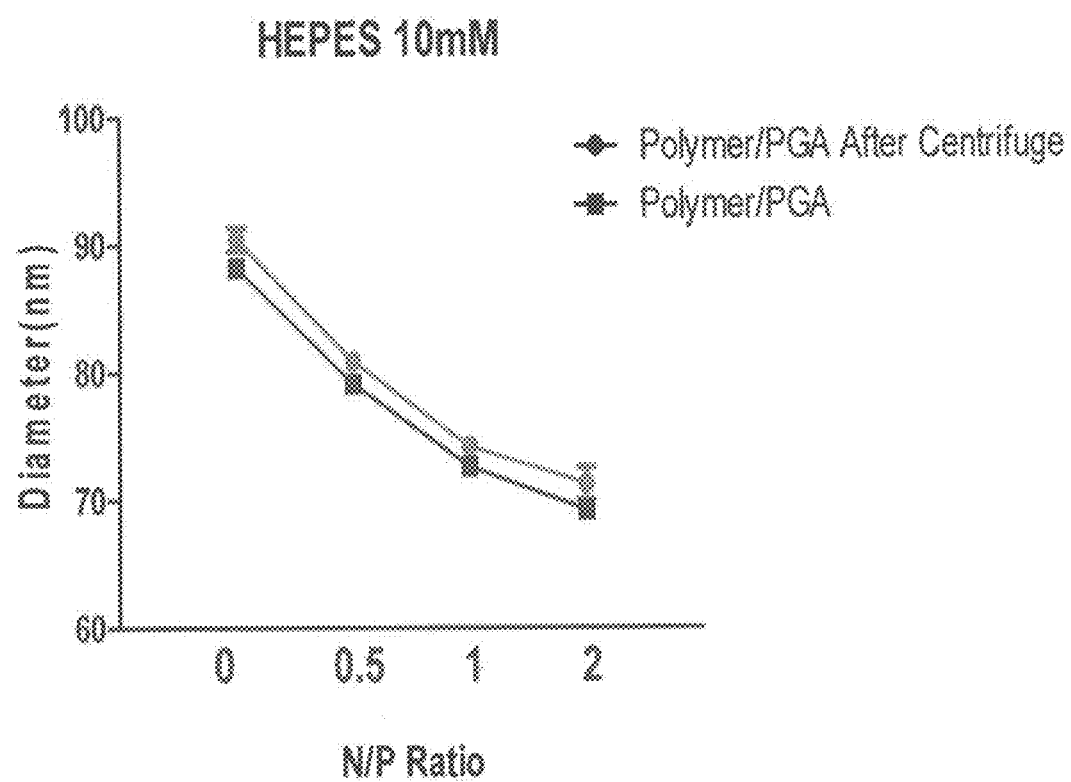

FIG. 23A is a plot of coated micelle diameter (nm) as a function of N/P ratio. Coating cationically charged PEO-b-PBzLL-PASP (i.e. "polymer") based micelles with anionically charged PEG-PGA in 10 mM HEPES (pH 7.4) with different ratios of negatively charged PEO-b-PGA ("N") to positively charged PEO-b-PBzLL-PASP ("P") affects the particle diameter.

Figure 23B:
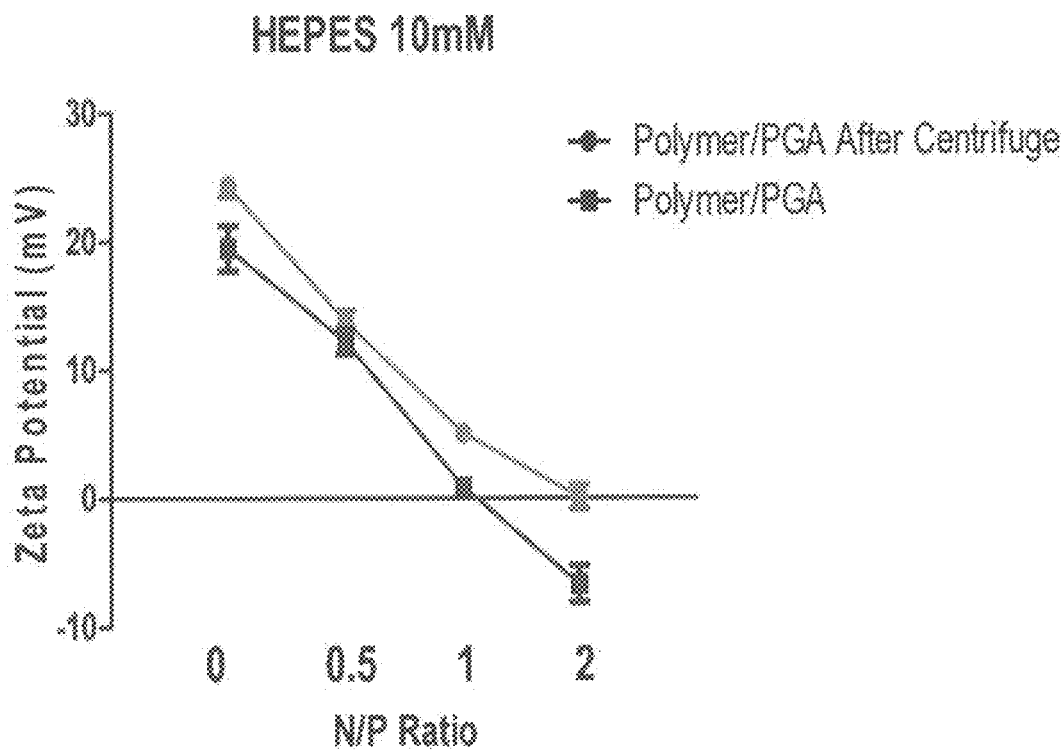

FIG. 23B is a plot of zeta potential (mV) as a function of N/P ratio. Coating cationically charged PEO-b-PBzLL-PASP (i.e. "polymer") based micelles with anionically charged PEG-PGA in 10 mM HEPES (pH 7.4) with different ratios of negatively charged PEO-b-PGA ("N") to positively charged PEO-b-PBzLL-PASP ("P") affects the overall charge (zeta potential) in solution.

Figure 24A:
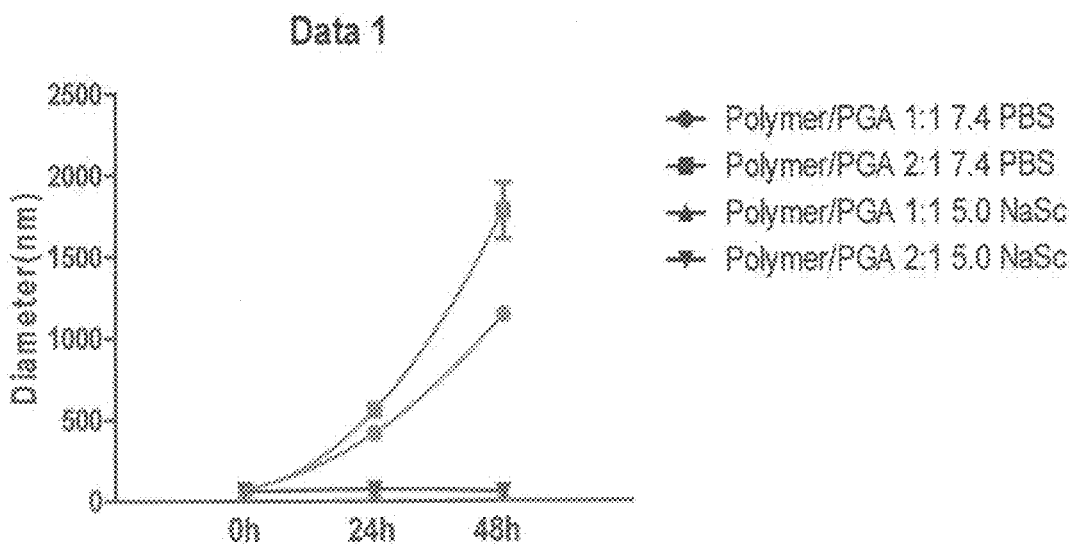

FIG. 24A is a plot of coated micelle diameter (nm) as a function of time in different buffer solutions.

Figure 24B:
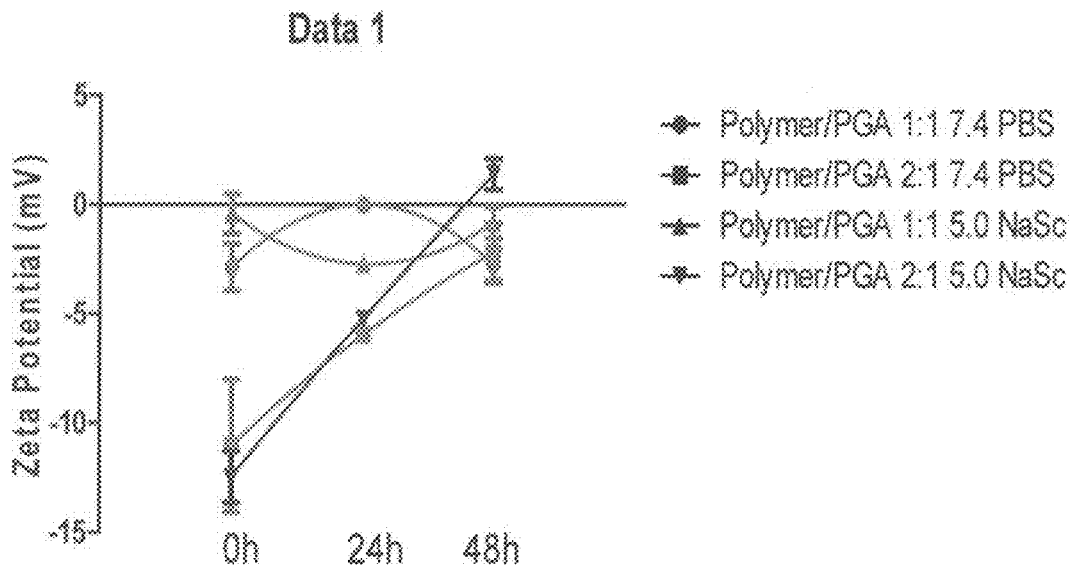

FIG. 24B is a plot of zeta potential (mV) as a function of time for coated micelles in different buffer solutions.

Figure 25A:
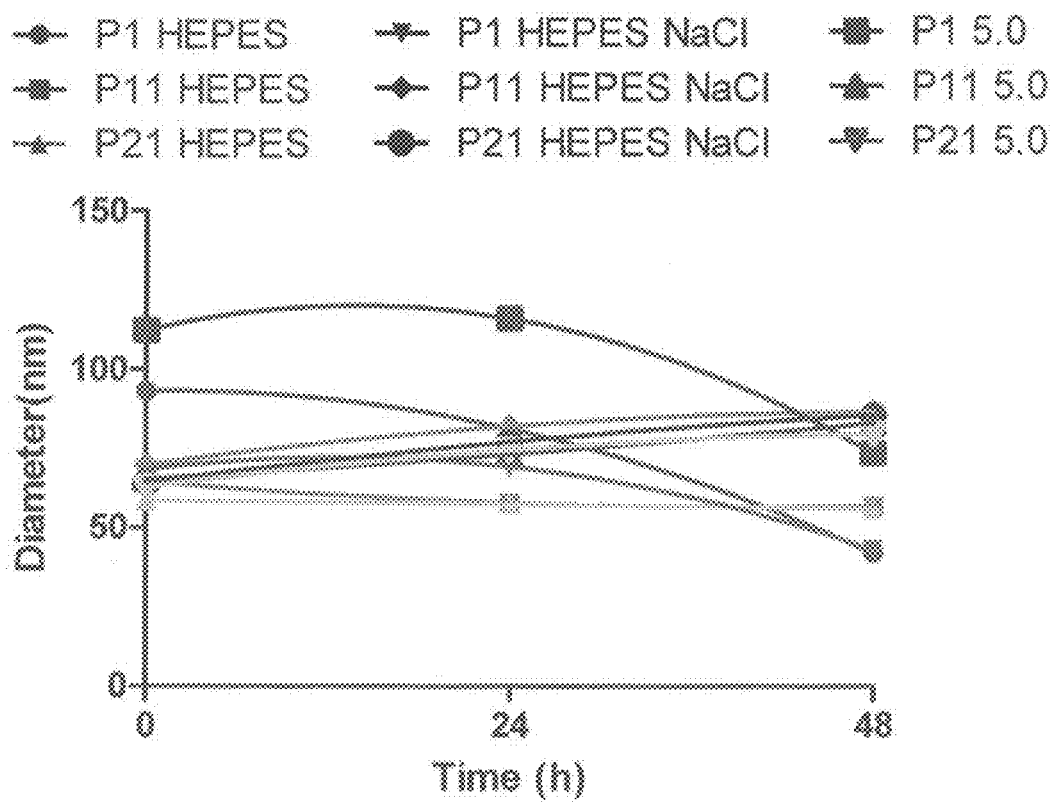

FIG. 25A is a plot of coated micelle diameter (nm) as a function of time in different buffer solutions after centrifugation to remove excess PEO-b-PGA.

Figure 25B:
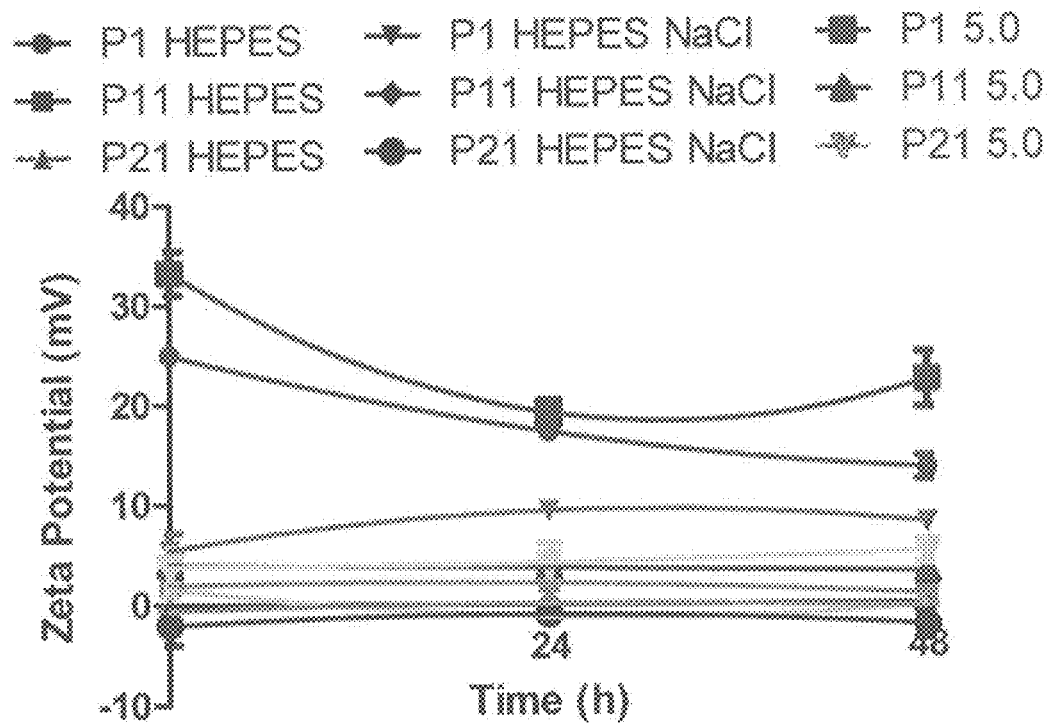

FIG. 25B is a plot of zeta potential (mV) as a function of time for coated micelles in different buffer solutions after centrifugation to remove excess PEO-b-PGA.

Figure 26A:
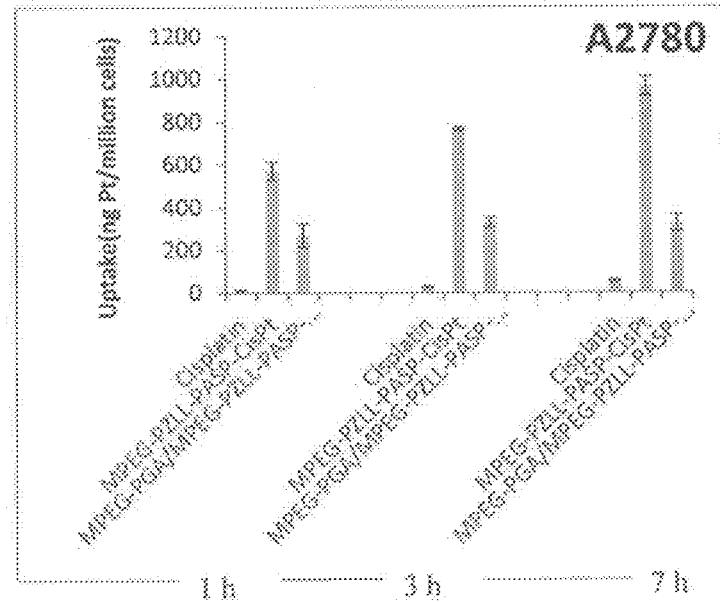

FIG. 26A is a bar graph indicating uptake (ng Pt/million cells) for coated and uncoated polymer micelles. A2780 cells were plated in 6-well plate at 1 million cells/well and uptake of coated and uncoated polymeric micelles conjugated to cisplatin (IV) were monitored as a function of time (1 h, 3 h, or 7 h) after cellular addition. All cells were treated at a final concentration Pt=40 µM.

Figure 26B:
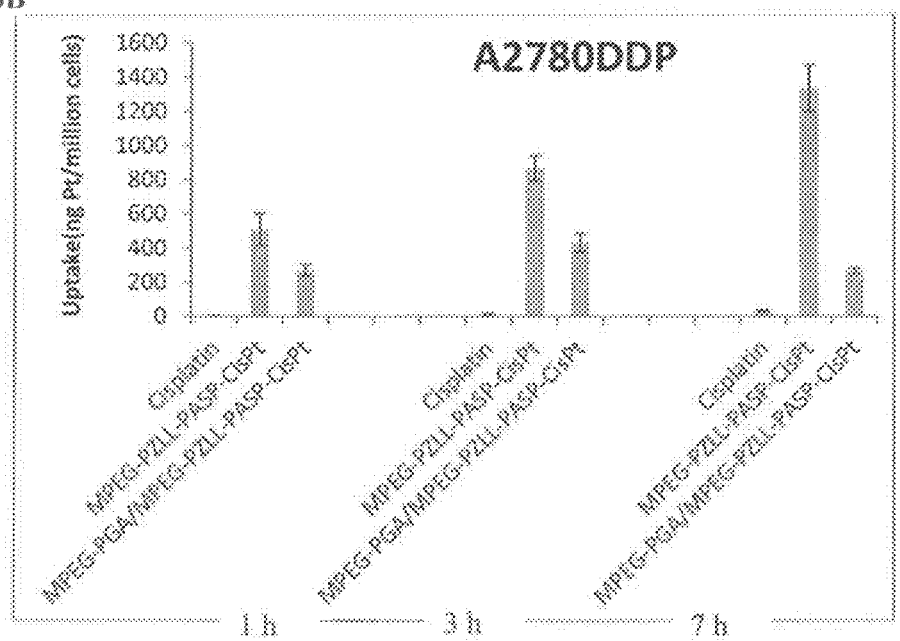

FIG. 26B is a bar graph indicating uptake (ng Pt/million cells) for coated and uncoated polymer micelles. A2780DDP cells were plated in 6-well plate at 1 million cells/well and uptake of coated and uncoated polymeric micelles conjugated to cisplatin (IV) were monitored as a function of time (1 h, 3 h, or 7 h) after cellular addition. All cells were treated at a final concentration Pt=40 µM.

Figure 27:
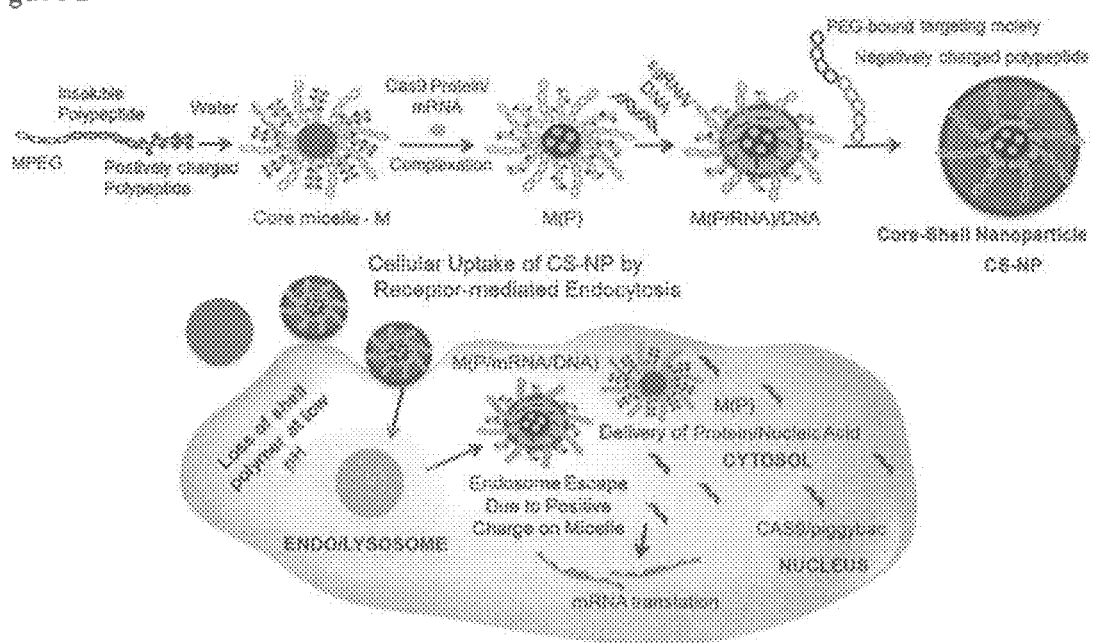

FIG. 27 is a schematic representation of delivery of CRISPR/Cas9 gene editing tools to a cell.

Figures 28A, 28B, 28C, 28D, 28E, 28F, 28G, 28H:
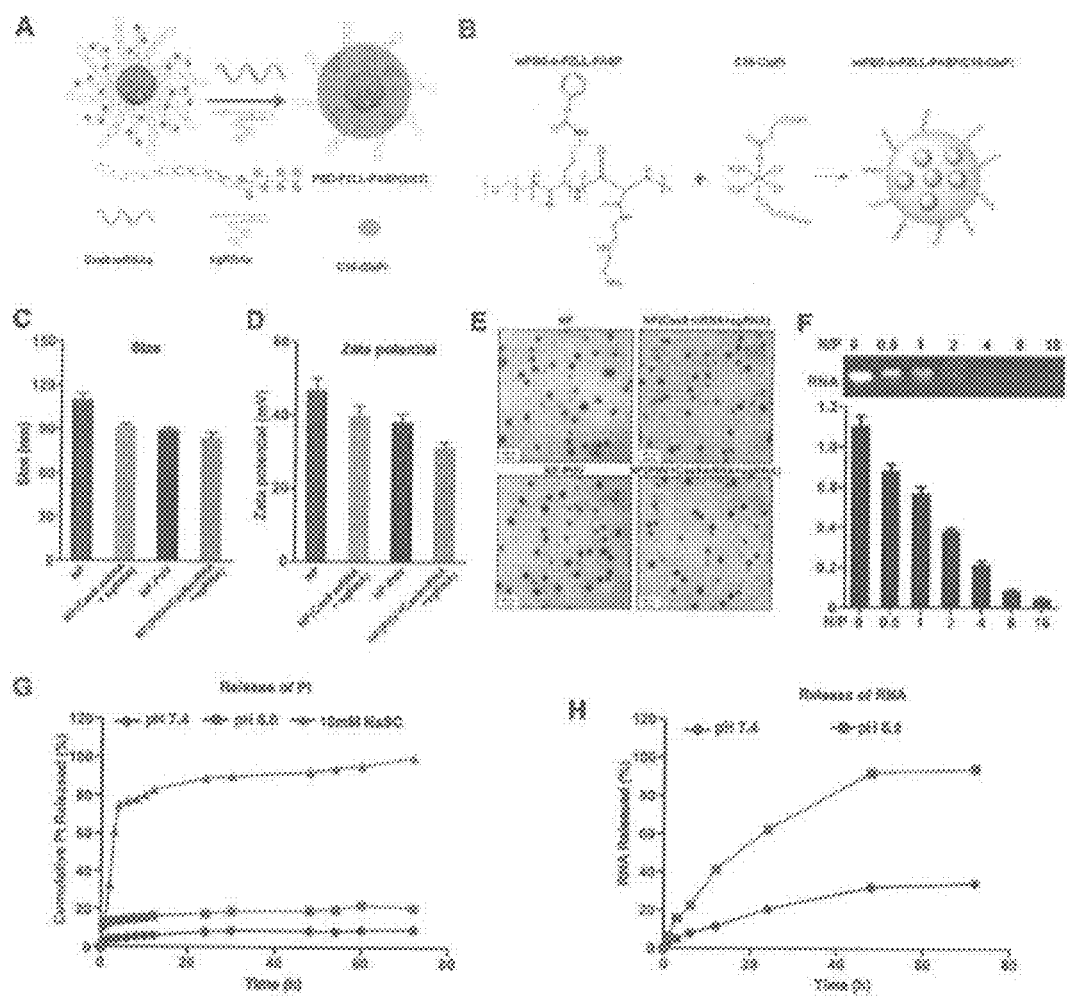

FIG. 28A is a schematic representation of the chemical structure of PEO-PZLL-PASP. The particle consists of three components: (i) an outer PEG surface, (ii) a PASP layer that plays two roles: (a) acting as a polymer matrix loaded with nonpolar drugs and (b) protecting and promoting siRNA molecule retention inside the NP core and controlling drug release, and (iii) an aqueous inner core containing Cas9 mRNA and gRNA.

FIG. 28B shows the chemical structure of the hydrophobic platinum(IV) and the chemistry by which the active drug cisplatin is released after reduction in the cell.

FIG. 28C is a bar graph showing the size distribution of the NPs containing Cas9 mRNA and gRNA determined by dynamic light scattering.

FIG. 28D is a bar graph showing the zeta potential distribution of the NPs containing Cas9 mRNA and gRNA determined by dynamic light scattering.

FIG. 28E is a series of representative transmission EM images of the NPs.

FIG. 28F is a bar graph showing heparin displacement assay of siRNA after complexation with copolymers at an N/P ratio of 0 to 16.

FIG. 28G is a plot of Pt release profiles (%) of NPs at pH 7.4 and 5.0.

FIG. 28H is a plot of RNA release profiles (%) of NPs at pH 7.4 and 5.0.

Figures 29A, 29B, 29C:
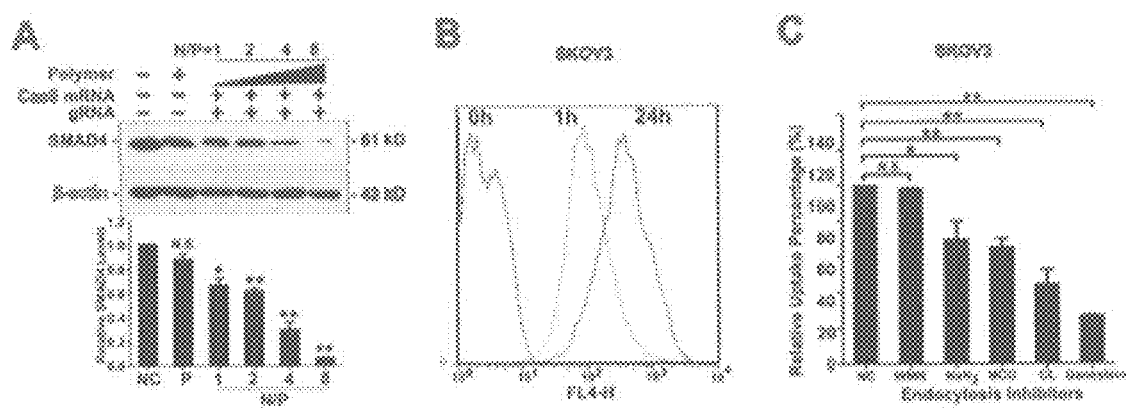

FIG. 29A summarizes data showing the silencing efficacy of NPs at N/P ratio from 1 to 8. SMAD4 expression were detected by western blotting 3 days post transfection.

FIG. 29B is a plot of the uptake of RNA. Cy5-labeled RNA were incorporated in NPs and transfected to SKOV3 cells at N/P ration 8. Flow cytometry were used to analyze the uptake of RNAs.

FIG. 29C is a bar graph showing uptake into SKOV3 cells. Cells were treated with various endocytosis inhibitors for 2 hours and then transfected with NPs containing cy5-labeled RNAs for 2 hours. WMN, wortmannin; $NaN_3$, sodium azide; MCD, methyl-beta-cyclodextrin; CL. Uptake percentages normalized as to positive control. Means±SEM of a representative experiment (n=3) performed in triplicates are shown.

Figure 29D:
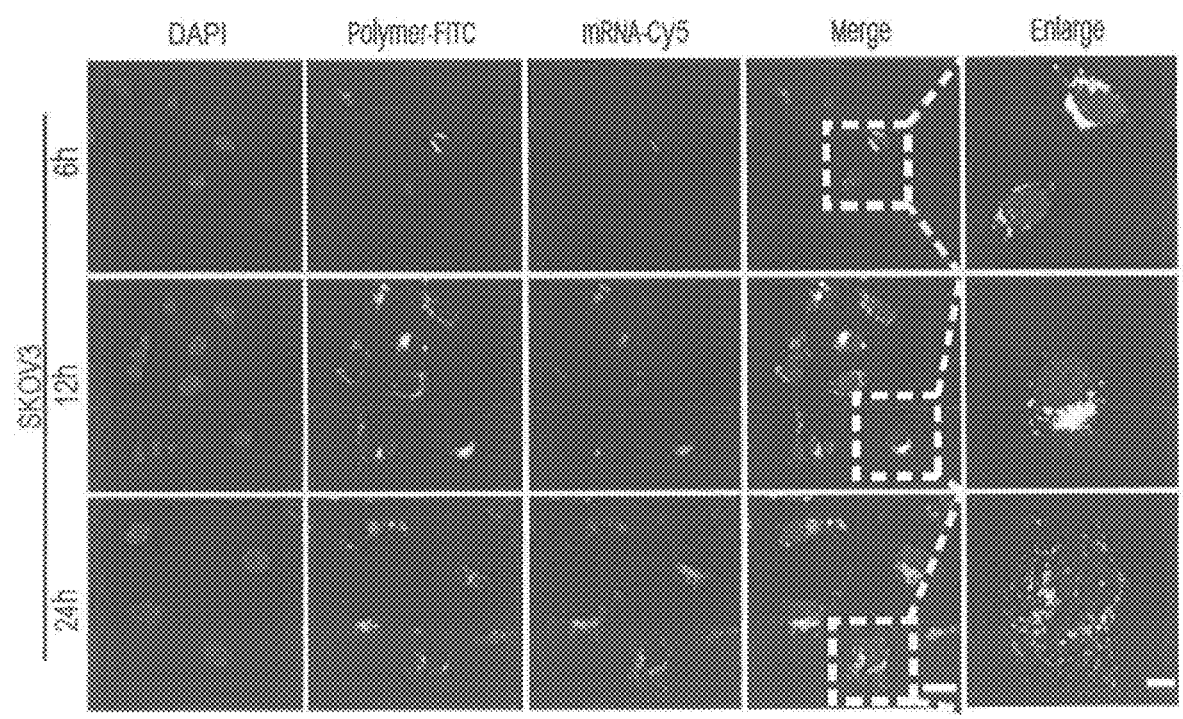

FIG. 29D is a series of confocal laser scanning micrographs of SKOV3 cells incubated with FITC-labeled NPs loading with cy5-labeled RNA for 6 hours, 12 hours and 24 hours. Blue: DAPI; Green: FITC; Red: Cy5. Left bar: 30 µm. Right bar: 10 µm.

Figures 30A, 30B, 30C, 30D:
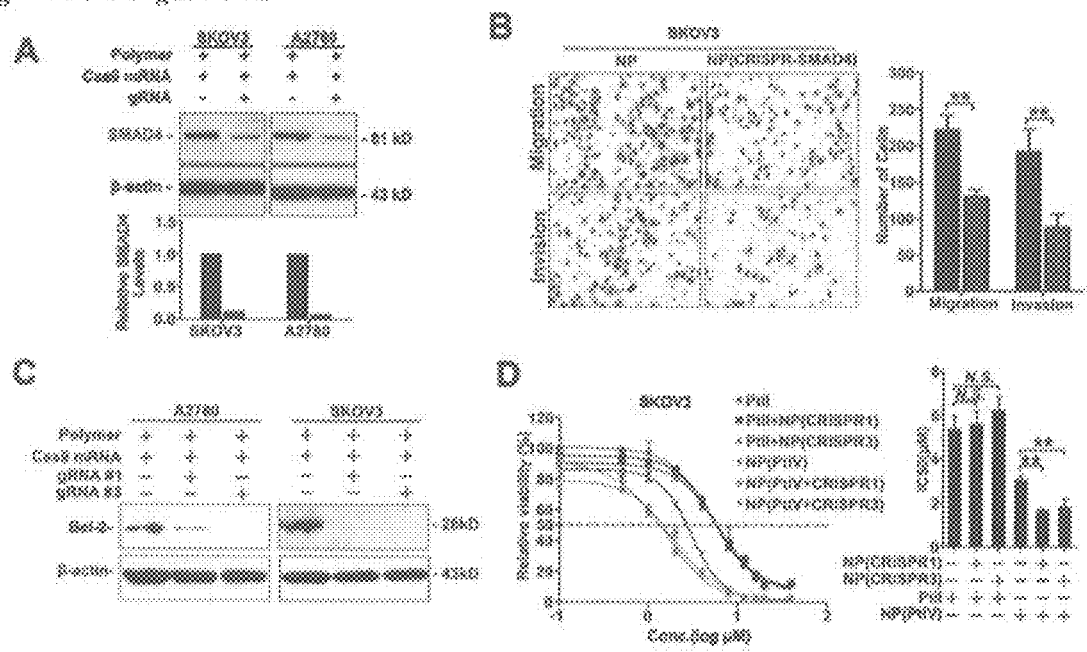

FIG. 30A summarizes data showing NPs containing Cas9 mRNA and gRNA targeting SMAD4 decrease SMAD4 expression 3 days after transfection in SKOV3 and A2780 cells. Western blotting were used to detect the expression of SMAD4.

FIG. 30B summarizes data showing silencing SMAD4 using NPs containing CRISPR/Cas9 system decrease migration and invasion in SKOV3 cells.

FIG. 30C summarizes data showing NPs containing Cas9 mRNA and gRNA targeting BCL-2 decrease its expression 3 days after transfection in SKOV3 and A2780 cells. Western blotting were used to detect the expression of BCL-2.

FIG. 30D summarizes data showing: Left—Cell viability after being treated with escalating dosage of cisplatin or NP (Cisplatin IV) with or without NP(CRISPR1) or NP(CRISPR3); Right—$IC_{50}$ of cisplatin.

Figures 30E, 30F, 30G:
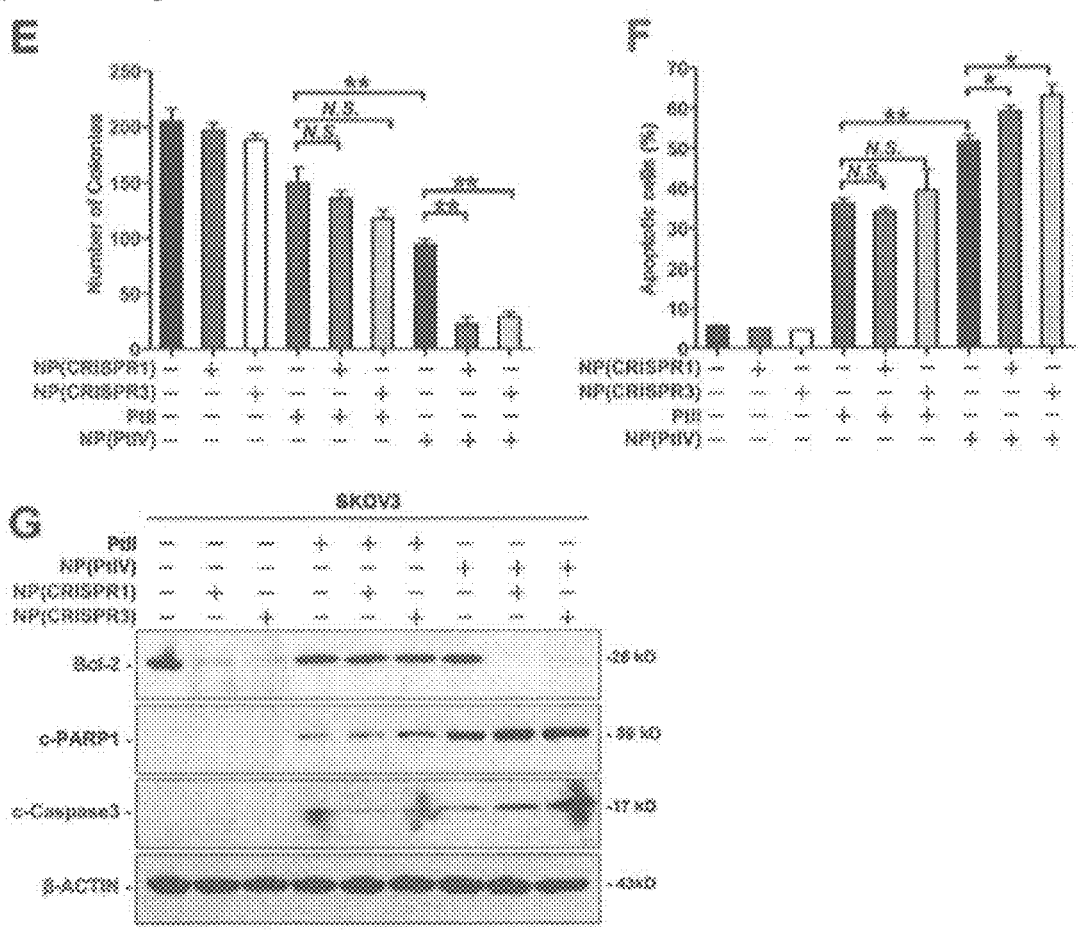

FIG. 30E is a bar graph showing colony formation assay of SKOV3 cells treated with cisplatin or NP (Cisplatin IV) with or without NP(CRISPR1) or NP(CRISPR3) for 10 days. Platinum concentration: 1 uM.

FIG. 30F is a bar graph showing apoptosis assay of SKOV3 cells treated with cisplatin or NP (Cisplatin IV) with or without NP(CRISPR1) or NP(CRISPR3) for 72 hours. Platinum concentration: 10 uM.

FIG. 30G is a western blotting assay of BCL-2, cleaved-PARP1, and cleaved-CASEPASE3 in SKOV3 cells treated with cisplatin or NP (Cisplatin IV) with or without NP(CRISPR1) or NP(CRISPR3) for 72 hours. Platinum concentration: 10 uM. Means±SEM of a representative experiment (n=3) performed in triplicates are shown.

Figures 31A, 31B, 31C:
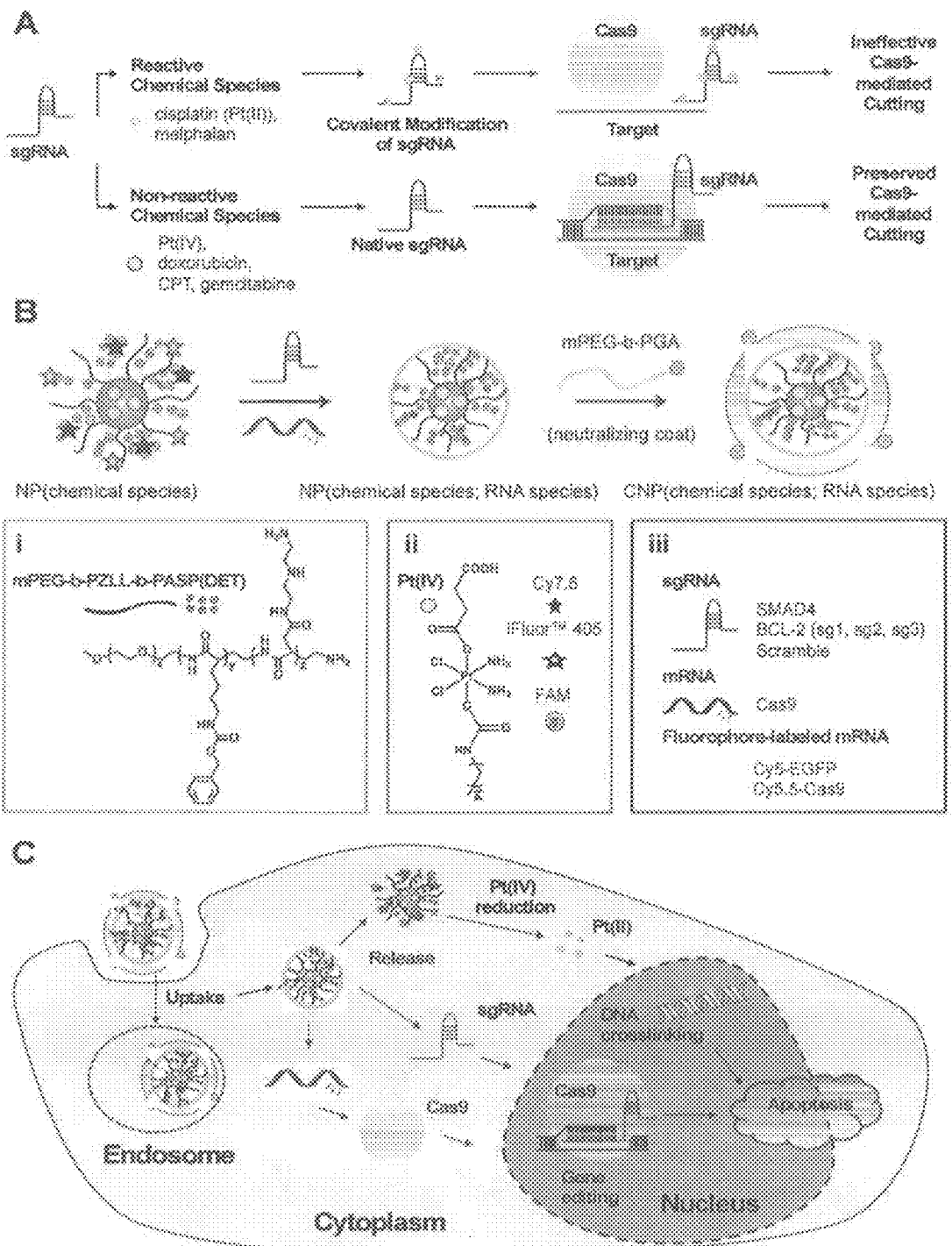

FIG. 31A is a schematic representation of reactive small molecule chemotherapeutics, such as platinum(II)-based anticancer agents (e.g. cisplatin; Pt(II)) or DNA-alkylators (e.g. melphalan), rapidly forming covalent adducts with sgRNA that prevent its binding to genomic DNA, resulting in ineffective cutting of target genes by the Cas9 nuclease. Non-reactive chemical species such as a lipophilic platinum (IV) prodrug (Pt(IV)), the topoisomerase inhibitors doxorubicin and campothecin (CPT), as well as the antimetabolite gemcitabine do not form covalent adducts with sgRNA, do not interfere with its ability to bind and recognize genomic DNA, and, hence, do not affect Cas9-mediated gene silencing.

FIG. 31B is a schematic depiction of a nanoparticle composition (NP) that may be used to incorporate small molecule chemotherapeutic agents (purple circles) and/or fluorescent dyes (grey and blue stars) as well as to electrostatically complex RNA species (red). The remaining cationic charge of the core NPs is neutralized via electrostatic binding of a shell polymer (e.g. poly(ethylene glycol)-block-poly(glutamic acid); mPEG-b-PGA), forming core-shell nanoparticles (CNPs) that protect their nucleic acid payload from degradation.

FIG. 31C is a schematic representation of uptake of into tumor cells and within their endosomes, the drop in pH (from 7.4, extracellularly, to approximately 5.5-6.0, intracellularly) results in release of the electrostatically complexed shell polymer (pKa of mPEG-b-PGA is 5.5-6.0) from the core nanoparticle followed by delivery of the RNA payload (i.e. the Cas9 mRNA and sgRNA species). Intracellular reduction of the Pt(IV) prodrug to active Pt(II) further results in its release from the nanoparticles. The CRISPR/Cas9 complex assembles in the cytoplasm and mediates cutting of target genomic DNA; released Pt(II) forms covalent Pt-DNA complexes; and, these two disparate species work in concert to augment cellular apoptosis.

Figure 32:
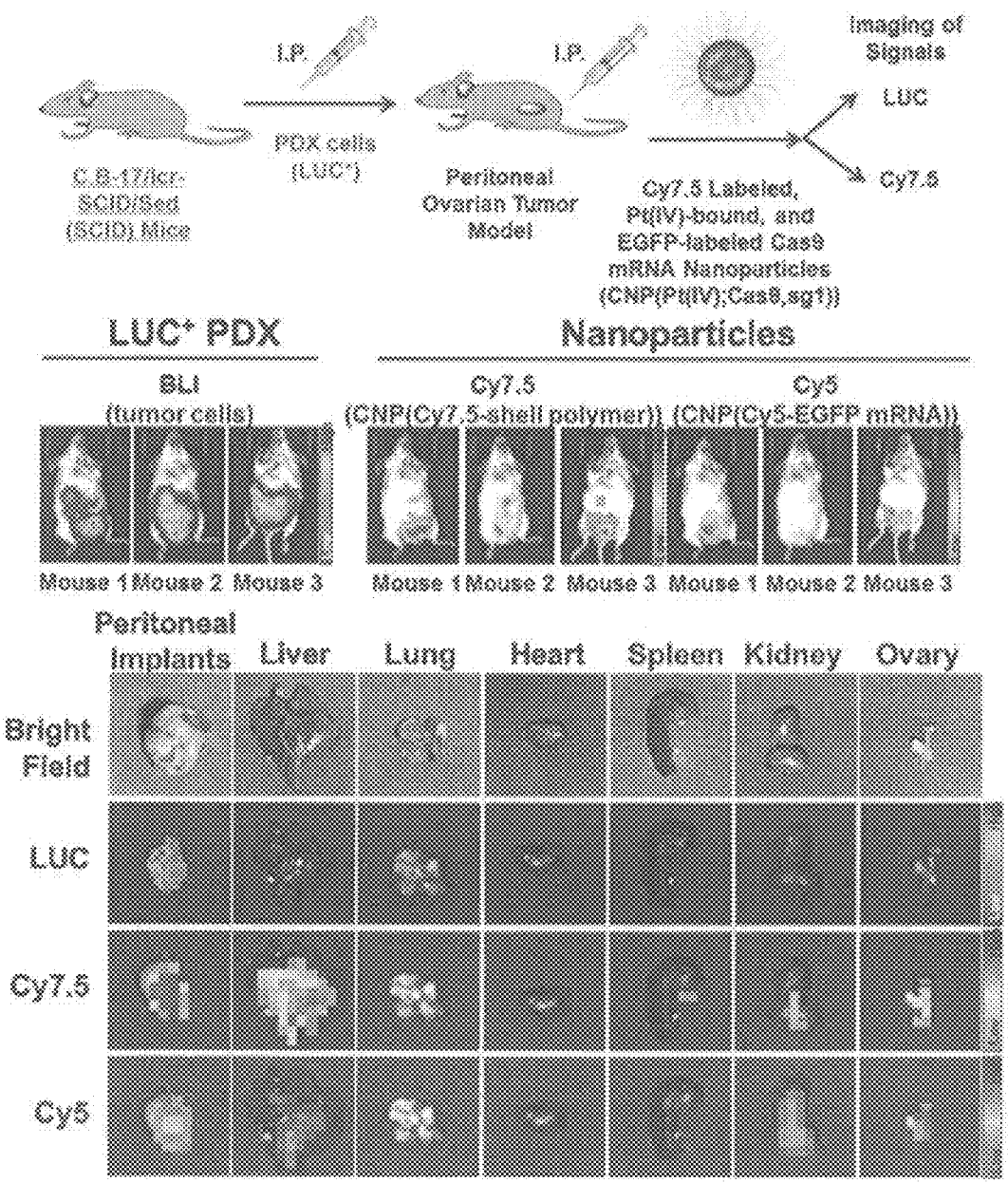

FIG. 32 shows a schematic representation and confocal images of in vivo and ex vivo biodistribution data showing co-localization of nanoparticles from FIG. 31 with peritoneal tumors in ovarian cancer PDX mice after IP injection.

Figure 33E:
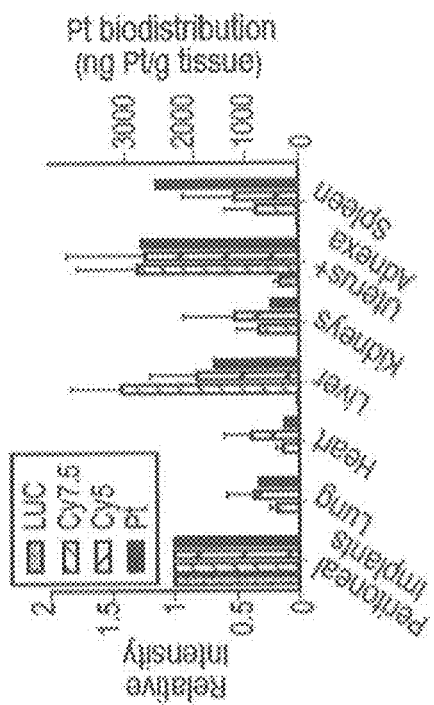
Figure 33B:
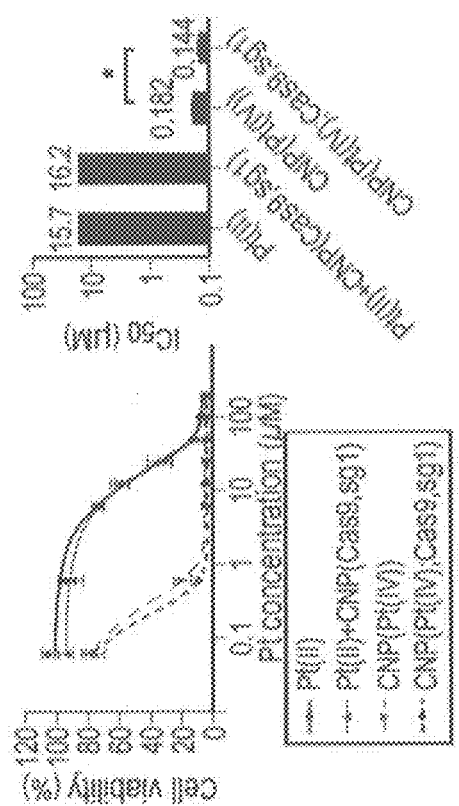
Figure 33D:
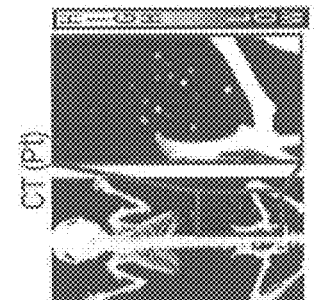
Figure 33A:
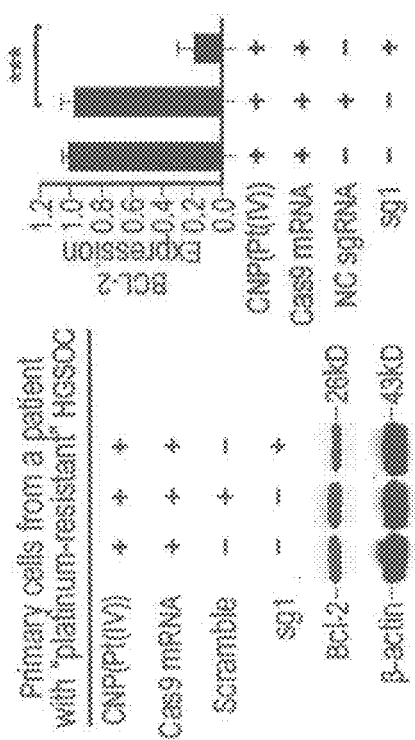

FIG. 33A shows the results of silencing of BCL-2 in primary cells derived from a patient with "platinum-resistant" and high-grade serous ovarian cancer (HGSOC) as assessed by WB; Cas9 mRNA and either negative control (neg cont) or BCL-2 sgRNA (sg1) were delivered with nanoparticles that were conjugated to Pt(IV) (NP(Pt(IV)). The relative expression levels of BCL-2 (right) were determined by normalizing values to B-actin (house-keeping gene) and are displayed in comparison to control (untreated cells).

FIG. 33B is a graph showing in vitro dose response curves and corresponding $IC_{50}$ values for the same primary HGSOC cells as determined by the CCK8 cellular viability assay.

Figure 33C:
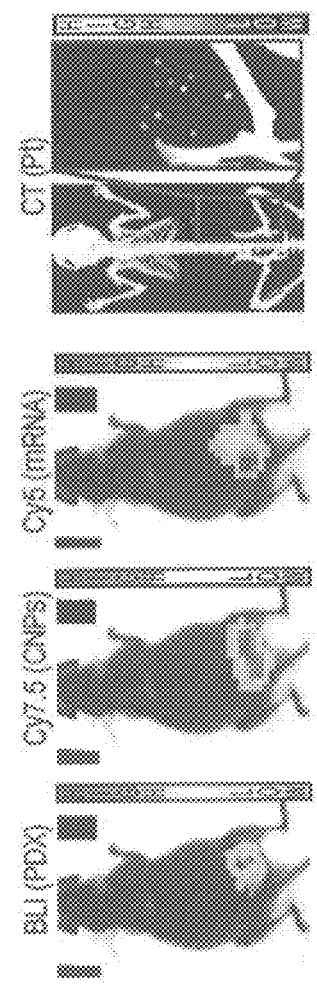

FIG. 33C are in vivo images showing biodistribution of fluorescently-tagged core-shell nanoparticles (CNPs) in PDX mice derived by IP dissemination of LUC+ primary cells from a patient with "platinum-resistant" HGSOC. BLI image (left) demonstrates peritoneal dissemination of the tumors cells; fluorescent images of Cy7.5 (middle) and Cy5 emission from the same mouse (right) depict the location of the CNPs and mRNA, respectively.

FIG. 33D is a CT image of the same mouse depicting the approximate location of the CNPs as determined by contrast enhancement afforded by their high concentrations of Pt(IV).

FIG. 33E is a plot of relative biodistribution of the BLI signals (tumor cells; blue), Cy7.5 emission (CNPs; green), Cy5 (mRNA; red) and platinum (Pt; purple) in tissues excised from 3 mice that were similarly treated and processed, demonstrating the high intratumoral delivery of Cy5.5-conjugated CNPs along with a separate CNP formulation containing Cy5-labeled mRNA.

FIG. 33F are images showing the high intratumoral delivery of Cy5.5-conjugated CNPs along with a separate CNP formulation containing Cy5-labeled mRNA.

FIG. 33G are IF images for cleaved caspase 3 (cCaspase 3) in the BCL-2 locus of PDX tumors from mice that were treated with x2 weekly doses of various experimental groups.

FIG. 33H is a bar graph showing WB of BCL-2 expression levels in the BCL-2 locus of PDX tumors from mice that were treated with x2 weekly doses of various experimental groups.

FIG. 33I shows next-generation sequencing for the frequency of indels in the BCL-2 locus of PDX tumors from mice that were treated with x2 weekly doses of various experimental groups.

Figure 33L:
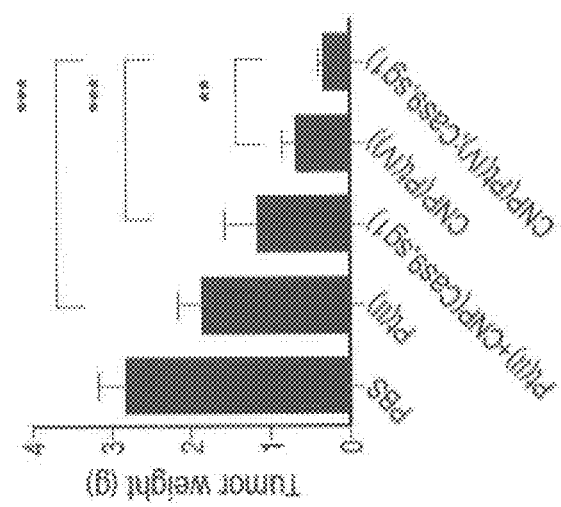
Figure 33K:
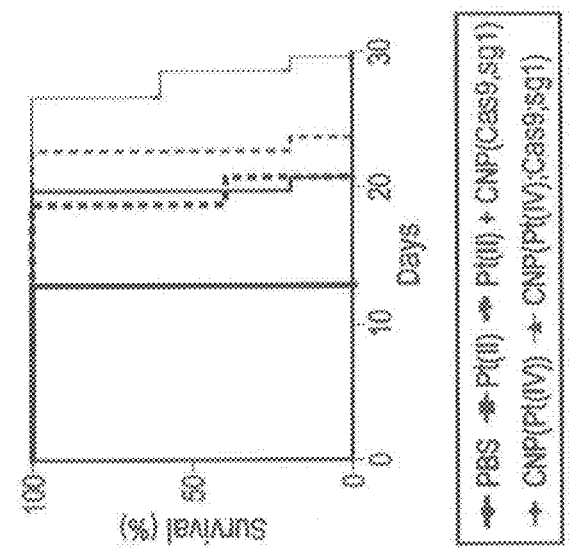
Figure 33J:
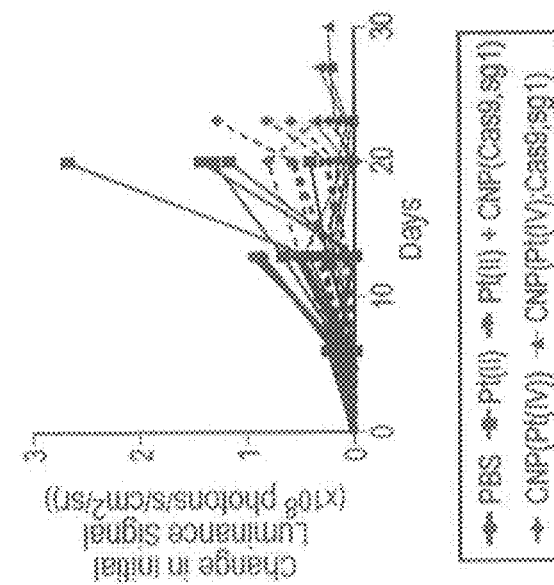

FIG. 33J is a graph showing relative inhibition of BLI signals generated from LUC+PDX tumors excised upon sacrifice from PDX mice that were treated with x4 weekly IP injections of each of the various experimental groups. *p<0.05, p<0.01, *p<0.001.

FIG. 33K shows the Kaplan-Meir survival curve from PDX mice that were treated with x4 weekly IP injections of each of the various experimental groups. *p<0.05, p<0.01, *p<0.001.

FIG. 33L is a bar graph showing the weights of tumors excised upon sacrifice from PDX mice that were treated with x4 weekly IP injections of each of the various experimental groups. *p<0.05, p<0.01, *p<0.001.

FIG. 34 is a table summarizing RNA species, their abbreviations, and their sequences.

FIG. 35 is a table summarizing various nanoparticle formulations described herein.

Figures 36A, 36B, 36C, 36D:
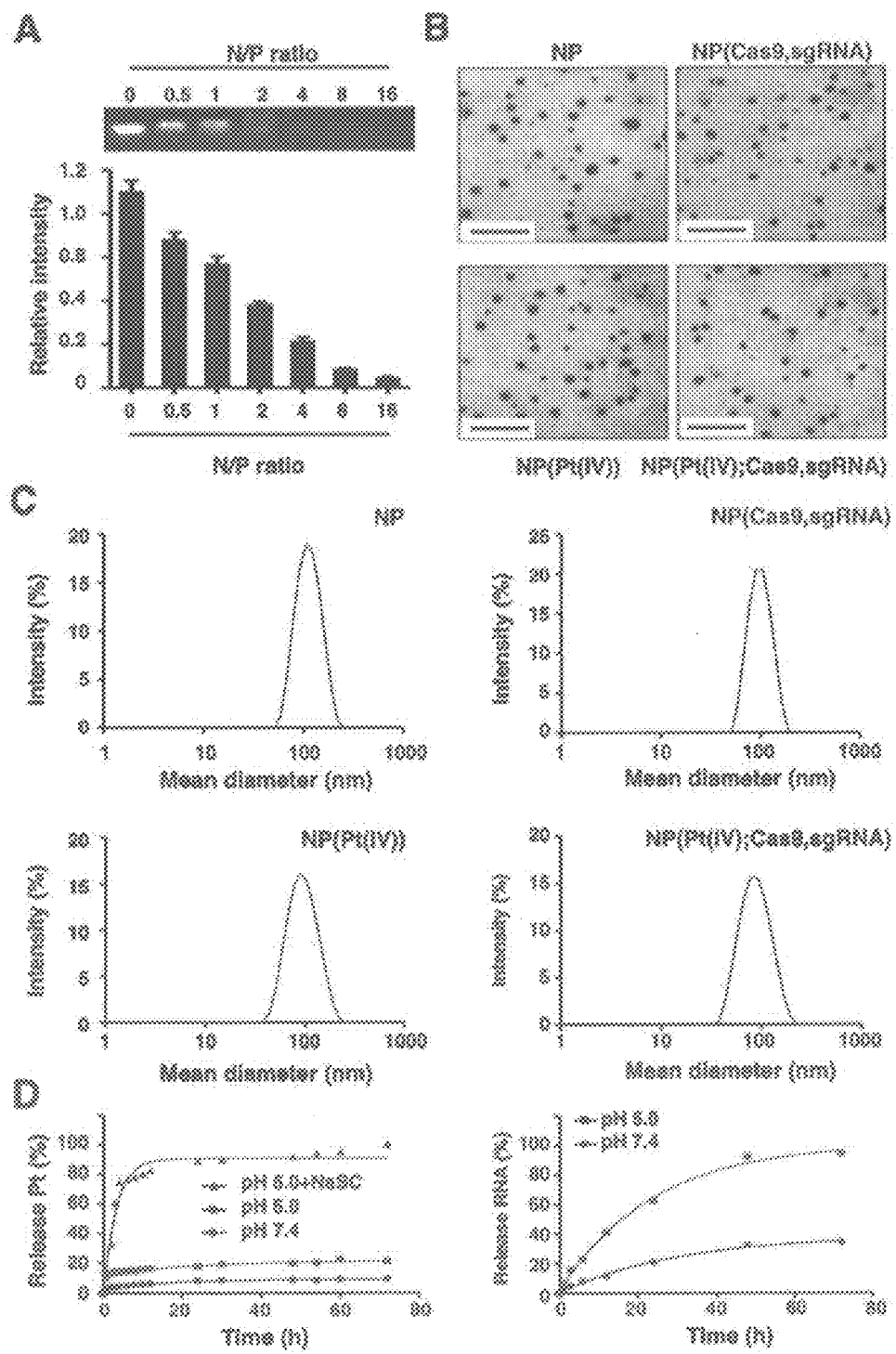

FIG. 36A is a bar graph showing selection of the optimal N/P ratio for complexation of sgRNA. The relative electrophoretic mobility of sgRNA in an agarose gel was determined after complexation with nanoparticles formed from unmodified mPEG-b-PZLL-b-PASP(DET) in water (NP) and as a function of different initial ratios of amino groups on the polymer (N) to phosphate groups on the RNA (P) (i.e. N/P ratios). The relative intensities of the resultant migration bands were quantified after ethidium bromide staining.

FIG. 36B are images showing the size distributions of different nanoparticle formulations were determined by transmission electron microscopy (TEM, Scale bar=1 μm). Similar experimental characterizations were conducted for NP, after its complexation with Cas9 mRNA and sgRNA (i.e. NP(Cas9,sgRNA), after formation of nanoparticles from mPEG-b-PZLL-b-PASP(DET)-Pt(IV) (i.e. NP(Pt(IV)), and after further complexation of these Pt(IV)-containing nanoparticles with Cas9 mRNA and sgRNA (i.e. NP(Pt(IV); Cas9,sgRNA).

FIG. 36C are graphs showing the size distributions of different nanoparticle formulations were determined by dynamic light scattering (DLS). Similar experimental characterizations were conducted for NP, after its complexation with Cas9 mRNA and sgRNA (i.e. NP(Cas9,sgRNA), after formation of nanoparticles from mPEG-b-PZLL-b-PASP (DET)-Pt(IV) (i.e. NP(Pt(IV)), and after further complexation of these Pt(IV)-containing nanoparticles with Cas9 mRNA and sgRNA (i.e. NP(Pt(IV);Cas9,sgRNA).

FIG. 36D are graphs showing the in situ kinetics of release of free Pt(II) (left) and Cy5.5-labeled Cas9 mRNA (Cy5.5-Cas9; right) from NP(Pt(IV);Cy5.5-Cas9,sgRNA) as a function of solution pH (5.0 vs. 7.4) and the presence of additional sodium ascorbate (NaSC, 5 mM).

Figure 37:
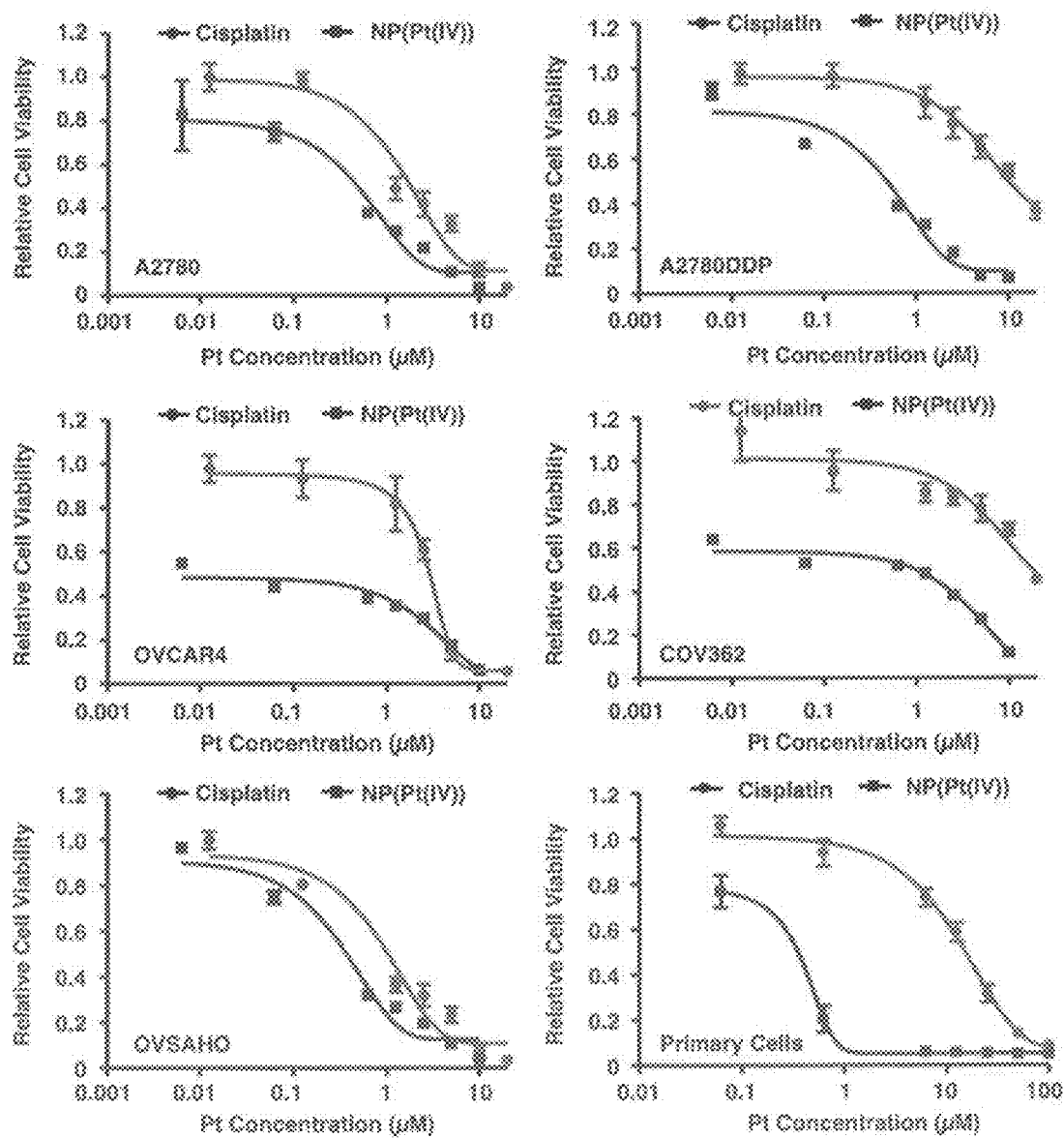

FIG. 37 are graphs showing the comparison of the relative in vitro anti-proliferative activity of nanoparticle-conjugated Pt(IV) (NP(Pt(IV))) as compared to cisplatin (Pt(II)). A2780 and A2780DDP were utilized as an isogenic pair of cell lines for which the latter is known to display relative Pt(II) resistance; OVCAR4, COV362 and OVSAHO are established ovarian cancer cell lines that possess genetic signatures that match those of high-grade serous ovarian cancers (HGSOCs). Each of these adherent cell lines were incubated with either NP(Pt(IV)) or Pt(II) at equimolar Pt concentrations; and, their relative cellular viability after 72 h was assessed by the colorimetric MTT assay. Similarly, primary cells from a patient with advanced stage and "platinum resistant" HGOSC (PDX) were incubated with the same treatments at identical concentrations and for 72 h; cellular viability measurements of these suspension cultures (primary patient-derived cells) were performed using the colorimetric CCK8 assay, following established protocols.

Figures 38A, 38B:
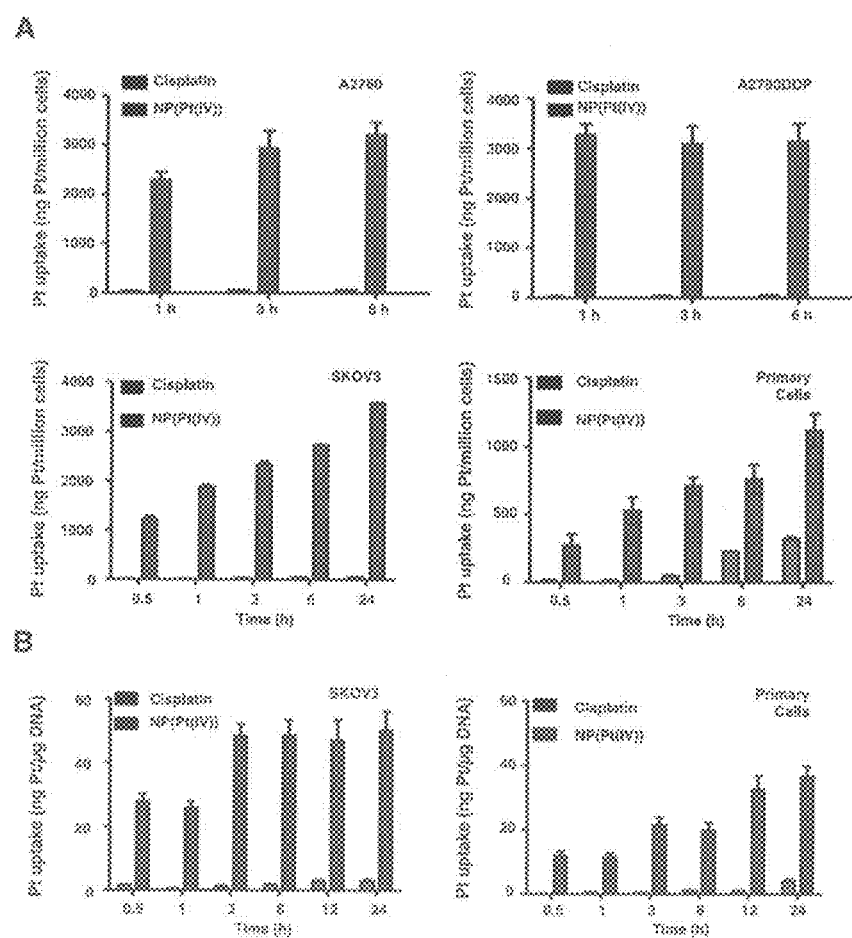

FIG. 38A are bar graphs showing quantification of the intracellular levels of Pt as a function of time after incubation with cisplatin (Pt(II)) versus nanoparticle-conjugated Pt(IV) (NP(Pt(IV))). Several established ovarian cancer cells lines (A2780, A2780DDP, SKOV3) and primary cells form a patient with platinum-resistant high-grade serious ovarian cancer (PDX) were incubated with equimolar amounts (40 μM) of either cisplatin or NP(Pt(IV)); and, the levels of intracellular and DNA-bound Pt were determined by ICP-MS as a function of time after treatment addition.

FIG. 38B are bar graphs showing quantification of the intracellular levels of Pt-DNA adducts as a function of time after incubation with cisplatin (Pt(II)) versus nanoparticle-conjugated Pt(IV) (NP(Pt(IV))). Several established ovarian cancer cells lines (A2780, A2780DDP, SKOV3) and primary cells form a patient with platinum-resistant high-grade serious ovarian cancer (PDX) were incubated with equimolar amounts (40 μM) of either cisplatin or NP(Pt(IV)); and, the levels of intracellular and DNA-bound Pt were determined by ICP-MS as a function of time after treatment addition.

Figure 39A:
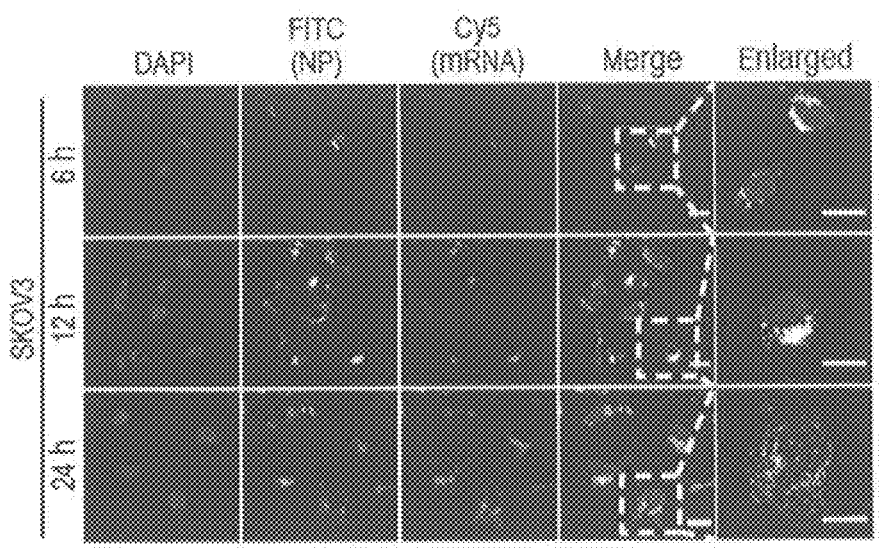

FIG. 39A are confocal laser scanning micrographs of SKOV3 cells at various time points after their incubation with FITC-labeled nanoparticles (NPs) that were complexed with Cy5-conjugated mRNA (N/P ratio=8); blue channel: DAPI; green channel: FITC (conjugated to NPs); red channel: Cy5 (bound to the mRNA); left scale bar: 30 μm; right scale bar: 10 μm.

Figures 39B, 39C, 39D, 39E, 39F:
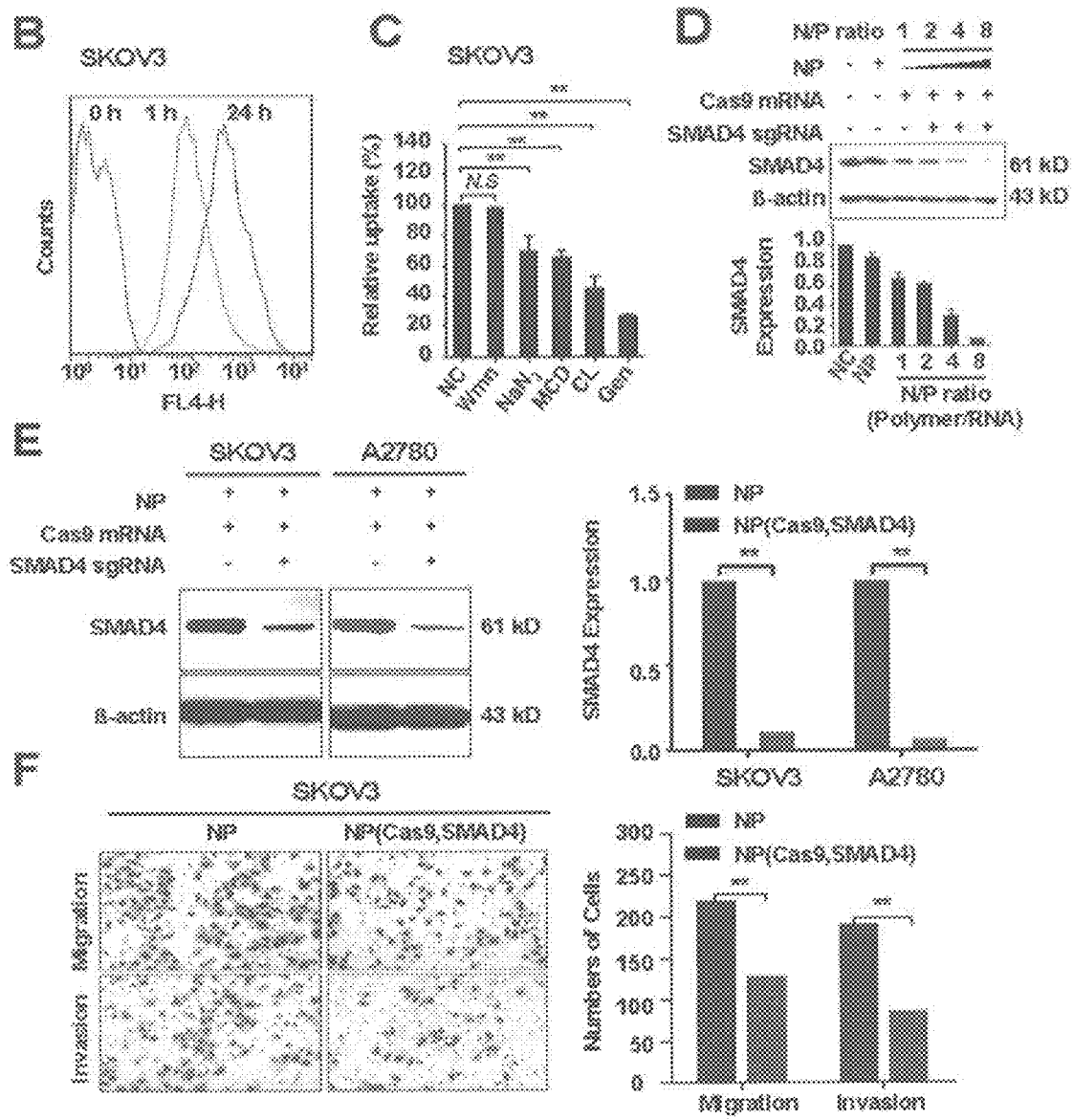

FIG. 39B are flow cytometry histograms depicting an increase in the population of Cy5-labeled SKOV3 cells as a function of time after incubation with NP-bound and Cy5-labeled mRNA.

FIG. 39C is a bar graph showing the results when SKOV3 cells were pretreated with various endocytosis inhibitors, including sodium azide (NaN3), genistein (gen), chlorpromazine (CL), wortmannin (WMN), or methyl-β-cyclodextrin (MCD), for 2 h prior to NP-based transfection of Cy5-labeled mRNA. Mean values±SEM from a single experiment are displayed; the experiments were performed in triplicate; and, the reported values are representative of additional runs.

FIG. 39D are the results associated with WB performed at 72 h to determine relative silencing efficiency of CRISPR/Cas9 targeting SMAD4 as a function of the ratio of the amino groups (N) of the polymer to the phosphate groups (P) of the total RNA (i.e. sgRNA plus mRNA) used to generate RNA-complexed NPs for delivery to SKOV3 cells.

FIG. 39E shows NPs containing Cas9 mRNA and SMAD4 sgRNA decreased SMAD4 expression by WB at 72 h after transfection in SKOV3 and A2780 cells.

FIG. 39F shows silencing of SMAD4 using NPs delivering the CRISPR/Cas9 components decreased migration and invasion in SKOV3 cells plated on gels. *$p<0.05$; $p<0.01$; *$p<0.001$.

Figures 40A, 40B, 40C, 40D, 40E:
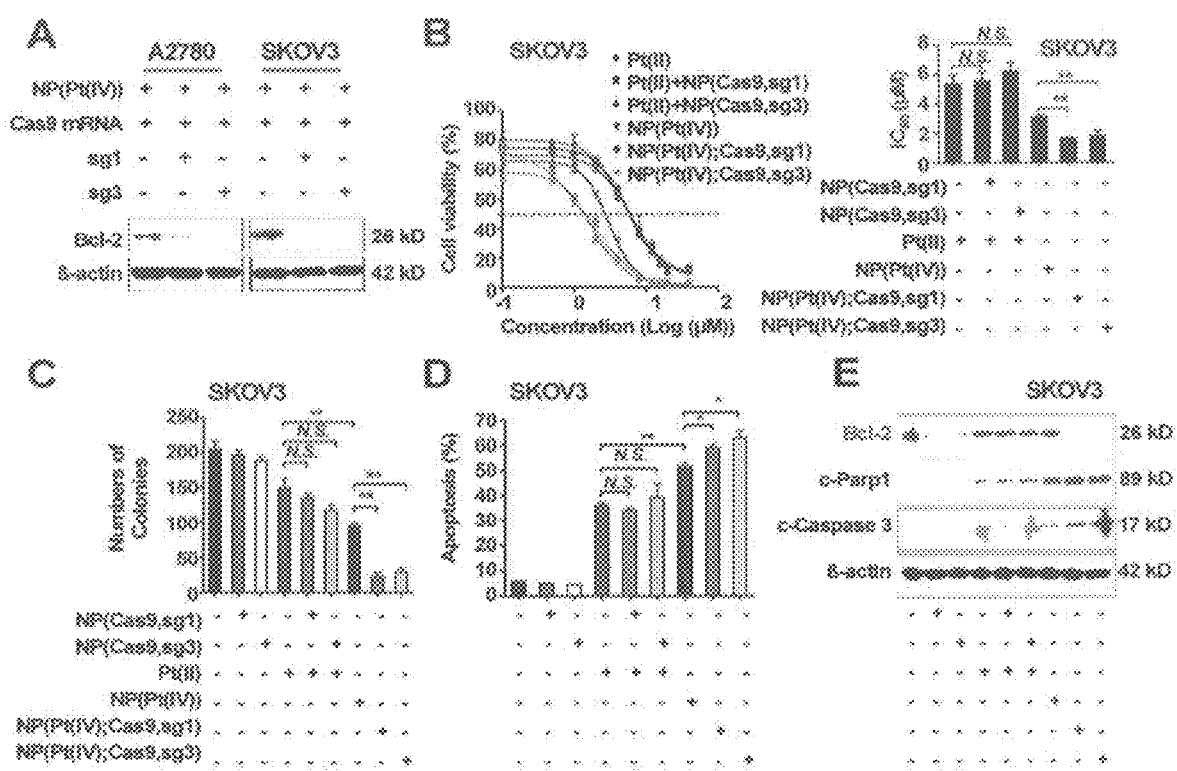

FIG. 40A shows that WB was used to detect the expression of BCL-2 in SKOV3 and A2780 cells at 72 h after incubation with various treatments, including nanoparticle-conjugated Pt(IV) alone (NP(Pt(IV)) or after its further complexation to Cas9 mRNA and two different BCL-2 sgRNAs (i.e. sg1 and sg3).

FIG. 40B are cell viability plots of SKOV3 cells at 72 h after treatment with escalating doses of Pt(II) alone or when combined with nanoparticle formulations that complexed Cas9 mRNA and either sg1 or sg3 (i.e. NP(Cas9,sg1) and NP(Cas9,sg3), respectively); note, nanoparticles that covalently conjugated Pt(IV) alone (i.e. NP(Pt(IV)) or that further complexed Cas9 mRNA and either sg1 or sg3 (i.e. NP(Pt(IV);Cas9,sg1) and NP(Pt(IV);Cas9,sg3), respectively) were employed for comparison; the corresponding $IC_{50}$ values for these plots are depicted (right). Mean values±SEM are shown at each time point and were derived from three experimental replicates (each containing 3 technical replicates per condition).

FIG. 40C is a bar graph showing enumeration of colony formation for SKOV3 cells at 10 days after incubation with various treatments.

FIG. 40D is a bar graph showing apoptosis of SKOV3 cells at 72 h after incubation with various treatments.

FIG. 40E shows WB for BCL-2, cleaved PARP1 (c-Parp1), and cleaved Caspase3 (cCaspase 3) in SKOV3 cells at 72 h after incubation with various treatments.

DETAILED DESCRIPTION

Overview

In certain embodiments, the invention relates to triblock copolymers, such as methoxy-poly(ethylene glycol)-block-poly(carbobenzyloxy-L-lysine)-block-poly(aspartamide) (mPEG-b-PZLL-b-PASP(DET)), that self-assemble into a biodegradable nanoparticle with a bioinert surface comprised of PEG, a hydrophobic core made up of the artificial polypeptide PZLL, and corona comprised of the cationic polypeptide PASP(DET). In certain embodiments, the nanoparticles further comprise a Pt species, such as a lipophilic platinum(IV) prodrug of cisplatin (Pt(IV)), covalently bound to the polymer and segregated within the PZLL core of the nanoparticles; this serves to physically separate it from the CRISPR/Cas9 components that are electrostatically complexed with the PASP(DET) corona. Layer-by-layer assembly using an anionically charged methoxy-PEG-block-poly (glutamic acid) (mPEG-b-PGA) polymer serves to stabilize the nanocomplex, neutralize its overall surface charge, and further protect the nucleic acid payload from environmental reactants. In certain embodiments, the nanoparticles further comprise a fluorophore-labeled mRNA compound, a target sgRNA, or a control sgRNA.

In certain embodiments, the invention relates to nanoparticles that can deliver Cas9 mRNA and sgRNA with and without a platinum(IV) prodrug, in particular, for the treatment of patients with "platinum-resistant" or high-grade serous ovarian cancer (HGSOC). In certain embodiments, the nanoparticles do not comprise any targeting agents and still associate within disseminated peritoneal tumors after intraperitoneal (IP) injection, which is a clinically elegant mode of therapeutic administration for patients with advanced ovarian cancers. In certain embodiments, the nanoparticles that comprise CRISPR/Cas9 components and platinum-based small molecules overcome therapeutic resistance and prolong survival, offering a translational strategy for patients with otherwise limited therapeutic options.

In certain embodiments, the invention relates to a transfection reagent comprised of biodegradable poly(ethylene glycol)-block-poly-(ε-caprolactone)-block-poly(L-lysine) triblock copolymer (i.e. PEO-b-PCL-b-PLL) that self-assembles into polymeric micelles that are capable of OxaPt (IV) conjugation or siRNA electrostatic complexation. Notably, co-incorporation of OxaPt(IV) and BCL-2 siRNA within a single micellar construct prevents siRNA transcript inactivation, promotes the highest intracellular levels of both oxaliplatin and siRNA, maximizes in vitro potency, and affords the greatest degree of synergistic biological activity.

Figure 1A:
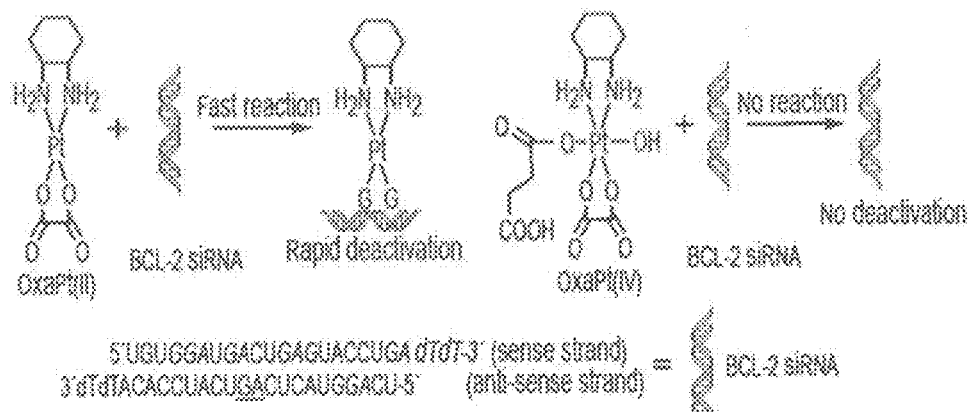
FIG. 1A is a series of two reaction schemes. On the left is shown a schematic representation of planar OxaPt(II) rapidly forming Pt-RNA adducts with BCL-2 siRNA, resulting in transcript inactivation. On the right is shown a schematic representation of kinetically inert octahedral OxaPt(IV) species, which does not form Pt-RNA adducts with BCL-2 siRNA. Notably, as seen from the sequence of the BCL-2 siRNA (bottom), platination of a single GG region in the non-seed portion of the anti-sense strand (red/underlined) would be expected to effect silencing efficacy; the sense and anti-sense strands also contain other potential sites for further platination (red/italics).
Figure 1B:
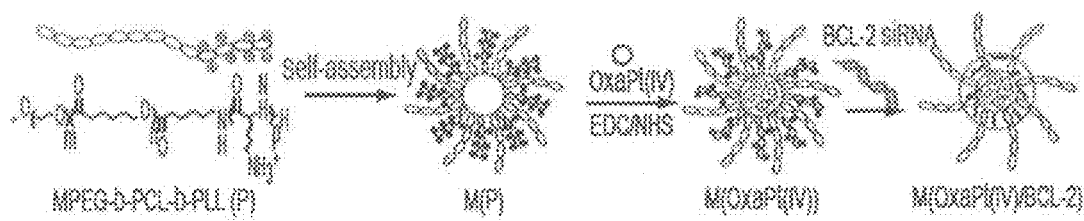
FIG. 1B is a reaction scheme for forming MPEG-b-PCL-b-PLL micelles (i.e. M(P)) incorporating OxaPt(IV) (i.e. M(OxaPt(IV)) or both OxaPt(IV) and Bcl-2 siRNA (i.e. M(OxaPt(IV)/BCL-2) in a single nanoparticle construct; note, OxaPt(IV) is linked through an amide bond while BCL-2 siRNA is bound through electrostatic complexation to amine groups on the PLL chains of the micelles.
Figure 1C:
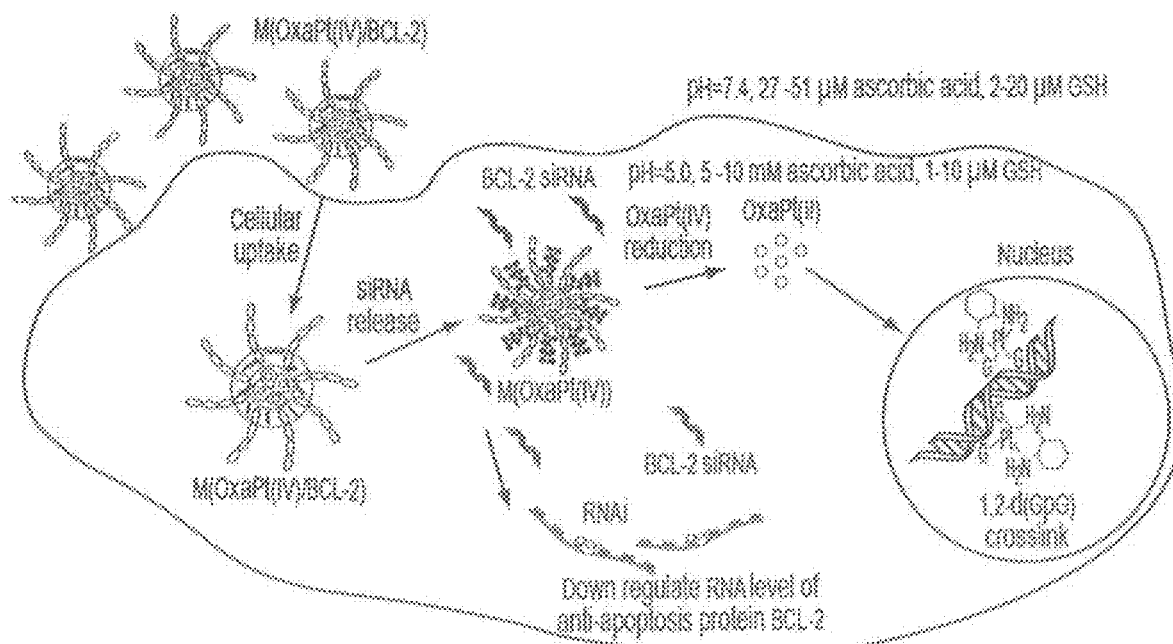
FIG. 1C is a schematic representation of the intracellular uptake and ultimate fate of M(OxaPt(IV)/Bcl-2) micelles. The micelles are taken up by endocytosis, where Bcl-2 siRNA is liberated at low pH; siRNA then enters the cytoplasm and results in suppression of BCL-2 mRNA expression. High intracellular concentrations of glutathione and ascorbic acid subsequently convert the OxaPt(IV) species to OxaPt(II), which is released due to liberation of the axial ligand on the platinum. Free OxaPt(II) subsequently binds DNA, resulting in Pt-DNA adduct formation and eventual cell death via apoptosis.
Figure 2:
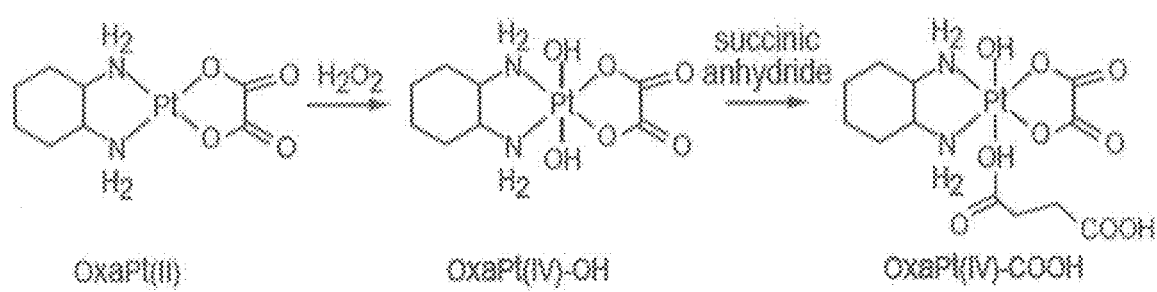
FIG. 2 is a schematic representation of the synthesis and chemical structures of OxaPt(IV)-OH and OxaPt(IV)—two platinum(IV) analogs of oxaliplatin (OxaPt(II)).
Figure 3:
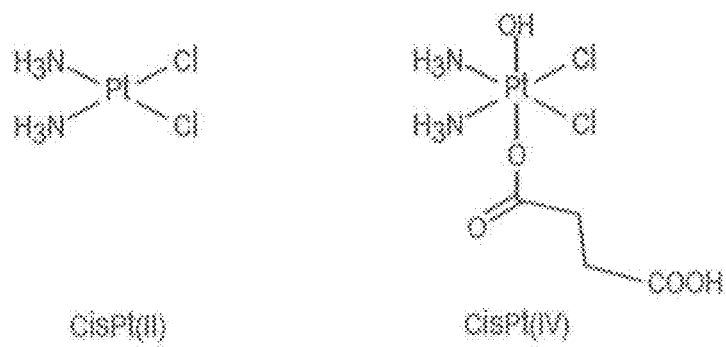
FIG. 3 is the chemical structures of cisplatin (CisPt(II)) (left) and a platinum(IV) analog (CisPt(IV)) (right).

In certain embodiments, the invention relates to octahedral platinum(IV) derivatives of OxaPt(II) and CisPt(II), which derivatives would expectedly have less chemical reactivity to guanine and adenine nucleotides (FIG. 1A, FIG. 2, FIG. 3). These platinum(IV) derivatives are converted to the active platinum(II) species only after cellular uptake, due to increased quantities of reductants found within cancer cells (e.g. 5-10 mM concentrations of glutathione and ascorbic acid exist intracellular as compared to 20-50 uM in either normal cells or within the extracellular milieu). The MCF-7 breast cancer and the OVCAR4 ovarian cancer cell lines were employed as in vitro model systems and the anti-apoptosis protein BCL-2 was selected as the target for RNAi; BCL-2 up-regulation has previously been shown to promote acquired platinum resistance in various malignancies. As an exemplary polynucleotide, a double-stranded siRNA transcript that contains multiple GG and GA regions but only a single GG sequence outside of the seed portion in the antisense strand was used; platination at this site would expectedly result in maximal thermal destabilization with decreased mRNA silencing (FIG. 1A). A nanoparticle transfection reagent comprised of the triblock copolymer of poly(ethylene glycol)-block-poly-(ε-caprolactone)-block-poly(L-lysine) (i.e. PEO-b-PCL-b-PLL) was further utilized to bind OxaPt(IV) and/or siRNA (FIG. 1B); it was employed to develop an optimal intracellular delivery strategy for combining RNAi and platinum-based small molecules (FIG. 1C).

Glossary

As used herein, the term "monomer," unless otherwise indicated, includes both isolated monomers and residues of monomers in an oligomer or a polymer (i.e. repeat units or residues).

The term "alkyl," as used herein, refers to a saturated aliphatic branched or straight-chain monovalent hydrocarbon radical having the specified number of carbon atoms. Thus, "$C_1$-$C_6$ alkyl" means a radical having from 1-6 carbon atoms in a linear or branched arrangement. Examples of "$C_1$-$C_6$ alkyl" include, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. An alkyl can be optionally substituted with halogen, —OH, $C_1$-$C_6$ alkyl, $C_1$-$C_6$ alkoxy, $C_6$-$C_{18}$ aryl, —$NO_2$, —CN, and —N($R^1$)($R^2$) wherein $R^1$ and $R^2$ are each independently selected from —H and $C_1$-$C_3$ alkyl.

The term "alkenyl," as used herein, refers to a straight-chain or branched alkyl group having one or more carbon-carbon double bonds. Thus, "$C_2$-$C_6$ alkenyl" means a radical having 2-6 carbon atoms in a linear or branched arrangement having one or more double bonds. Examples of "$C_2$-$C_6$ alkenyl" include ethenyl, propenyl, butenyl, pentenyl, hexenyl, butadienyl, pentadienyl, and hexadienyl. An alkenyl can be optionally substituted with the substituents listed above with respect to alkyl.

The term "carbocyclyl," as used herein, refers to refers to a ring system (monocyclic or polycyclic, including fused) wherein each of the atoms forming the ring is a carbon atom. Carbocyclyes include aryl and cycloalkyl rings. A carbocyclyl can be optionally substituted with the substituents listed above with respect to alkyl.

The term "cycloalkyl," as used herein, refers to a saturated monocyclic or fused polycyclic ring system containing from 3-12 carbon ring atoms. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. A cycloalkyl can be optionally substituted with the substituents listed above with respect to alkyl.

The term "amino," as used herein, means an "—$NH_2$," an "$NHR_p$," or an "$NR_pR_q$," group, wherein $R_p$ and $R_q$ can be alkyl, alkenyl, alkynyl, alkoxy, cycloalkyl, aryl, and heteroaryl. Amino may be primary ($NH_2$), secondary ($NHR_p$) or tertiary ($NR_pR_q$).

The term "alkylamino," which includes "cycloalkylamino," as used herein, refers to an "$NHR_p$," or an "$NR_pR_q$" group, wherein $R_p$ and $R_q$ can be alkyl, or cycloalkyl. The term "dialkylamino," as used herein, refers to an "$NR_pR_q$" group, wherein $R_p$ and $R_q$ can be alkyl, or cycloalkyl.

The term "alkoxy", as used herein, refers to an "alkyl-O—" group, wherein alkyl is defined above. Examples of alkoxy group include methoxy or ethoxy groups. The "alkyl" portion of alkoxy can be optionally substituted as described above with respect to alkyl.

The term "aryl," as used herein, refers to an aromatic monocyclic or polycyclic ring system consisting of carbon atoms. Thus, "$C_6$-$C_{18}$ aryl" is a monocyclic or polycyclic ring system containing from 6 to 18 carbon atoms. Examples of aryl groups include phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. An aryl can be optionally substituted with halogen, —OH, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{18}$ aryl, $C_6$-$C_{18}$ haloaryl, (5-20 atom) heteroaryl, —C(O)$C_1$-$C_3$ haloalkyl, —S(O)$_2$—, —$NO_2$, —CN, and oxo.

The terms "halogen," or "halo," as used herein, refer to fluorine, chlorine, bromine, or iodine.

The term "heterocyclyl," as used herein, refers to a non-aromatic ring having at least one heteroatom or a heteroaryl ring. containing one to four heteroatoms each selected from O, S, and N, wherein each heterocyclic group has from 4 to 10 atoms in its ring system. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the 25 total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. A heterocyclyl can be optionally substituted with the substituents listed above with respect to alkyl. Binding to a heterocycle can be at a heteroatom or via a carbon atom.

The term "heteroaryl," as used herein, refers a monocyclic or fused polycyclic aromatic ring containing one or more heteroatoms, such as oxygen, nitrogen, or sulfur. For example, a heteroaryl can be a "5-20 atom heteroaryl," which means a 5 to 20 membered monocyclic or fused polycyclic aromatic ring containing at least one heteroatom. Examples of heteroaryl groups include pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. A heteroaryl can be optionally substituted with the same substituents listed above with respect to aryl.

The term "haloalkyl," as used herein, includes an alkyl substituted with one or more of F, Cl, Br, or I, wherein alkyl is defined above. The "alkyl" portion of haloalkyl can be optionally substituted as described above with respect to alkyl.

The term "haloaryl," as used herein, includes an aryl substituted with one or more of F, Cl, Br, or I, wherein aryl is defined above. The "aryl" portion of haloaryl can be optionally substituted as described above with respect to aryl.

The term "oxo," as used herein, refers to =O.

The term "nitro," as used herein, refers to —NO$_2$.

"⁓" as used herein, refers to a point of attachment between two atoms.

In certain embodiments, linkers (also known as "linker molecules" or "cross-linkers" or "spacers") may be used to conjugate one atom to another in a composition. The majority of known linkers react with amine, carboxyl, and sulfhydryl groups. Linker molecules may be responsible for different properties of the composition. The length of the linker should be considered in light of molecular flexibility during the conjugation step, and the availability of the conjugated molecule for its target. Longer linkers may thus improve the biological activity of the compositions of the invention, as well as the ease of preparation of them. The geometry of the linker may be used to orient a molecule for optimal reaction with a target. A linker with flexible geometry may allow the entire composition to conformationally adapt as it binds a target sequence. The nature of the linker may be altered for other various purposes. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many premade linkers for use in conjugating molecules are commercially available from vendors such as Pierce Chemical Co., Roche Molecular Biochemicals, United States Biological. Exemplary linker molecules for use in the compositions of the invention include, but are not limited to: aminocaproic acid (ACA); polyglycine, and any other amino acid polymer, polymers such as polyethylene glycol (PEG), polymethyl methacrylate (PMMA), polypropylene glycol (PPG); homobifunctional reagents such as APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS; heterobifunctional reagents such as ABH, AEDP, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, MBuS, M2C2H, MPBH, MSA, NHS-ASA, PDPH, PMPI, SADP, SAED. SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS. Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS; and trifunctional linkers such as Sulfo-SBED.

Branched linkers may be prepared or used so that multiple moieties per linker are able to react. Such multiply reactive linkers allow the creation of multimeric binding sites.

The term "pKa," as used herein, includes the negative decadic logarithm of the ionization constant ($K_a$) of an acid; equal to the pH value at which equal concentrations of the acid and conjugate base forms of a substance (often a buffer) are present.

The term "hydrophobic," as used herein, refers to a compound that has an octanol/water partition coefficient ($K_{ow}$) greater than about 10 at about 23° C.

The term "hydrophilic," as used herein, refers to a compound that has an octanol/water partition coefficient ($K_{ow}$) less than about 10 at about 23° C.

A therapeutically effective amount can be achieved in the methods or compositions of the invention by co-administering a first amount of a first agent, for example a nucleic acid or an enzyme, and a second amount of at least one second agent, for example an anticancer agent or a second nucleic acid. In one embodiment, the two agents are each administered in a therapeutically effective amount (i.e., each in an amount which would be therapeutically effective if administered alone). In another embodiment, the first agent and the second agent are each administered in an amount which alone does not provide a therapeutic effect (a sub-therapeutic dose). In yet another embodiment, the first agent can be administered in a therapeutically effective amount, while the second agent is administered in a sub-therapeutic dose. In still another embodiment, the first agent can be administered in a sub-therapeutic dose, while the second agent is administered in a therapeutically effective amount. In example embodiment, the compositions exhibit enhanced therapeutic effect (synergy) compared to either the first agent or the second agent alone, or their expected additive effect.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline;

(xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) $C_2$-$C_{12}$ alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For formulations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a formulation described herein, depending on the administration route. The formulations described herein can be delivered via any administration mode known to a skilled practitioner. For example, the formulations described herein can be delivered in a systemic manner, via administration routes such as, but not limited to, oral, and parenteral including intravenous, intramuscular, intraperitoneal, intradermal, and subcutaneous. In some embodiments, the formulations described herein are in a form that is suitable for injection. In other embodiments, the formulations described herein are formulated for oral administration.

When administering parenterally, a formulation described herein can be generally formulated in a unit dosage injectable form (solution, suspension, emulsion). The formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g., PBS).

The formulations can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to formulations described herein, however, any vehicle, diluent, or additive used should have to be biocompatible with the active agents described herein. Those skilled in the art will recognize that the components of the formulations should be selected to be biocompatible with respect to the active agent. This will present no problem to those skilled in chemical and pharmaceutical principles, or problems can be readily avoided by reference to standard texts or by simple experiments (not involving undue experimentation).

For in vivo administration, the formulations described herein can be administered with a delivery device, e.g., a syringe. Accordingly, an additional aspect described herein provides for delivery devices comprising at least one chamber with an outlet, wherein the at least one chamber comprises a pre-determined amount of any formulation described herein and the outlet provides an exit for the formulation enclosed inside the chamber. In some embodiments, a delivery device described herein can further comprise an actuator to control release of the formulation through the outlet. Such delivery device can be any device to facilitate the administration of any formulation described herein to a subject, e.g., a syringe, a dry powder injector, a nasal spray, a nebulizer, or an implant such as a microchip, e.g., for sustained-release or controlled release of any formulation described herein.

The nomenclature used to define the peptides is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e. molecules that include both, an amino-attached hydrogen and a carbonyl carbon-attached hydroxyl) and residues of amino acids (i.e. molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

A protected amino acid is an amino acid in which one or more functional groups are protected with a protecting group. A protected peptide fragment is a dipeptide, tripeptide, or tetrapeptide, in which one or more functional groups of the amino acid of the peptide fragment are protected with a protecting group. Preferably, the protected amino acid and/or protected peptide fragment of the present invention have a protected amino group. The term "amino protecting group" refers to protecting groups which can be used to replace an acidic proton of an amino group in order to reduce its nucleophilicity.

Examples of amino protecting groups (e.g. $X^1$, $X^2$, $X^3$, $X^4$, etc.) include but are not limited to substituted or unsubstituted groups of acyl type, such as the formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methyl sulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group. Among these groups X, those comprising a carbonyl, a sulfenyl or a sulphonyl group are preferred. An amino protecting groups $X^1$, $X^2$, $X^3$, $X^4$, etc. is preferably selected from allyloxycarbonyl groups, tert-butyloxycarbonyl (BOC), benzyloxycarbonyl (Z), 9 fluorenylmethyloxycarbonyl (Fmoc), 4-nitrobenzenesulfonyl (Nosyl), 2-nitrobenzenesulfenyl (Nps) and substituted derivatives.

Preferred amino protecting groups $X^1$, $X^2$, $X^3$, $X^4$, etc. for the process of the present invention are tert-butyloxycarbonyl (Boc), a 9-fluorenylmethyloxycarbonyl (Fmoc), and a benzyloxy-carbonyl (Z). Even more preferred amino protecting groups for the process of the present invention are tert-butyloxycarbonyl (Boc) and a benzyloxy-carbonyl (Z).

Amino protecting groups $X^1$, $X^2$, $X^3$, $X^4$, etc. can be introduced by various methods as known in the art. For example, by reaction with suitable acid halides or acid anhydrides. On the other hand, amino protecting groups $X^1$, $X^2$, $X^3$, $X^4$, etc. can be removed (i.e., the step of deprotecting), for example, by acidolysis, hydrogenolysis (e.g., in the presence of hydrogen (e.g. bubbled through the liquid reaction medium) and catalyst such as palladium catalyst), treatment with dilute ammonium hydroxide, treatment with hydrazine, treatment with sodium and treatment with sodium amide.

As used herein, the term "peptide fragment" refers to two or more amino acids covalently linked by at least one amide bond (i.e. a bond between an amino group of one amino acid and a carboxyl group of another amino acid selected from the amino acids of the peptide fragment). The terms "polypeptide" and "peptide fragments" are used interchangeably. The term "peptide fragment" includes salts thereof, including pharmaceutically acceptable salts.

The term "DNA editing template," as used herein refers to an exogenous strand of DNA that bears homology arms to a section of genomic DNA that has been cut by a nuclease (CAS9, TALEN or zinc finger) along with an intervening sequence between these homology arms that differs with the natural segment of genomic DNA that has been cut. This intervening segment serves as the template for repair of the cut genomic DNA; and, in so doing, the cell corrects it own DNA to match that of the DNA template. The DNA template may be included in a single DNA expression vector that also encodes the nuclease.

The term "guide RNA," as used herein, includes an engineered, non-naturally occurring Clustered Regularly Interspaced Short Palindromic Repeats (CRISPR) guide RNA that hybridizes with a target nucleic acid sequence of interest.

The term "Cas9 mRNA," as used herein, includes a nucleotide sequence encoding a Type-II Cas9 protein.

The CRISPR-Cas system is useful for precise editing of genomic nucleic acids (e.g., for creating null mutations). In such embodiments, the CRISPR guide RNA and/or the Cas enzyme may be expressed. For example, a composition containing only the guide RNA can be administered to an animal or cells transgenic for the Cas9 enzyme. Similar strategies may be used (e.g., designer zinc finger, transcription activator-like effectors (TALEs) or homing meganucleases). Such systems are well known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326: 1509-1512; Moscou and Bogdanove (2009) *Science* 326: 1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47).

The CRISPR-Cas system is known in the art for incorporating transgenes. By "transgene" is meant any nucleotide sequence, particularly a DNA sequence, that is integrated into one or more chromosomes of a host cell by human intervention, such as by the methods of the present invention. In one embodiment, a transgene is an "RNA coding region." In another embodiment the transgene comprises a "gene of interest." In other embodiments the transgene may be a nucleotide sequence, preferably a DNA sequence, that is used to mark the chromosome where it has integrated or may indicate a position where nucleic acid editing, such as by the CRSPR-CAS system, may occur. In this situation, the transgene does not have to comprise a gene that encodes a protein that may be expressed.

A "gene of interest" is a nucleic acid sequence that encodes a protein or other molecule, such as an RNA or targeting nucleic acid sequence, that is desirable for integration in a host cell. The gene of interest may be a 1, 2, 3, 4, 5, 6, 7, 8, 9, 10, or more genes of interest.

Genes of interest are useful for modulating the expression and/or activity of target biomolecules either within the transduced cell or expressed for secretion outside of the transduced cell. Generally, genes of interest may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule such as a Piwi RNA, triplex oligonucleotide, ribozyme, coding sequence for a target of interest. Such agents modulate the expression and/or activity of target biomolecules, which includes any decrease in expression or activity of the target biomolecule of at least about 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more as compared to the expression or activity of the target biomolecule which has not been targeted by a modulating agent.

In one embodiment, the gene of interest is useful for overexpressing and/or enhancing the activity of a nucleic acid or protein of interest. For example, the gene of interest may encode a protein or other molecule the expression of which is desired in the host cell. Such protein-encoding nucleic acid sequences are not particularly limited and are selected based on the desired exogenous perturbation desired. Thus, the gene of interest includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The gene of interest encode a protein or be a nucleic acid that serves as a marker to identify cells of interest or transduced cells. The gene of interest may encode a protein that modifies a physical characteristic of the transduced cell, such as a protein that modifies size, growth, or eventual tissue composition. In another example, the gene of interest may encode a protein of commercial value that may be harvested. Generally, the gene of interest is operatively linked to other sequences that are useful for obtaining the desired expression of the gene of interest, such as transcriptional regulatory sequences like inducible promoters, as described further below.

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An "RNA coding region" is a nucleic acid that may serve as a template for the synthesis of an RNA molecule, such as an siRNA. "RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002) *J. Virol.* 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any number or range in between, of RNA inhibitory agents are transduced into cells of interest. Suitable inhibitory RNAs include, but are not limited to siRNAs, shRNAs, miRNAs, Piwis, dicer-substrate 27-mer duplexes, single-stranded interfering RNA, and the like. In particular, the combination of RNA inhibitory technology and lentiviruses as a tool for a gene specific knock-down in animal models is well known in the art (see, for example, U.S. Pat. Publ. 2005/0251872; EP Pat. Publ. 2166107; PCT Publs. WO 2004/022722 and 2007/109131; Tiscornia et al. (2003) *Proc. Natl. Acad. Sci. U.S.A.* 100: 1844-1848; Rubinson et al. (2003) *Nat. Genet.* 33:401-406; and Dann et al. (2006) *Proc. Natl. Acad. Sci. U.S.A.* 103: 11246-11251).

siRNAs typically refer to a double-stranded interfering RNA unless otherwise noted. In various embodiments, suitable siRNA molecules include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as "interfering RNAs" or "interfering RNA molecules."

Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinantly produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or more, or 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In various embodiments one or both strands of the interfering RNAs may comprise a 3' overhang. As used herein, a "3'overhang" refers to at least one unpaired nucleotide extending from the 3'-end of an RNA strand. Thus in one embodiment, the interfering RNAs comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length. In an illustrative embodiment in which both strands of the interfering RNAs molecule comprise a 3' overhang, wherein the length of the overhangs may be the same or different for each strand. In certain embodiments the 3' overhang is present on both strands of the interfering RNAs and is one, two, or three nucleotides in length. For example, each strand of the interfering RNAs may comprise 3' overhangs of dithymidylic acid ("TT") or diuridylic acid ("uu").

In order to enhance the stability of the interfering RNAs, the 3' overhangs may be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNA interference degradation. In particular, it is believed the absence of a 2' hydroxyl in the 2'-deoxythymidine may significantly enhance the nuclease resistance of the 3' overhang.

Interfering RNAs may be expressed from a composition described herein either as two separate, complementary RNA molecules, or as a single RNA molecule with two complementary regions.

In certain embodiments, the interfering RNAs may be delivered as a small hairpin RNA or short hairpin RNA (shRNA) (see, for example, U.S. Pat. Nos. 8,697,359 and 8,642,569). shRNA is a sequence of RNA that makes a tight hairpin turn that may be used to silence gene expression via RNA interference. The shRNA hairpin structure is cleaved by the cellular machinery into siRNA, which is then bound to the RNA-induced silencing complex (RISC). This complex binds to and cleaves mRNAs that match the siRNA that is bound to it.

In certain embodiments, the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, 6, 7, 8, 9, 10, 11, 12, 13, 14, 15, 16, 17, 18, and 19 nucleotides) in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. Thus, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule may also comprise a 5'-terminal phosphate group that may be chemically modified. In addition, the loop portion of the shRNA molecule may comprise, for example, nucleotides, non-nucleotides, linker molecules, conjugate molecules, etc.

In certain embodiments, the PIWI RNA pathway is used to provide inhibition of target biomolecules. Piwi-interacting RNAs (piRNAs) were identified through association with Piwi proteins in mammalian testes (Aravin et al. (2006); Girard et al. (2006); Grivna et al. (2006); Lau et al. (2006). piRNAs and methods of making and using same to target and degrade nucleic acids are well known in the art (see, for example, U.S. Pat. Publ. 2011-0207625). These RNAs range from 26-30 nucleotides in length and are produced from discrete loci. Generally, genomic regions spanning 50-100 kB in length give rise to abundant piRNAs with profound strand asymmetry. Although the piRNAs themselves are not conserved, even between closely related species, the positions of piRNA loci in related genomes are conserved, with virtually all major piRNA-producing loci having syntenic counterparts in mice, rats and humans (Girard et al. (2006)). The loci and consequently the piRNAs themselves are relatively depleted of repeat and transposon sequences, with only 17% of human piRNAs corresponding to known repetitive elements as compared to a nearly 50% repeat content for the genome as a whole. In certain embodiments, methods are provided for inhibiting such targets in a cell, comprising administering an effective amount of a siRNA/shRNA/piwiRNA to the cell, such that target mRNA is degraded.

As described below, internal promoters may also be included in order to allow for the independent expression of more than one gene of interest. If a second or additional gene of interest is included, an internal ribosomal entry site (IRES) sequence may be included (see, for example, U.S. Pat. No. 4,937,190). The IRES sequence may facilitate the expression of the reporter gene and may be used to create multigene, or polycistronic, messages. IRES elements are able to bypass the ribosome scanning model of 5'-methylated cap-dependent translation and begin translation at internal sites (Pelletier and Sonenberg, 1988). IRES elements are well known in the art and be isolated from, for example, at least two members of the picornavirus family (polio and encephalomyocarditis) have been described (Pelletier and Sonenberg, 1988), as well as from a mammalian message (Macejak and Sarnow, 1991). IRES elements may be linked to heterologous open reading frames. Multiple open reading frames may be transcribed together, each separated by an IRES, creating polycistronic messages. By virtue of the IRES element, each open reading frame is accessible to ribosomes for efficient translation. Multiple genes may be efficiently expressed using a single promoter/enhancer to transcribe a single message.

In certain embodiments of the invention, cells transduced with the delivery systems of the present invention may be identified in vitro or in vivo by including a marker in the sequence. Such markers would confer an identifiable change to the transduced cell permitting easy identification of cells containing the marker. For example, a gene of interest encoding a marker protein may be placed after the primary gene of interest that is, for example, an RNA interfering nucleic acid, to allow for identification of cells that are expressing the desired protein.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Many useful reporter markers are known and include, for example, a fluorescence marker, preferably selected from green fluorescent protein (GFP), enhanced GFP (eGFP), DsRed, AsRed, HcRed, Tomatoe, Cherry, Katushka, and variants thereof (see, for example, U.S. Pat. Nos. 5,487,932 and 5,464,763). Examples of other useful reporters include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

The term "alkylating agent," as used herein, means a compound that is able to transfer alkyl groups to DNA. Alkylation can result in miscoding of DNA strands, incomplete repair of alkylated segments (which leads to strand breakage or depurination), excessive cross-linking of DNA, and inhibition of strand separation at mitosis. Monofunctional alkylating agents transfer a single alkyl group and usually result in miscoding of DNA, strand breakage, or depurination. These reactions can result in cell death, mutagenesis, or carcinogenesis. Polyfunctional alkylating agents typically cause strand cross-linking and inhibition of mitosis with consequent cell death. Resistance to one alkylating agent often implies resistance to other drugs in the same class and can be caused by increased production of nucleophilic substances that compete with the target DNA for alkylation. Decreased permeation of alkylating agents and increased activity of DNA repair systems are also common mechanisms of resistance.

Individual alkylating agents are generally cell-cycle nonspecific and can be subgrouped according to chemical structure into nitrogen mustards, ethyleneamines, alkyl sulfonates, nitrosoureas, and triazene derivatives.

The most common subgroup of alkylating agents used is the nitrogen mustard group. Mechlorethamine hydrochloride is the prototype of the nitrogen mustards and is commonly used in veterinary medicine to treat lymphoma in conjunction with other chemotherapeutics. Because of the highly unstable nature and extremely short duration of action of mechlorethamine, its use is somewhat limited in veterinary medicine. Derivatives of mechlorethamine commonly used for various neoplasias include cyclophosphamide, chlorambucil, and melphalan.

Cyclophosphamide is a cyclic phosphamide derivative of mechlorethamine that requires metabolic activation by the cytochrome P450 oxidation system in the liver. Cyclophosphamide is given PO or IV, and dose-limiting leukopenia associated with bone marrow suppression is the primary toxicity. However, among the alkylating chemotherapy agents, the myelosuppressive effect of cyclophosphamide is considered relatively sparing of platelets and progenitor cells. Sterile hemorrhagic cystitis may result from aseptic chemical inflammation of the bladder urothelium caused by acrolein, a metabolite of cyclophosphamide. Prevention of this toxicity is key to its management. Specifically, concurrent administration of a diuretic, such as furosemide, may be used when cyclophosphamide is given as a single dose to provide a dilutional effect. In addition, cyclophosphamide may be given in the morning so that patients can be provided several opportunities to urinate throughout the day to minimize contact time of acrolein with the bladder lining. In patients with evidence of sterile hemorrhagic cystitis, cyclophosphamide use should be discontinued. Although the signs may be self-limiting, treatment with fluids, NSAIDs, methylsulfonylmethane (MSM), and intravesicular DMSO may be considered. Mesna is a drug that binds and inactivates the urotoxic metabolites of cyclophosphamide within the bladder. Mesna coadministered with fluid diuresis is recommended when ifosfamide (an analogue of cyclophosphamide) or high-dose cyclophosphamide is used.

Chlorambucil, the slowest-acting nitrogen mustard, achieves effects gradually and often can be used in animals with compromised bone marrow. It can cause bone marrow suppression, which is usually mild; however, periodic monitoring is recommended with longterm administration. This drug is given PO and is most commonly used in treatment of chronic, well-differentiated cancers; it is considered ineffective in rapidly proliferating tumors.

Melphalan, an L-phenylalanine derivative of mechlorethamine, is given PO or IV and is primarily used in veterinary medicine to treat multiple myeloma.

Of the other subgroups of alkylating agents, several have limited but specific uses. Triethylenethiophosphoramide (thiotepa), an ethylenimine, has been reported as an intravesicular treatment for transitional cell carcinoma of the bladder or as an intracavitary treatment for pleural and peritoneal effusions. Busulfan, an alkyl sulfonate, is used specifically in treatment of chronic myelocytic leukemia and polycythemia vera. Streptozotocin, a naturally occurring nitrosourea, is used for palliation of malignant pancreatic islet-cell tumors or insulinomas. Other nitrosoureas, such as carmustine and lomustine, readily cross the blood-brain barrier and have been useful in management of lymphoma (including epitheliotropic cutaneous lymphoma), mast cell tumors, histiocytic sarcomas, and CNS neoplasias. Dacarbazine (DTIC), a triazene derivative, has been used either in combination with doxorubicin or as a single-agent treatment for relapsed canine lymphoma and soft-tissue sarcomas.

Temozolomide is an oral imidazotetrazine derivative of dacarbazine and belongs to a class of chemotherapeutic agents that enter the CSF and do not require hepatic metabolism for activation. In people, it is used for refractory malignant gliomas and malignant melanomas. There have been reports in the veterinary literature of its use as a substitute for dacarbazine (DTIC).

Exemplary Compositions for CRISPR Delivery

In certain embodiments, the invention relates to a composition comprising, consisting essentially of, or consisting of:
an agent, wherein the agent is (a) a nuclease selected from the group consisting of Cas9, TALEN, and zinc finger, or (b) a nucleic acid encoding a nuclease selected from the group consisting of Cas9, TALEN, and zinc finger;
an optional pharmaceutically acceptable carrier;
an optional DNA editing template; and a block copolymer comprising:
(i) a first block comprising a plurality of first monomers, wherein each first monomer is hydrophilic;
(ii) a second block comprising a plurality of second monomers, wherein each second monomer is hydrophobic; and
(iii) a third block comprising a plurality of third monomers, wherein each third monomer is positively charged at a pH from about 6.8 to about 7.4,
wherein
the agent is non-covalently associated with the block copolymer; and
the DNA editing template, when present, is non-covalently associated with the block copolymer.

In certain embodiments, the invention relates to any of the compositions described herein, wherein the agent is Cas9 or a nucleic acid encoding Cas9; and a guide nucleic acid non-covalently associated with the block copolymer.

In certain embodiments, the invention relates to a composition comprising, consisting essentially of, or consisting of:
an optional pharmaceutically acceptable carrier;
a Cas9 mRNA;
a guide RNA; and
a block copolymer comprising:
(i) a first block comprising a plurality of first monomers, wherein each first monomer is hydrophilic;
(ii) a second block comprising a plurality of second monomers, wherein each second monomer is hydrophobic; and
(iii) a third block comprising a plurality of third monomers, wherein each third monomer is positively charged at a pH from about 6.8 to about 7.4,
wherein
the Cas9 mRNA is non-covalently associated with the block copolymer; and
the guide RNA is non-covalently associated with the block copolymer.

In certain embodiments, the invention relates to any of the compositions described herein, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin.

In certain embodiments, the invention relates to any of the compositions described herein, wherein each first monomer is ethylene glycol.

In certain embodiments, the invention relates to any of the compositions described herein, wherein the second block is a polyester, a polyanhydride, a polypeptide, or a polycarbonate, a poly(acetal), a poly(amide), a poly(amide ester), a poly(ester ether), a poly(ester urethane), a poly(ether), a poly(hydroxyl alkanoate), a poly(nucleic acid), a poly(ortho ester), a poly(phosphazene), a poly(phosphoester), a poly(saccharide), or a poly(urethane).

In certain embodiments, the invention relates to any of the compositions described herein, wherein the second block is a polyester, a polyanhydride, a polypeptide, or a polycarbonate.

In certain embodiments, the invention relates to any of the compositions described herein, wherein the second block is a polyester.

In certain embodiments, the invention relates to any of the compositions described herein, wherein the second block is a poly($\alpha$-ester).

In certain embodiments, the invention relates to any of the compositions described herein, wherein the second block is poly(lactic-co-glycolic acid) (PLGA), poly(3-hydroxybutyrate), or poly (trimethylene carbonate) (PTMC).

In certain embodiments, the invention relates to any of the compositions described herein, wherein the second block is a polypeptide.

In certain embodiments, the invention relates to any of the compositions described herein, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate.

In certain embodiments, the invention relates to any of the compositions described herein, wherein each second monomer has the structure of Formula II:

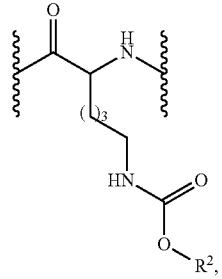

Formula II wherein
$R^2$ is $C_1$-$C_6$alkyl, $C_3$-$C_6$alkenyl, $C_5$-$C_{22}$carbocyclyl-substituted $C_1$-$C_6$alkyl, or 5-22-membered heterocyclyl-substituted $C_1$-$C_6$alkyl.

In certain embodiments, the invention relates to any of the compositions described herein, wherein $R^2$ is benzyl.

In certain embodiments, the invention relates to any of the compositions described herein, wherein each third monomer comprises a —$NHR_2^+$ functionality at pH about 7, wherein R is H or $C_1$-$C_6$ alkyl.

In certain embodiments, the invention relates to any of the compositions described herein, wherein each third monomer is selected from the group consisting of lysine, arginine, asparagine, side-chain aminoalkyl-functionalized asparagine, aspartamide, side-chain aminoalkyl-functionalized aspartamide, and ethyleneimine.

In certain embodiments, the invention relates to any of the compositions described herein, wherein each third monomer has the structure of Formula III or Formula IV:

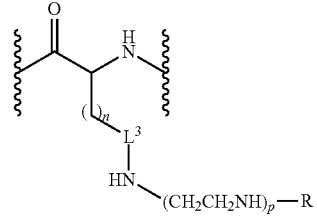

Formula III

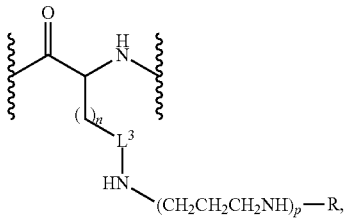

Formula IV wherein
$L^3$ is a bond or —C(=O)—;
p is 1, 2, or 3;
R is H or $C_1$-$C_6$alkyl; and
n is 1, 2, 3, 4, 5, or 6.

In certain embodiments, the invention relates to any of the compositions described herein, wherein n is 1 or 2.

In certain embodiments, the invention relates to any of the compositions described herein, wherein n is 1.

In certain embodiments, the invention relates to any of the compositions described herein, wherein $L^3$ is —C(=O)—.

In certain embodiments, the invention relates to any of the compositions described herein, wherein R is H.

In certain embodiments, the invention relates to any of the compositions described herein, wherein p is 2.

In certain embodiments, the invention relates to any of the compositions described herein, wherein the block copolymer has the following structure:

$A^1$-(first block)-$L^1$-(second block)-$L^2$-(third block)-$A^2$ wherein
$A^1$ is OH or —O—($C_1$-$C_6$)alkyl;
$A^2$ is H, an amine protecting group, or an amino acid;
$L^1$ is a covalent bond or a first linker; and
$L^2$ is a covalent bond or a second linker.

In certain embodiments, the invention relates to any of the compositions described herein, wherein $A^1$ is —O—($C_1$-$C_6$)alkyl.

In certain embodiments, the invention relates to any of the compositions described herein, wherein $A^1$ is —$OCH_3$.

In certain embodiments, the invention relates to any of the compositions described herein, wherein $A^2$ is H.

In certain embodiments, the invention relates to any of the compositions described herein, wherein $L^1$ is a first linker.

In certain embodiments, the invention relates to any of the compositions described herein, wherein $L^1$ is —$C_1$-$C_6$alkylene-NR—; and R is H or $C_1$-$C_6$alkyl.

In certain embodiments, the invention relates to any of the compositions described herein, wherein $L^2$ is —$CH_2CH_2$—NH—.

In certain embodiments, the invention relates to any of the compositions described herein, wherein $L^2$ is a covalent bond.

In certain embodiments, the invention relates to any of the compositions described herein, wherein the block copolymer comprises from about 3 to about 60 contiguous second monomers.

In certain embodiments, the invention relates to any one of the compositions described herein, wherein the copolymer comprises from about 10 to about 40 contiguous second repeat units. In certain embodiments, the invention relates to any one of the compositions described herein, wherein the copolymer comprises from about 15 to about 35 contiguous second repeat units. In certain embodiments, the invention relates to any one of the compositions described herein, wherein the copolymer comprises about 15, about 16, about 17, about 18, about 19, about 20, about 21, about 22, about 23, about 24, about 25, about 26, about 27, about 28, about 29, about 30, about 31, about 32, about 33, about 34, or about 35 contiguous second repeat units.

In certain embodiments, the invention relates to any of the compositions described herein, wherein the block copolymer comprises from about 10 to about 60 contiguous third monomers.

In certain embodiments, the invention relates to any one of the compositions described herein, wherein the copolymer comprises from about 60 to about 180 contiguous third repeat units. In certain embodiments, the invention relates to any one of the compositions described herein, wherein the copolymer comprises from about 80 to about 160 contiguous third repeat units. In certain embodiments, the invention relates to any one of the compositions described herein, wherein the copolymer comprises about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, or about 140 contiguous third repeat units.

In certain embodiments, the invention relates to any of the compositions described herein, wherein the block copolymer comprises from about 40 to about 300 contiguous first monomers.

In certain embodiments, the invention relates to any one of the compositions described herein, wherein the block copolymer comprises from about 3 to about 40 contiguous first monomers. In certain embodiments, the invention relates to any one of the compositions described herein, wherein the copolymer comprises from about 4 to about 30 contiguous first repeat units. In certain embodiments, the invention relates to any one of the compositions described herein, wherein the copolymer comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 contiguous first repeat units.

In certain embodiments, the invention relates to any of the compositions described herein, wherein the block copolymer is MPEG-b-PCL-b-PLL.

In certain embodiments, the invention relates to any of the compositions described herein, wherein the block copolymer is wherein
x is from about 40 to about 300;
y is from about 3 to about 60; and
z is from about 10 to about 60.

In certain embodiments, the invention relates to any of the compositions described herein, wherein the guide RNA is sgRNA.

In certain embodiments, the invention relates to any of the compositions described herein, wherein the Cas9 mRNA and guide RNA are in the form of a CRISPR Cas9 plasmid.

In certain embodiments, the invention relates to any of the compositions described herein, wherein the composition further comprises a DNA repair template non-covalently associated with the block copolymer.

In certain embodiments, the invention relates to any of the compositions described herein, wherein the DNA repair template is a ssDNA repair template.

In certain embodiments, the invention relates to any of the compositions described herein, wherein the composition further comprises a second block copolymer non-covalently associated with the block copolymer.

In certain embodiments, the invention relates to any of the compositions described herein, wherein the second block copolymer is a diblock copolymer.

In certain embodiments, the invention relates to any of the compositions described herein, wherein the second block copolymer comprises a fourth block comprising a plurality of fourth monomers, and a fifth block comprising a plurality of first monomers.

In certain embodiments, the invention relates to any of the compositions described herein, wherein each fourth monomer has a pKa less than or equal to about 6 in water.

In certain embodiments, the invention relates to any of the compositions described herein, wherein at least one fourth monomer comprises a —$CO_2^-$ functionality at pH about 7.

In certain embodiments, the invention relates to any of the compositions described herein, wherein each fourth monomer is selected from the group consisting of aspartic acid, glutamic acid, glycolic acid, acrylic acid, and methacrylic acid.

In certain embodiments, the invention relates to any of the compositions described herein, wherein the second block copolymer comprises from about 5 to about 240 contiguous fourth monomers.

In certain embodiments, the invention relates to any of the compositions described herein, wherein the mole ratio of fourth monomer to third monomer in the composition is from about 1:1 to about 5:1.

In certain embodiments, the invention relates to any of the compositions described herein, wherein the composition further comprises an anticancer agent.

In certain embodiments, the invention relates to any of the compositions described herein, wherein the anticancer agent is covalently bound to the block copolymer.

In certain embodiments, the invention relates to any of the compositions described herein, wherein the anticancer agent is an alkylating agent or a nucleic acid cross-linking agent.

In certain embodiments, the invention relates to any of the compositions described herein, wherein the anticancer agent is an alkylating agent.

In certain embodiments, the invention relates to any of the compositions described herein, wherein the anticancer agent is a nucleic acid cross-linking agent.

In certain embodiments, the invention relates to any of the compositions described herein, wherein the anticancer agent comprises Pt(II) or Pt(IV).

In certain embodiments, the invention relates to any of the compositions described herein, wherein the anticancer agent is covalently bound to at least one third monomer.

In certain embodiments, the invention relates to any of the compositions described herein, wherein at least one third monomer has the structure of Formula I:

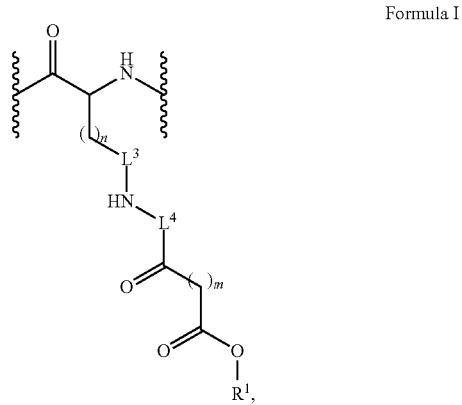

Formula I wherein
 $R^1$ comprises the anticancer agent;
 $L^3$ is a bond or —C(=O)—;
 $L^4$ is a bond or [—($C_1$-$C_6$)alkylene-NR-]$_p$;
 p is 1, 2, or 3;
 R is H or $C_1$-$C_6$alkyl;
 n is 1, 2, 3, 4, 5, or 6; and
 m is 1, 2, 3, 4, 5, or 6.

In certain embodiments, the invention relates to any of the compositions described herein, wherein the anticancer agent is a nucleic acid cross-linking agent.

In certain embodiments, the invention relates to any of the compositions described herein, wherein the anticancer agent comprises Pt(II) or Pt(IV).

In certain embodiments, the invention relates to any of the compositions described herein, wherein the anticancer agent comprises Pt(IV).

In certain embodiments, the invention relates to any of the compositions described herein, wherein $R^1$ is

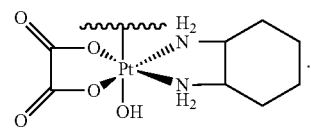

In certain embodiments, the invention relates to any of the compositions described herein, wherein the anticancer agent is a moiety represented by the structural formula:

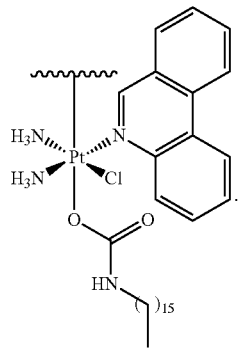

In certain embodiments, the invention relates to any of the compositions described herein, wherein n is 3, 4, or 5.

In certain embodiments, the invention relates to any of the compositions described herein, wherein n is 4.

In certain embodiments, the invention relates to any of the compositions described herein, wherein m is 1, 2, or 3.

In certain embodiments, the invention relates to any of the compositions described herein, wherein m is 2.

In certain embodiments, the invention relates to any of the compositions described herein, wherein $L^3$ is a bond.

In certain embodiments, the invention relates to any of the compositions described herein, wherein $L^3$ is —C(=O)—.

In certain embodiments, the invention relates to any of the compositions described herein, wherein $L^4$ is a bond.

In certain embodiments, the invention relates to any of the compositions described herein, wherein $L^4$ is [—(C$_1$-C$_6$)alkylene-NR-]$_p$.

In certain embodiments, the invention relates to any of the compositions described herein, wherein $L^4$ is [—(CH$_2$CH$_2$)—NR-]$_2$.

In certain embodiments, the invention relates to any of the compositions described herein, wherein R is H.

In certain embodiments, the invention relates to any of the compositions described herein, wherein the anticancer agent is non-covalently associated with the block copolymer.

In certain embodiments, the invention relates to any of the compositions described herein, wherein the anticancer agent is an alkylating agent or a nucleic acid cross-linking agent.

In certain embodiments, the invention relates to any of the compositions described herein, wherein the anticancer agent is an alkylating agent.

In certain embodiments, the invention relates to any of the compositions described herein, wherein the anticancer agent is a nucleic acid cross-linking agent.

In certain embodiments, the invention relates to any of the compositions described herein, wherein the anticancer agent comprises Pt(II) or Pt(IV).

In certain embodiments, the invention relates to any of the compositions described herein, wherein the anticancer agent comprises Pt(II).

In certain embodiments, the invention relates to any of the compositions described herein, wherein the pharmaceutically acceptable carrier is an aqueous liquid.

In certain embodiments, the invention relates to any of the compositions described herein, wherein the aqueous liquid comprises a buffer.

In certain embodiments, the invention relates to any one of the compositions described herein, wherein the buffer is selected from the group consisting of: N-(2-acetamido)-2-aminoethanesulfonic acid (aces), N-(2-acetamido)iminodiacetic acid (ADA), acetate, 2-amino-2-methyl-1,3-propanediol (AMPD), 2-amino-2-methyl-1-propanol (AMP), N,N-bis(2-hydroxyethyl)-2-aminoethanesulfonic acid (BES), 3-(N,N-bis[2-hydroxyethyl]amino)-2-hydroxypropanesulfonic acid (DIPSO), N,N-bis(2-hydroxyethyl)glycine (Bicine), bis(2-hydroxyethyl)iminotris(hydroxymethyl)methane (Bis-Tris), 1,3-bis[tris(hydroxymethyl)methylamino]propane (Bis-Tris propane), borate, citrate, 4-(cyclohexylamino)-1-butanesulfonic acid (CABS), 2-(cyclohexylamino)ethanesulfonic acid (CHES), 3-(cyclohexylamino)-2-hydroxy-1-propanesulfonic acid (CAPSO), 3-(cyclohexylamino)-1-propanesulfonic acid (CAPS), diglycine (Gly-Gly), 3-([1,1-dimethyl-2-hydroxyethyl]amino)-2-hydroxypropanesulfonic acid (AMPSO), glycine, 2-[(2-hydroxy-1,1-bis[hydroxymethyl]ethyl)amino]ethanesulfonic acid (TES), N-(2-hydroxyethyl)piperazine-N'-(4-butanesulfonic acid) (HEPBS), N-(2-hydroxyethyl)-piperazine-N'-ethanesulfonic acid (HEPES), 4-(2-hydroxyethyl)-1-piperazinepropanesulfonic acid (EPPS), 4-(N-morpholino)butanesulfonic acid (MOBS), 2-(N-morpholino)ethanesulfonic acid (MES), 3-(N-morpholino)propanesulfonic acid (MOPS), 3-(N-morpholinyl)-2-hydroxypropanesulfonic acid (MOPSO), phosphate, piperazine-N,N'-bis(2-hydroxypropanesulfonic acid) (POPSO), 1,4-piperazinediethanesulfonic acid (PIPES), tris(hydroxymethyl)aminomethane (Tris), 3-(N-tris[hydroxymethyl]methylamino)-2-hydroxypropanesulfonic acid (TAPSO), N-tris(hydroxymethyl)methyl-3-aminopropanesulfonic acid (TAPS), and N-[tris(hydroxymethyl)methyl]glycine (Tricine).

In certain embodiments, the invention relates to any one of the compositions described herein, wherein the concentration of buffer in the aqueous liquid is about 10 mM to about 100 mM.

In certain embodiments, the invention relates to any one of the compositions described herein, wherein the concentration of buffer in the aqueous liquid is about 20 mM, about 30 mM, about 40 mM, about 50 mM, about 60 mM, about 70 mM, about 80 mM, or about 90 mM.

In certain embodiments, the invention relates to any one of the compositions described herein, wherein the concentration of buffer in the aqueous liquid is about 50 mM.

In certain embodiments, the invention relates to any one of the compositions described herein, wherein the pH of the aqueous liquid is about 6.5, about 7.0, about 7.5, about 8.0, about 8.5, about 9.0, or about 9.5.

In certain embodiments, the invention relates to any of the compositions described herein, wherein the pH of the aqueous liquid is about 6.8 to about 7.4.

In certain embodiments, the invention relates to any one of the compositions described herein, wherein the pH of the aqueous liquid is about 7.0.

In certain embodiments, the invention relates to any of the compositions described herein, wherein the block copolymer is in the form of a micelle when in an aqueous liquid.

In certain embodiments, the invention relates to any of the compositions described herein, wherein the average diameter of the micelles, as determined by DLS, is about 20 nm to about 160 nm.

In certain embodiments, the invention relates to any one of the compositions described herein, wherein the average diameter of the micelles, as determined by DLS, is about 80 nm, about 90 nm, about 100 nm, about 110 nm, or about 120 nm.

In certain embodiments, the invention relates to any one of the compositions described herein, wherein the temperature of the composition is about 18° C. to about 50° C.

In certain embodiments, the invention relates to any one of the compositions described herein, wherein the temperature of the composition is about 20° C., about 22° C., about 24° C., about 26° C., about 28° C., about 30° C., about 32° C., about 34° C., about 36° C., about 38° C., about 40° C., about 42° C., about 44° C., about 46° C., or about 48° C.

In certain embodiments, the invention relates to any one of the compositions described herein, wherein the temperature of the composition is about 23° C.

In certain embodiments, the invention relates to any one of the compositions described herein, wherein the temperature of the composition is about 37° C.

In certain embodiments, the invention relates to any one of the compositions described herein, wherein the block copolymer does not comprise polyhistidine.

Exemplary Block Copolymers

In certain embodiments, the invention relates to a block polymer having the structure:

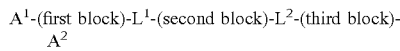

A$^1$-(first block)-L$^1$-(second block)-L$^2$-(third block)-A$^2$ wherein the first block comprises a plurality of first monomers; each first monomer is selected from the group consisting of ethylene glycol, propylene glycol, and vinyl alcohol;

the second block comprises a plurality of second monomers; each second monomer is side-chain N-protected lysine;

the third block comprises a plurality of third monomers; each third monomer is selected from the group consisting of arginine, lysine, side-chain aminoalkyl-functionalized asparagine, and side-chain aminoalkyl-functionalized aspartamide;

A$^1$ is OH or —O—(C$_1$-C$_6$)alkyl;

A$^2$ is H, an amine protecting group, or an amino acid;

L$^1$ is a covalent bond or a first linker; and

L$^2$ is a covalent bond or a second linker.

In certain embodiments, the invention relates to any of the block copolymers described herein, wherein each first monomer is ethylene glycol.

In certain embodiments, the invention relates to any of the block copolymers described herein, wherein each second monomer has the structure of Formula II:

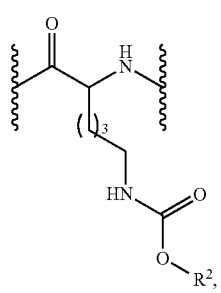

Formula II wherein

R$^2$ is C$_1$-C$_6$alkyl, C$_3$-C$_6$alkenyl, C$_5$-C$_{22}$carbocyclyl-substituted C$_1$-C$_6$alkyl, or 5-22-membered heterocyclyl-substituted C$_1$-C$_6$alkyl.

In certain embodiments, the invention relates to any of the block copolymers described herein, wherein R$^2$ is benzyl.

In certain embodiments, the invention relates to any of the block copolymers described herein, wherein each third monomer has the structure of Formula III or Formula IV:

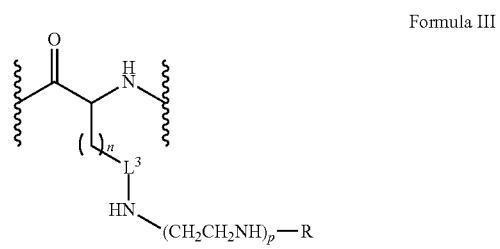

Formula III

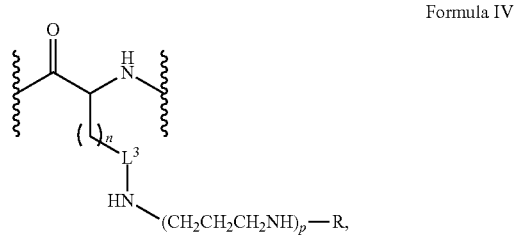

Formula IV wherein

L$^3$ is a bond or —C(=O)—;

p is 1, 2, or 3;

R is H or C$_1$-C$_6$alkyl; and n is 1, 2, 3, 4, 5, or 6.

In certain embodiments, the invention relates to any of the block copolymers described herein, wherein n is 1 or 2.

In certain embodiments, the invention relates to any of the block copolymers described herein, wherein n is 1.

In certain embodiments, the invention relates to any of the block copolymers described herein, wherein L$^3$ is —C(=O)—.

In certain embodiments, the invention relates to any of the block copolymers described herein, wherein R is H.

In certain embodiments, the invention relates to any of the block copolymers described herein, wherein p is 2.

In certain embodiments, the invention relates to any of the block copolymers described herein, wherein A$^1$ is —O—(C$_1$-C$_6$)alkyl.

In certain embodiments, the invention relates to any of the block copolymers described herein, wherein A$^1$ is —OCH$_3$.

In certain embodiments, the invention relates to any of the block copolymers described herein, wherein A$^2$ is H.

In certain embodiments, the invention relates to any of the block copolymers described herein, wherein L$^1$ is a first linker.

In certain embodiments, the invention relates to any of the block copolymers described herein, wherein L$^1$ is —C$_1$-C$_6$alkylene-NR—; and R is H or C$_1$-C$_6$alkyl.

In certain embodiments, the invention relates to any of the block copolymers described herein, wherein L$^1$ is —CH$_2$CH$_2$—NH—.

In certain embodiments, the invention relates to any of the block copolymers described herein, wherein L$^2$ is a covalent bond.

In certain embodiments, the invention relates to any of the block copolymers described herein, wherein the block copolymer comprises from about 40 to about 300 contiguous first monomers.

In certain embodiments, the invention relates to any of the block copolymers described herein, wherein the block copolymer comprises from about 3 to about 60 contiguous second monomers.

In certain embodiments, the invention relates to any of the block copolymers described herein, wherein the block copolymer comprises from about 10 to about 60 contiguous third monomers.

In certain embodiments, the invention relates to any of the block copolymers described herein, wherein the block copolymer is

[Chemical structure shown]

wherein
x is from about 40 to about 300;
y is from about 3 to about 60; and
z is from about 10 to about 60.

Exemplary Core Copolymer/Shell Copolymer Compositions

In certain embodiments, the invention relates to a composition comprising, consisting essentially of, or consisting of:
- a pharmaceutically acceptable carrier;
- a first block copolymer comprising:
  (i) a first block comprising a plurality of first monomers, wherein each first monomer is hydrophilic;
  (ii) a second block comprising a plurality of second monomers, wherein each second monomer is hydrophobic; and
  (iii) a third block comprising a plurality of third monomers, wherein each third monomer is positively charged at a pH from about 6.8 to about 7.4; and
- a second block copolymer comprising:
  (i) a fourth block comprising a plurality of fourth monomers, wherein each fourth monomer has a pKa less than or equal to about 6 in water; and
  (ii) a fifth block comprising a plurality of first monomers,
    wherein the second block copolymer is non-covalently associated with the first block copolymer.

In certain embodiments, the invention relates to any of the compositions described herein, wherein at least one fourth monomer comprises a $-CO_2^-$ functionality at pH about 7.

In certain embodiments, the invention relates to any of the compositions described herein, wherein each fourth monomer is selected from the group consisting of aspartic acid, glutamic acid, glycolic acid, acrylic acid, and methacrylic acid.

In certain embodiments, the invention relates to any of the compositions described herein, wherein the second block copolymer comprises from about 5 to about 240 contiguous fourth monomers.

In certain embodiments, the invention relates to any of the compositions described herein, wherein the mole ratio of fourth monomer to third monomer in the composition is from about 1:1 to about 5:1

In certain embodiments, the invention relates to any of the compositions described herein, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin.

In certain embodiments, the invention relates to any of the compositions described herein, wherein each first monomer is ethylene glycol.

In certain embodiments, the invention relates to any of the compositions described herein, wherein the second block is a polyester, a polyanhydride, a polypeptide, or a polycarbonate, a poly(acetal), a poly(amide), a poly(amide ester), a poly(ester ether), a poly(ester urethane), a poly(ether), a poly(hydroxyl alkanoate), a poly(nucleic acid), a poly(ortho ester), a poly(phosphazene), a poly(phosphoester), a poly(saccharide), or a poly(urethane).

In certain embodiments, the invention relates to any of the compositions described herein, wherein the second block is a polyester, a polyanhydride, a polypeptide, or a polycarbonate.

In certain embodiments, the invention relates to any of the compositions described herein, wherein the second block is a polyester.

In certain embodiments, the invention relates to any of the compositions described herein, wherein the second block is a poly(α-ester).

In certain embodiments, the invention relates to any of the compositions described herein, wherein the second block is poly(lactic-co-glycolic acid) (PLGA), poly(3-hydroxybutyrate), or poly (trimethylene carbonate) (PTMC).

In certain embodiments, the invention relates to any of the compositions described herein, wherein the second block is a polypeptide.

In certain embodiments, the invention relates to any of the compositions described herein, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate.

In certain embodiments, the invention relates to any of the compositions described herein, wherein each second monomer has the structure of Formula II:

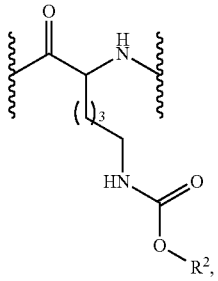

Formula II wherein
R$^2$ is C$_1$-C$_6$alkyl, C$_3$-C$_6$alkenyl, C$_5$-C$_{22}$carbocyclyl-substituted C$_1$-C$_6$alkyl, or 5-22-membered heterocyclyl-substituted C$_1$-C$_6$alkyl.

In certain embodiments, the invention relates to any of the compositions described herein, wherein R$^2$ is benzyl.

In certain embodiments, the invention relates to any of the compositions described herein, wherein each third monomer comprises a —NHR$_2^+$ functionality at pH about 7, wherein R is H or C$_1$-C$_6$ alkyl.

In certain embodiments, the invention relates to any of the compositions described herein, wherein each third monomer is selected from the group consisting of lysine, arginine, asparagine, side-chain aminoalkyl-functionalized asparagine, aspartamide, side-chain aminoalkyl-functionalized aspartamide, and ethyleneimine.

In certain embodiments, the invention relates to any of the compositions described herein, wherein each third monomer has the structure of Formula III or Formula IV:

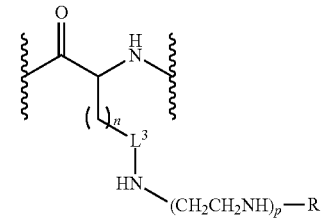

Formula III

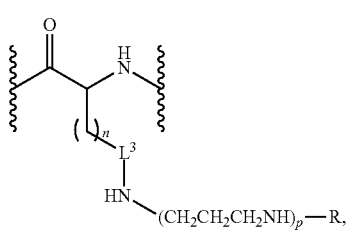

Formula IV wherein
L$^3$ is a bond or —C(=O)—;
p is 1, 2, or 3;
R is H or C$_1$-C$_6$alkyl; and
n is 1, 2, 3, 4, 5, or 6.

In certain embodiments, the invention relates to any of the compositions described herein, wherein n is 1 or 2.

In certain embodiments, the invention relates to any of the compositions described herein, wherein n is 1.

In certain embodiments, the invention relates to any of the compositions described herein, wherein L$^3$ is —C(=O)—.

In certain embodiments, the invention relates to any of the compositions described herein, wherein R is H.

In certain embodiments, the invention relates to any of the compositions described herein, wherein p is 2.

In certain embodiments, the invention relates to any of the compositions described herein, wherein the block copolymer has the following structure:

A$^1$-(first block)-L$^1$-(second block)-L$^2$-(third block)-A$^2$ wherein
A$^1$ is OH or —O—(C$_1$-C$_6$)alkyl;
A$^2$ is H, an amine protecting group, or an amino acid;
L$^1$ is a covalent bond or a first linker; and
L$^2$ is a covalent bond or a second linker.

In certain embodiments, the invention relates to any of the compositions described herein, wherein A$^1$ is —O—(C$_1$-C$_6$)alkyl.

In certain embodiments, the invention relates to any of the compositions described herein, wherein A$^1$ is —OCH$_3$.

In certain embodiments, the invention relates to any of the compositions described herein, wherein A$^2$ is H.

In certain embodiments, the invention relates to any of the compositions described herein, wherein L$^1$ is a first linker.

In certain embodiments, the invention relates to any of the compositions described herein, wherein L$^1$ is —C$_1$-C$_6$alkylene-NR—; and R is H or C$_1$-C$_6$alkyl.

In certain embodiments, the invention relates to any of the compositions described herein, wherein L$^1$ is —CH$_2$CH$_2$—NH—.

In certain embodiments, the invention relates to any of the compositions described herein, wherein L$^2$ is a covalent bond.

In certain embodiments, the invention relates to any of the compositions described herein, wherein the block copolymer comprises from about 3 to about 60 contiguous second monomers.

In certain embodiments, the invention relates to any one of the compositions described herein, wherein the copolymer comprises from about 10 to about 40 contiguous second repeat units. In certain embodiments, the invention relates to any one of the compositions described herein, wherein the copolymer comprises from about 15 to about 35 contiguous second repeat units. In certain embodiments, the invention relates to any one of the compositions described herein, wherein the copolymer comprises about 15, about 16, about 17, about 18, about 19, about 20, about 21, about 22, about 23, about 24, about 25, about 26, about 27, about 28, about 29, about 30, about 31, about 32, about 33, about 34, or about 35 contiguous second repeat units.

In certain embodiments, the invention relates to any of the compositions described herein, wherein the block copolymer comprises from about 10 to about 60 contiguous third monomers.

In certain embodiments, the invention relates to any one of the compositions described herein, wherein the copolymer comprises from about 60 to about 180 contiguous third repeat units. In certain embodiments, the invention relates to any one of the compositions described herein, wherein the copolymer comprises from about 80 to about 160 contiguous third repeat units. In certain embodiments, the invention relates to any one of the compositions described herein, wherein the copolymer comprises about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, or about 140 contiguous third repeat units.

In certain embodiments, the invention relates to any of the compositions described herein, wherein the block copolymer comprises from about 40 to about 300 contiguous first monomers.

In certain embodiments, the invention relates to any one of the compositions described herein, wherein the block copolymer comprises from about 3 to about 40 contiguous first monomers. In certain embodiments, the invention relates to any one of the compositions described herein, wherein the copolymer comprises from about 4 to about 30 contiguous first repeat units. In certain embodiments, the invention relates to any one of the compositions described herein, wherein the copolymer comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 contiguous first repeat units.

In certain embodiments, the invention relates to any of the compositions described herein, wherein the block copolymer is MPEG-b-PCL-b-PLL.

In certain embodiments, the invention relates to any of the compositions described herein, wherein the block copolymer is

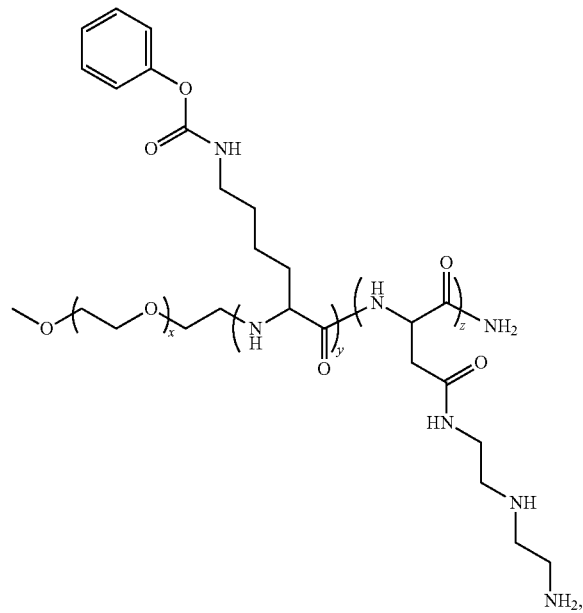

wherein
x is from about 40 to about 300;
y is from about 3 to about 60; and
z is from about 10 to about 60.

In certain embodiments, the invention relates to any of the compositions described herein, wherein the pharmaceutically acceptable carrier is an aqueous liquid.

In certain embodiments, the invention relates to any of the compositions described herein, wherein the aqueous liquid comprises a buffer.

In certain embodiments, the invention relates to any one of the compositions described herein, wherein the buffer is selected from the group consisting of: N-(2-acetamido)-2-aminoethanesulfonic acid (aces), N-(2-acetamido)iminodiacetic acid (ADA), acetate, 2-amino-2-methyl-1,3-propanediol (AMPD), 2-amino-2-methyl-1-propanol (AMP), N,N-bis(2-hydroxyethyl)-2-aminoethanesulfonic acid (BES), 3-(N,N-bis[2-hydroxyethyl]amino)-2-hydroxypropanesulfonic acid (DIPSO), N,N-bis(2-hydroxyethyl)glycine (Bicine), bis(2-hydroxyethyl)iminotris(hydroxymethyl)methane (Bis-Tris), 1,3-bis[tris(hydroxymethyl)methylamino]propane (Bis-Tris propane), borate, citrate, 4-(cyclohexylamino)-1-butanesulfonic acid (CABS), 2-(cyclohexylamino)ethanesulfonic acid (CHES), 3-(cyclohexylamino)-2-hydroxy-1-propanesulfonic acid (CAPSO), 3-(cyclohexylamino)-1-propanesulfonic acid (CAPS), diglycine (Gly-Gly), 3-([1,1-dimethyl-2-hydroxyethyl]amino)-2-hydroxypropanesulfonic acid (AMPSO), glycine, 2-[(2-hydroxy-1,1-bis[hydroxymethyl]ethyl)amino]ethanesulfonic acid (TES), N-(2-hydroxyethyl)piperazine-N'-(4-butanesulfonic acid) (HEPBS), N-(2-hydroxyethyl)piperazine-N'-ethanesulfonic acid (HEPES), 4-(2-hydroxyethyl)-1-piperazinepropanesulfonic acid (EPPS), 4-(N-morpholino)butanesulfonic acid (MOBS), 2-(N-morpholino)ethanesulfonic acid (MES), 3-(N-morpholino)propanesulfonic acid (MOPS), 3-(N-morpholinyl)-2-hydroxypropanesulfonic acid (MOPSO), phosphate, piperazine-N,N'-bis(2-hydroxypropanesulfonic acid) (POPSO), 1,4-piperazinediethanesulfonic acid (PIPES), tris(hydroxymethyl)aminomethane (Tris), 3-(N-tris[hydroxymethyl]methylamino)-2-hydroxypropanesulfonic acid (TAPSO), N-tris(hydroxymethyl)methyl-3-aminopropanesulfonic acid (TAPS), and N-[tris(hydroxymethyl)methyl]glycine (Tricine).

In certain embodiments, the invention relates to any one of the compositions described herein, wherein the concentration of buffer in the aqueous liquid is about 10 mM to about 100 mM.

In certain embodiments, the invention relates to any one of the compositions described herein, wherein the concentration of buffer in the aqueous liquid is about 20 mM, about 30 mM, about 40 mM, about 50 mM, about 60 mM, about 70 mM, about 80 mM, or about 90 mM.

In certain embodiments, the invention relates to any one of the compositions described herein, wherein the concentration of buffer in the aqueous liquid is about 50 mM.

In certain embodiments, the invention relates to any one of the compositions described herein, wherein the pH of the aqueous liquid is about 6.5, about 7.0, about 7.5, about 8.0, about 8.5, about 9.0, or about 9.5.

In certain embodiments, the invention relates to any of the compositions described herein, wherein the pH of the aqueous liquid is about 6.8 to about 7.4.

In certain embodiments, the invention relates to any one of the compositions described herein, wherein the pH of the aqueous liquid is about 7.0.

In certain embodiments, the invention relates to any of the compositions described herein, wherein the block copolymer is in the form of a micelle when in an aqueous liquid.

In certain embodiments, the invention relates to any of the compositions described herein, wherein the average diameter of the micelles, as determined by DLS, is about 20 nm to about 160 nm.

In certain embodiments, the invention relates to any of the compositions described herein, wherein the second block copolymer forms a shell around the micelle.

In certain embodiments, the invention relates to any one of the compositions described herein, wherein the average diameter of the micelles, as determined by DLS, is about 80 nm, about 90 nm, about 100 nm, about 110 nm, or about 120 nm.

In certain embodiments, the invention relates to any one of the compositions described herein, wherein the temperature of the composition is about 18° C. to about 50° C.

In certain embodiments, the invention relates to any one of the compositions described herein, wherein the temperature of the composition is about 20° C., about 22° C., about 24° C., about 26° C., about 28° C., about 30° C., about 32° C., about 34° C., about 36° C., about 38° C., about 40° C., about 42° C., about 44° C., about 46° C., or about 48° C.

In certain embodiments, the invention relates to any one of the compositions described herein, wherein the temperature of the composition is about 23° C.

In certain embodiments, the invention relates to any one of the compositions described herein, wherein the temperature of the composition is about 37° C.

In certain embodiments, the invention relates to any one of the compositions described herein, wherein the first block copolymer does not comprise polyhistidine.

Exemplary siRNA/Anticancer Compositions

In certain embodiments, the invention relates to a composition comprising, consisting essentially of, or consisting of:
- an optional pharmaceutically acceptable carrier;
- an siRNA;
- an anticancer agent; and
- a block copolymer comprising:
  (i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
  (ii) a second block comprising a plurality of second monomers, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate; and
  (iii) a third block comprising a plurality of third monomers, wherein each third monomer is selected from the group consisting of lysine, side-chain aminoalkyl-functionalized lysine, asparagine, side-chain aminoalkyl-functionalized asparagine, arginine, aspartamide, side-chain aminoalkyl-functionalized aspartamide, and ethyleneimine, wherein
the siRNA is non-covalently associated with the block copolymer; and
the anticancer agent is associated with the block copolymer.

In certain embodiments, the invention relates to any of the compositions described herein, wherein the anticancer agent is covalently bound to the block copolymer.

In certain embodiments, the invention relates to any of the compositions described herein, wherein the anticancer agent is an alkylating agent or a nucleic acid cross-linking agent.

In certain embodiments, the invention relates to any of the compositions described herein, wherein the anticancer agent is an alkylating agent.

In certain embodiments, the invention relates to any of the compositions described herein, wherein the anticancer agent is a nucleic acid cross-linking agent.

In certain embodiments, the invention relates to any of the compositions described herein, wherein the anticancer agent comprises Pt(II) or Pt(IV).

In certain embodiments, the invention relates to any of the compositions described herein, wherein the anticancer agent is covalently bound to at least one third monomer.

In certain embodiments, the invention relates to any of the compositions described herein, wherein at least one third monomer has the structure of Formula I:

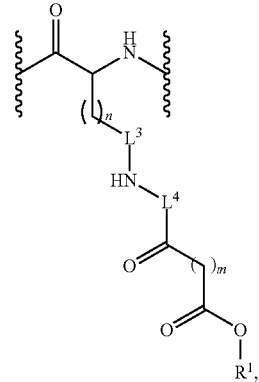

Formula I wherein
$R^1$ comprises the anticancer agent;
$L^3$ is a bond or —C(=O)—;
$L^4$ is a bond or $[-(C_1\text{-}C_6)\text{alkylene-NR}-]_p$;
p is 1, 2, or 3;
R is H or $C_1\text{-}C_6$alkyl;
n is 1, 2, 3, 4, 5, or 6; and
m is 1, 2, 3, 4, 5, or 6.

In certain embodiments, the invention relates to any of the compositions described herein, wherein the anticancer agent is a nucleic acid cross-linking agent.

In certain embodiments, the invention relates to any of the compositions described herein, wherein the anticancer agent comprises Pt(II) or Pt(IV).

In certain embodiments, the invention relates to any of the compositions described herein, wherein the anticancer agent comprises Pt(IV).

In certain embodiments, the invention relates to any of the compositions described herein, wherein $R^1$ is

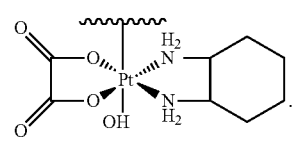

In certain embodiments, the invention relates to any of the compositions described herein, wherein the anticancer agent is a moiety represented by the structural formula:

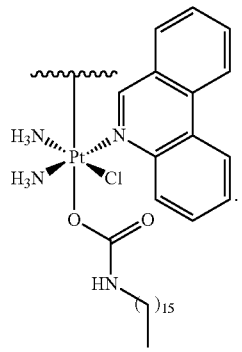

In certain embodiments, the invention relates to any of the compositions described herein, wherein n is 3, 4, or 5.

In certain embodiments, the invention relates to any of the compositions described herein, wherein n is 4.

In certain embodiments, the invention relates to any of the compositions described herein, wherein m is 1, 2, or 3.

In certain embodiments, the invention relates to any of the compositions described herein, wherein m is 2.

In certain embodiments, the invention relates to any of the compositions described herein, wherein $L^3$ is a bond.

In certain embodiments, the invention relates to any of the compositions described herein, wherein $L^3$ is —C(=O)—.

In certain embodiments, the invention relates to any of the compositions described herein, wherein $L^4$ is a bond.

In certain embodiments, the invention relates to any of the compositions described herein, wherein $L^4$ is [—($C_1$-$C_6$)alkylene-NR—]$_p$.

In certain embodiments, the invention relates to any of the compositions described herein, wherein $L^4$ is [—($CH_2CH_2$)—NR—]$_2$.

In certain embodiments, the invention relates to any of the compositions described herein, wherein R is H.

In certain embodiments, the invention relates to any of the compositions described herein, wherein the anticancer agent is non-covalently associated with the block copolymer.

In certain embodiments, the invention relates to any of the compositions described herein, wherein the anticancer agent is an alkylating agent or a nucleic acid cross-linking agent.

In certain embodiments, the invention relates to any of the compositions described herein, wherein the anticancer agent is an alkylating agent.

In certain embodiments, the invention relates to any of the compositions described herein, wherein the anticancer agent is a nucleic acid cross-linking agent.

In certain embodiments, the invention relates to any of the compositions described herein, wherein the anticancer agent comprises Pt(II) or Pt(IV).

In certain embodiments, the invention relates to any of the compositions described herein, wherein the anticancer agent comprises Pt(II).

In certain embodiments, the invention relates to any of the compositions described herein, wherein the block copolymer has the following structure:

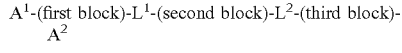

$A^1$ is OH or —O—($C_1$-$C_6$)alkyl;
$A^2$ is H, an amine protecting group, or an amino acid;
$L^1$ is a covalent bond or a first linker; and
$L^2$ is a covalent bond or a second linker.

In certain embodiments, the invention relates to any of the compositions described herein, wherein $L^1$ is a first linker.

In certain embodiments, the invention relates to any of the compositions described herein, wherein $L^1$ is —C(=O)—($C_1$-$C_{10}$-alkylene)-O—.

In certain embodiments, the invention relates to any of the compositions described herein, wherein $L^1$ is a bond.

In certain embodiments, the invention relates to any of the compositions described herein, wherein $L^2$ is a second linker.

In certain embodiments, the invention relates to any of the compositions described herein, wherein $L^2$ is —C(=O)—($C_1$-$C_{10}$-alkylene)-NH—.

In certain embodiments, the invention relates to any of the compositions described herein, wherein $L^2$ is a bond.

In certain embodiments, the invention relates to any of the compositions described herein, wherein the block copolymer comprises from about 3 to about 60 contiguous second monomers.

In certain embodiments, the invention relates to any one of the compositions described herein, wherein the copolymer comprises from about 10 to about 40 contiguous second repeat units. In certain embodiments, the invention relates to any one of the compositions described herein, wherein the copolymer comprises from about 15 to about 35 contiguous second repeat units. In certain embodiments, the invention relates to any one of the compositions described herein, wherein the copolymer comprises about 15, about 16, about 17, about 18, about 19, about 20, about 21, about 22, about 23, about 24, about 25, about 26, about 27, about 28, about 29, about 30, about 31, about 32, about 33, about 34, or about 35 contiguous second repeat units.

In certain embodiments, the invention relates to any of the compositions described herein, wherein the block copolymer comprises from about 10 to about 60 contiguous third monomers.

In certain embodiments, the invention relates to any one of the compositions described herein, wherein the copolymer comprises from about 60 to about 180 contiguous third repeat units. In certain embodiments, the invention relates to any one of the compositions described herein, wherein the copolymer comprises from about 80 to about 160 contiguous third repeat units. In certain embodiments, the invention relates to any one of the compositions described herein, wherein the copolymer comprises about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, or about 140 contiguous third repeat units.

In certain embodiments, the invention relates to any of the compositions described herein, wherein the block copolymer comprises from about 40 to about 300 contiguous first monomers.

In certain embodiments, the invention relates to any one of the compositions described herein, wherein the block copolymer comprises from about 3 to about 40 contiguous first monomers. In certain embodiments, the invention relates to any one of the compositions described herein, wherein the copolymer comprises from about 4 to about 30 contiguous first repeat units. In certain embodiments, the invention relates to any one of the compositions described herein, wherein the copolymer comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 contiguous first repeat units.

In certain embodiments, the invention relates to any of the compositions described herein, wherein the block copolymer is MPEG-b-PCL-b-PLL, wherein at least one PLL monomer has a structure of Formula I:

Formula I

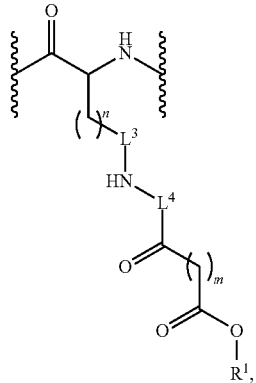

wherein
$R^1$ comprises the anticancer agent;
$L^3$ is a bond or —C(=O)—;
$L^4$ is a bond or [—($C_1$-$C_6$)alkylene-NR—]$_p$;
p is 1, 2, or 3;
R is H or $C_1$-$C_6$alkyl;
n is 4; and
m is 1, 2, 3, 4, 5, or 6.

In certain embodiments, the invention relates to any of the compositions described herein, wherein the block copolymer is MPEG-b-PCL-b-PLL.

In certain embodiments, the invention relates to any of the compositions described herein, wherein the composition further comprises a second block copolymer non-covalently associated with the block copolymer.

In certain embodiments, the invention relates to any of the compositions described herein, wherein the second block copolymer is a diblock copolymer.

In certain embodiments, the invention relates to any of the compositions described herein, wherein the second block copolymer comprises a fourth block comprising a plurality of fourth monomers, and a fifth block comprising a plurality of first monomers.

In certain embodiments, the invention relates to any of the compositions described herein, wherein each fourth monomer has a pKa less than or equal to about 6 in water.

In certain embodiments, the invention relates to any of the compositions described herein, wherein at least one fourth monomer comprises a —$CO_2^-$ functionality at pH about 7.

In certain embodiments, the invention relates to any of the compositions described herein, wherein each fourth monomer is selected from the group consisting of aspartic acid, glutamic acid, glycolic acid, acrylic acid, and methacrylic acid.

In certain embodiments, the invention relates to any of the compositions described herein, wherein the second block copolymer comprises from about 5 to about 240 contiguous fourth monomers.

In certain embodiments, the invention relates to any of the compositions described herein, wherein the mole ratio of fourth monomer to third monomer in the composition is from about 1:1 to about 5:1.

In certain embodiments, the invention relates to any of the compositions described herein, wherein the pharmaceutically acceptable carrier is an aqueous liquid.

In certain embodiments, the invention relates to any of the compositions described herein, wherein the aqueous liquid comprises a buffer.

In certain embodiments, the invention relates to any one of the compositions described herein, wherein the buffer is selected from the group consisting of: N-(2-acetamido)-2-aminoethanesulfonic acid (aces), N-(2-acetamido)iminodiacetic acid (ADA), acetate, 2-amino-2-methyl-1,3-propanediol (AMPD), 2-amino-2-methyl-1-propanol (AMP), N,N-bis(2-hydroxyethyl)-2-aminoethanesulfonic acid (BES), 3-(N,N-bis[2-hydroxyethyl]amino)-2-hydroxypropanesulfonic acid (DIPSO), N,N-bis(2-hydroxyethyl)glycine (Bicine), bis(2-hydroxyethyl)iminotris(hydroxymethyl)methane (Bis-Tris), 1,3-bis[tris(hydroxymethyl)methylamino]propane (Bis-Tris propane), borate, citrate, 4-(cyclohexylamino)-1-butanesulfonic acid (CABS), 2-(cyclohexylamino)ethanesulfonic acid (CHES), 3-(cyclohexylamino)-2-hydroxy-1-propanesulfonic acid (CAPSO), 3-(cyclohexylamino)-1-propanesulfonic acid (CAPS), diglycine (Gly-Gly), 3-([1,1-dimethyl-2-hydroxyethyl]amino)-2-hydroxypropanesulfonic acid (AMPSO), glycine, 2-[(2-hydroxy-1,1-bis[hydroxymethyl]ethyl)amino]ethanesulfonic acid (TES), N-(2-hydroxyethyl)piperazine-N'-(4-butanesulfonic acid) (HEPBS), N-(2-hydroxyethyl)-piperazine-N'-ethanesulfonic acid (HEPES), 4-(2-hydroxyethyl)-1-piperazinepropanesulfonic acid (EPPS), 4-(N-morpholino)butanesulfonic acid (MOBS), 2-(N-morpholino)ethanesulfonic acid (MES), 3-(N-morpholino)propanesulfonic acid (MOPS), 3-(N-morpholinyl)-2-hydroxypropanesulfonic acid (MOPSO), phosphate, piperazine-N,N'-bis(2-hydroxypropanesulfonic acid) (POPSO), 1,4-piperazinediethanesulfonic acid (PIPES), tris (hydroxymethyl)aminomethane (Tris), 3-(N-tris[hydroxymethyl]methylamino)-2-hydroxypropanesulfonic acid (TAPSO), N-tris(hydroxymethyl)methyl-3-aminopropanesulfonic acid (TAPS), and N-[tris(hydroxymethyl)methyl]glycine (Tricine).

In certain embodiments, the invention relates to any one of the compositions described herein, wherein the concentration of buffer in the aqueous liquid is about 10 mM to about 100 mM.

In certain embodiments, the invention relates to any one of the compositions described herein, wherein the concentration of buffer in the aqueous liquid is about 20 mM, about 30 mM, about 40 mM, about 50 mM, about 60 mM, about 70 mM, about 80 mM, or about 90 mM.

In certain embodiments, the invention relates to any one of the compositions described herein, wherein the concentration of buffer in the aqueous liquid is about 50 mM.

In certain embodiments, the invention relates to any one of the compositions described herein, wherein the pH of the aqueous liquid is about 6.5, about 7.0, about 7.5, about 8.0, about 8.5, about 9.0, or about 9.5.

In certain embodiments, the invention relates to any one of the compositions described herein, wherein the pH of the aqueous liquid is about 6.8 to about 7.4.

In certain embodiments, the invention relates to any one of the compositions described herein, wherein the pH of the aqueous liquid is about 7.0.

In certain embodiments, the invention relates to any of the compositions described herein, wherein the block copolymer is in the form of a micelle when in aqueous liquid.

In certain embodiments, the invention relates to any of the compositions described herein, wherein the block copolymer is in the form of a micelle; the composition further comprises a second block copolymer non-covalently associated with the block copolymer; and the second block copolymer forms a shell around the micelle.

In certain embodiments, the invention relates to any of the compositions described herein, wherein the average diameter of the micelles, as determined by DLS, is about 20 nm to about 160 nm.

In certain embodiments, the invention relates to any one of the compositions described herein, wherein the average diameter of the micelles, as determined by DLS, is about 80 nm, about 90 nm, about 100 nm, about 110 nm, or about 120 nm.

In certain embodiments, the invention relates to any one of the compositions described herein, wherein the temperature of the composition is about 18° C. to about 50° C.

In certain embodiments, the invention relates to any one of the compositions described herein, wherein the temperature of the composition is about 20° C., about 22° C., about 24° C., about 26° C., about 28° C., about 30° C., about 32° C., about 34° C., about 36° C., about 38° C., about 40° C., about 42° C., about 44° C., about 46° C., or about 48° C.

In certain embodiments, the invention relates to any one of the compositions described herein, wherein the temperature of the composition is about 23° C.

In certain embodiments, the invention relates to any one of the compositions described herein, wherein the temperature of the composition is about 37° C.

Exemplary Methods

In certain embodiments, the invention relates to a method of treating cancer comprising administering to a subject in need thereof a therapeutically effective amount of any one of the compositions described herein.

In certain embodiments, the invention relates to any one of the methods described herein, wherein the subject is human.

In certain embodiments, the invention relates to any one of the methods described herein, wherein the composition is administered intravenously.

EXEMPLIFICATION

The invention now being generally described, it will be more readily understood by reference to the following, which is included merely for purposes of illustration of certain aspects and embodiments of the present invention, and is not intended to limit the invention.

Example 1—General Materials and Methods

Materials.

Methoxyl-poly(ethylene glycol)-block-poly-(ε-caprolactone)-block-poly(L-lysine) (MPEG-b-PCL-b-PLL) was synthesized as described in Qi, R. et al. *J Control Release* 152 Suppl 1, e167-168 (2011). Its structure was verified by $^1$HNMR and found to be comprised of $MPEG_{114}$-b-$PCL_{20}$-b-$PLL_{25}$, where the subscript numbers denote the degrees of polymerization of each individual monomer in a given block. This polymer is abbreviated "P", hereafter. N-hydroxysuccinimide (NHS), 1-(3-dimethylaminopropyl)-3-ethylcarbodiimide hydrochloride (EDC.HCl), guanosine 5'-monophosphate disodium salt (5'-GMP) and sodium ascorbate were purchased from Sigma-Aldrich. Oxaliplatin and cisplatin were purchased from ChemiChem International Development Co., Ltd. They are abbreviated as Oxa (II) and Cis(II), respectively, to distinguish them from their platinum(IV) prodrugs in which the Pt atoms are in +4 valence. OxaPt(IV) prodrugs were synthesized and systematically characterized by NMR and MS following procedures described in Xiao, H. et al. *J Control Release* 163, 304-314 (2012). The CisPt(IV) derivatives were similarly synthesized. All other chemicals and solvents were used without further purification. Control (c-)siRNA that targets the sequence 5'-GGGUAAGUGUCCUACUGAAGU-3', and BCL-2 siRNA that targets the sequence 5'-UGUG-GAUGACUGA-GUACCUGA-3' were purchased from Integrated DNA Technology. (IW, USA). The c-siRNA sequence did not match any known sequence in the human genome. Luciferase GL3 siRNA was purchased for GenePharma Co. Ltd. (Shanghai, China).

General Measurements.

$^1$HNMR spectra were measured using a Unity-300 MHz NMR spectrometer (Bruker) at room temperature. Fourier Transform Infrared (FT-IR) spectra were recorded on a Bruker Vertex 70 spectrometer. Mass Spectroscopy measurements were performed on a Quattro Premier XE system (Waters) equipped with an electrospray interface (ESI-MS). These methods along with matrix-assisted laser-desorption ionization and time-of-flight mass spectroscopy (MALDI-TOF-MS, Waters, USA) were used to study the reaction 5'-GMP and siRNA with various platinum species.

Atomic absorption spectroscopy (generation 8.0, Perkin Elmer) was used to study the kinetics of siRNA platination and to determine the platinum content in all micellar formulations. Inductively coupled plasma mass spectrometry (ICP-MS, Xseries II, Thermo scientific, USA) was used for quantitative determination of trace levels of platinum in cancer cells and to quantify Pt-DNA adduct formation. Sizes and distributions of micelles were determined by dynamic light scattering (DLS) with a vertically polarized He—Ne laser (DAWN EOS, Wyatt Technology, USA). The size and morphologies of the micelles very visualized using a JEOL JEM-1011 electron microscope. Particle size and zeta potential measurements were conducted on a Malvern Zetasizer Nano ZS90. Micelles were prepared by directly dissolving various modified triblock copolymers in water at 0.5 mg/mL. The critical micelle concentration (CMC) values of M(P) and M(OxaPt(IV)) were measured using pyrene as a fluorescence probe.

Monitoring of 5'-GMP Binding with Various Platinum Species by $^1$HNMR.

(10 mM) 5'-GMP and (5 mM) OxaPt(II) were mixed in 700 μL of $D_2O/H_2O$ (v/v=1:9), transferred to an NMR tube and placed in a 37° C. water bath for various time periods prior to $^1$HNMR measurement. Analogous methods were employed to obtain spectra for the reaction of 5'-GMP with OxaPt(IV), CisPt(II) and CisPt(IV). The binding kinetics of 5'-GMP to each platinum species were determined by measuring the relative amounts of free and Pt-bound 5'-GMP at each time point, integrating the ratio of the $^1$HNMR peaks at 8.5 ppm to 8.09 ppm.

Monitoring of Single-Stranded siRNA Binding with Various Platinum Species by MALDI-TOF-MS.

A single-stranded siRNA (UCA GGU ACU CAG UCA UCC ACA TT) was mixed with OxaPt(II) at a molar ratio of 1:10 in RNAase free water (RNA final concentration: 50

μM; Pt final concentration: 500 μM; total volume: 100 μL). The reaction mixture was placed in a 37° C. incubator and 10 μL of sample were removed at various time points to obtain MALDI-TOF-MS spectra (positive model). Analogous methods were employed to obtain spectra of the reaction products of siRNA with OxaPt(IV), CisPt(II) and CisPt(IV).

Monitoring of double-stranded siRNA binding with various platinum species by AAS. A double-stranded RNA (sense: UGUGGAUGACUGAGUACCUG-ATT; antisense: UCAGGUACUCA-GUCAUCCACATT) was mixed with OxaPt(II) at a molar ratio of 1:10 in RNAase free water (RNA final concentration: 5 μM; Pt final concentration at 50 μM; total volume of 100 μL). The reaction mixture was placed in a 37° C. incubator and samples were isolated after 30 m, 1 h, 6 h, and 12 h of incubation. The RNA was then isolated using a centrifugation separation device (molecular cut-off 3000 Da, spun at 10,000 rpm; Nanosep®3k, Pall Corporation, USA). Five wash cycles with RNAase free water (5×100 μL) then ensued. An aliquot of 2 μL from each sample was obtained for optical density (OD) measurements in order to quantify the concentration of RNA in the original sample, using a NanoDrop reader. The remainder of each sample was diluted in 3% $HNO_3$ for Pt content measurement via AAS. The experiments were performed in triplicate and data are presented such that the concentration of Pt-RNA adducts at each time point are expressed as "μmol Pt/μmol RNA". Analogous methods were employed to obtain similar values for the numbers of Pt-RNA adducts formed by the reaction of siRNA with OxaPt(IV), CisPt(II) or CisPt(IV) at similar time points.

Cell Culture.

MCF-7 and OVCAR4 cell lines were obtained from ATCC and cultured in Dulbecco's Modified Eagle Medium (DMEM, Gibco, Carlsbad, Calif.)), containing RPMI 1640 supplemented with 10% fetal bovine serum (FBS, Gibco at 37° C. with 5% $CO_2$).

Real Time PCR.

BCL-2 siRNA was first pre-incubated with different platinum(II) (i.e. OxaPt(II) or CisPt(II)) or platinum(IV) containing species (i.e. OxaPt(IV) or CisPt(IV)) for various time periods and subsequently transfected into MCF-7 and OVCAR-4 cells in a 6-well plate format, using an RNAi-MAX Kit and by following the manufacturers instructions (Invitrogen, Thermo-Fisher, USA). 48 hours after transfection, total RNA was isolated using an RNeasy mini-kit (Qiagen, Germantown, Md.) and quantified by NanoDrop. 300 ng of mRNA were subsequently subjected to qRT-PCR analysis, targeting BCL-2 and glyceraldehyde 3-phosphate dehydrogenase (GAPDH) by using the SYBR Premix Ex (Takara, USA) and by using an Applied Biosystems StepOne Real-Time PCR System. Relative gene expression values were determined by the ΔΔCT method using StepOne Software v2.1 (Applied Biosystems). Data are presented as fold differences in siRNA expression normalized to GAPDH (house-keeping gene used as endogenous reference), employing a standard curve, and are reported relative to untreated (control) cells. The sequence of the primers used for BCL-2 and GAPDH are as follows: BCL-2 forward—5-CTGCACCTGACGCCCTTCACC-3; Bcl-2 reverse—5-CACATGACCCCACCGAACTCAAAGA-3; GAPDH forward—5-TTCACCACCATGGAGAAGGC-3; and GAPDH reverse primer—5-GGCATGGACTGTGGTCATGA-3 (Integrated DNA Technology. IW, USA). The specificity of each set of primers was verified by melting curve analysis.

Formation of Polymeric Micelles.

PEO-b-PCL-b-PLL-based micelles (i.e. M(P)) were prepared as follows: 50 mg of P were dissolved in 10 mL DMF; 50 mL of water were then added drop-wise into the flask under continuous agitation, forming M(P) in suspension. The solution was then dialyzed against water to remove the organic solvent and freeze-dried for storage.

Conjugation of OxaPt(IV) to Polymeric Micelles.

OxaPt(IV) was conjugated to M(P) in aqueous solution, using EDC/NHS chemistry to prepare micellar constructs that were bound to the platinum(IV) species via amide bonds (i.e. M(OxaPt(IV))). Briefly, (0.191 g, 1 mmol) EDC-HCl and (0.115 g, 1 mmol) NHS were dissolved in deionized water under stirring. (0.42 g, 0.8 mmol) OxaPt(IV) was then added to the aqueous solution. After the suspension mixture became clear, (0.5 g) P (containing 1.25 mmol $NH_2$ groups) was added to the (100 mL) reaction mixture and stirred at RT for 24 h; the suspension was then dialyzed against water for an additional 12 h and lyophilized to obtain M(OxaPt(IV)). The Pt content in M(OxaPt(IV)) was measured by ICP-OES and found to ~10 wt %.

Complexation of siRNA with Polymeric Micelles.

Suspensions of M(P) or M(OxaPt(IV)) were diluted with Opti-MEM medium (Invitrogen) to different final concentrations, varying the numbers of amine groups in solution. Equal volume solutions containing different Bcl-2 or control (c-)siRNA where then added to the micelles, varying the ratios of free amines to phosphates (N/P) in suspension. The suspensions were then mixed by gentle pipetting and the siRNA-complexed micelles were allowed to equilibrate at RT for 30 m. For electrophoresis-retardation analyses, complexes formed from either M(P) or M(OxaPt(IV)) and siRNA at different N/P ratios, ranging from 0.5 to 16, were prepared for a fixed (1 mM) concentration of siRNA; they were then ran on a 1% agarose gel in 0.5 mM tris-borate-EDTA buffer (TBE buffer; 89 mM Tris, 90 mM boric acid, 2 mM EDTA, pH 8.3) at 80 V for 30 m. Bands containing free and micellar bound siRNA were visualized using a UV illuminator (Tanon GIS System) after ethidium bromide staining.

In Vitro Cytotoxicity Measurements.

MCF-7 cells were seeded in 96-well plates at a density of $1 \times 10^4$ cells/well. 100 μL of DMEM supplemented with 10% FBS were added to each well and the cells were incubated at 37° C. for 24 h. The cells were then treated with OxaPt(II), OxaPt(IV), or M(OxaPt(IV)) with and without micellar-complexed BCL-2 or c-siRNA. An equivalent (100 nM) concentration of siRNA was added to each well and media was replaced by fresh DMEM after 4 h; the cells were subsequently allowed to incubate at 37° C. for an additional 48 h prior to evaluation of any treatment cytotoxicity, using the MTT assay. In brief, (20 μL) MTT solution (5 mg/mL) in PBS buffer was added to each well and allowed to incubate for 4 h. (150 μL) DMSO was then added to the cells to replace the MTT-containing media. After gentle agitation for 5 min, the absorbance of each well at 570 nm was recorded on a Bio-Rad Plate Reader. All experiments were conducted in triplicate.

Intracellular Uptake of Fluorescently-Labeled Micelles.

For confocal microscopy experiments, MCF-7 cells were plated on coverslips in 6-well plates ($1 \times 10^5$ cells/well) and cultured with RPMI 1640 supplemented with 10% FBS for 24 h. The cells were then incubated with 50 nM Alexa488-labeled siRNA that was electrostatically complexed to micelles, which were also covalently conjugated to Cy5.5 (i.e. M(Cy5.5/Alexa488 siRNA)) or to Cy5.5 and OxaPt(IV) (i.e. M(Cy5.5/OxaPt(IV)/Alexa488 siRNA), for 1 or 4 h. After removal of media, the cells were then washed twice with cold phosphate buffered saline (PBS, pH 7.4, 0.01 M) and fixed with 4% formaldehyde (Sigma-Aldrich, St. Louis, USA). To label the cell nucleus, samples were incubated with 1 mg/mL DAPI (Sigma-Aldrich, St. Louis, USA) for 15 min in PBS, followed by extensive rinsing with PBS. Slides were mounted on a coverslip and observed by using an Olympus FV1000 laser confocal scanning microscope imaging system (Japan).

For flow cytometry measurements, LUC+MCF-7 were similarly cultured in 12-well plates ($3 \times 10^4$ cells/well) prior to incubation with M(Cy5.5/Alexa488 siRNA) or M(Cy5.5/OxaPt(IV)/Alexa488 siRNA) for 1 or 4 h The cells were washed twice with cold PBS, lysed with trypsin-EDTA solution, collected by centrifugation (1500 rpm, 5 min), and finally analyzed for fluorescence content using a FACSCalibur flow cytometer (BD Biosciences, USA). Cells with fluorescence above the threshold intensity for untreated cells (i.e. blank) were quantified and compared. The percentage of such cells in the total population was considered as a measure of uptake efficiency. Data were analyzed using FlowJo software (Version 7.6.2)

Quantification of the Intracellular Uptake of Various Platinum Species.

MCF-7 cells were seeded in 12-well plates at a density of $10^5$ cells per well and incubated overnight in 1 mL of DMEM containing 10% FBS. 100 LL of each oxaliplatin containing treatment (e.g OxaPt(II), OxaPt(II)+M(c-siRNA), OxaPt(II)+M(Bcl-2), M(OxaPt(IV)/c-siRNA) or M(OxaPt(IV)/Bcl-2)) were then added to each well to a final Pt concentration of 2 µg/mL; note, for siRNA containing treatments, the final siRNA concentration in each well was 100 nM. After 4 h of treatment incubation, media was exchanged with an equal volume of DMEM, containing 10% FBS; and, cells were incubated for an additional 24 h followed by lysis and quantification of Pt content by ICP-MS.

Cellular Apoptosis Assays.

MCF-7 cells were cultured in 12-well plates and treated with various oxaliplatin formulations at a fixed platinum dose of 2 µg/mL. After 48 h, apoptotic cells were detected on flow cytometry using the Annexin V-FITC Apoptosis Detection Kit I (BD Biosciences, San Jose, Calif.); and, the results were analyzed using WinMDI 2.9 software.

Example 2—Monitoring the Reaction of siRNA with Various Platinum Species

OxaPt(II) and CisPt(II) are known to bind to guanine (G) and adenine (A) bases in both DNA and RNA. To compare the relative reactivity of these platinum(II) species as compared to their platinum(IV) counterparts (namely OxaPt(IV) and CisPt(IV)), we first incubated each of these four compounds with guanosine monophosphate (5'-GMP) for different time intervals and in conditions that would mimic a typical in vitro RNAi experiment (i.e. 30 min, 1 h, 3 h, 6 h and 12 h at 37° C.). Formation of Pt-(5'-GMP)$_2$ adducts were subsequently monitored by ESI-MS (FIG. 4A and FIG. 4B) and by MALDI/TOF MS (data not shown). Differences in the kinetics of adduct formation by various platinum(II) and platinum(IV) species were subsequently studied by $^1$HNMR spectroscopy under similar conditions. The chemical shifts of the H8 proton on the guanosine base (e.g. 8.5 ppm in the DACHPt(5'-GMP)$_2$ adduct vs. 8.09 ppm in unreacted 5'-GMP) were monitored at various time points after co-incubation of (10 mM) 5'-GMP with either (5 mM) OxaPt (II) or OxaPt(IV) species (data not shown). By integrating the ratio of the two peaks at each time point, the relative amount of DACHPt(5'-GMP)$_2$ adduct to total 5'-GMP could be calculated in solutions containing either OxaPt(II) (green) or OxaPt(IV) (red) and plotted as a function of time (FIG. 4C). The results showed that approximately 10% of the 5'-GMP pool already consisted of DACHPt(5'-GMP)$_2$ adducts by 30 m after incubation with OxaPt(II); the number of adducts that were formed increased exponential over the first 6 h, reaching >40% of the total pool, and thereby, continued to increase linearly over time. Similarly rapid formation and time dependent increases in the amounts of Pt(NH$_3$)$_2$(5'-GMP)$_2$ adducts were seen when 5'-GMP was reacted with CisPt(II) but not when it was incubated in solutions that contained CisPt(IV) (data not shown).

Figure 4H:
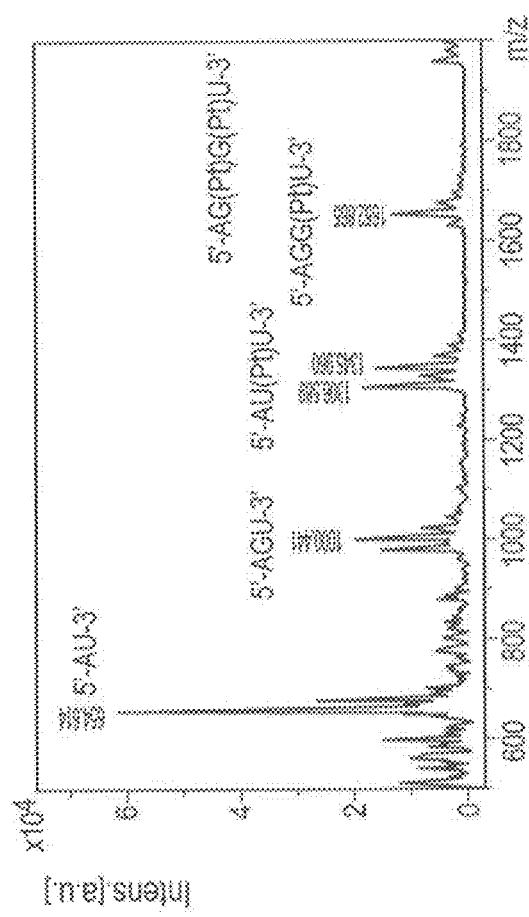
FIG. 4H is a MALDI-TOF-MS spectrum (intensity (a.u.) vs. m/z) of the species produced by enzymatic cleavage of the antisense chain of BCL-2 siRNA by RNase A after incubation with OxaPt(II) to demonstrate sites of platination.
Figure 4G:
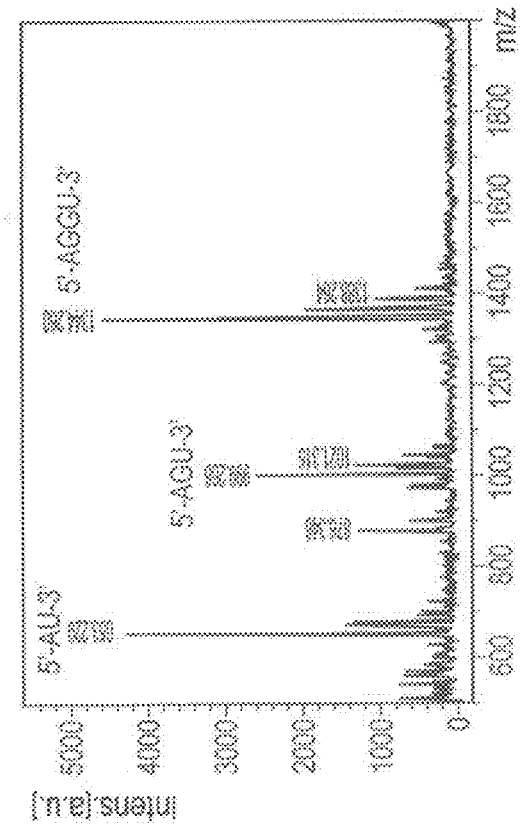
FIG. 4G is a MALDI-TOF-MS spectrum (intensity (a.u.) vs. m/z) of the species produced by enzymatic cleavage of the antisense chain of BCL-2 siRNA by RNase A before incubation with OxaPt(II) to demonstrate sites of platination.
Figure 5A:
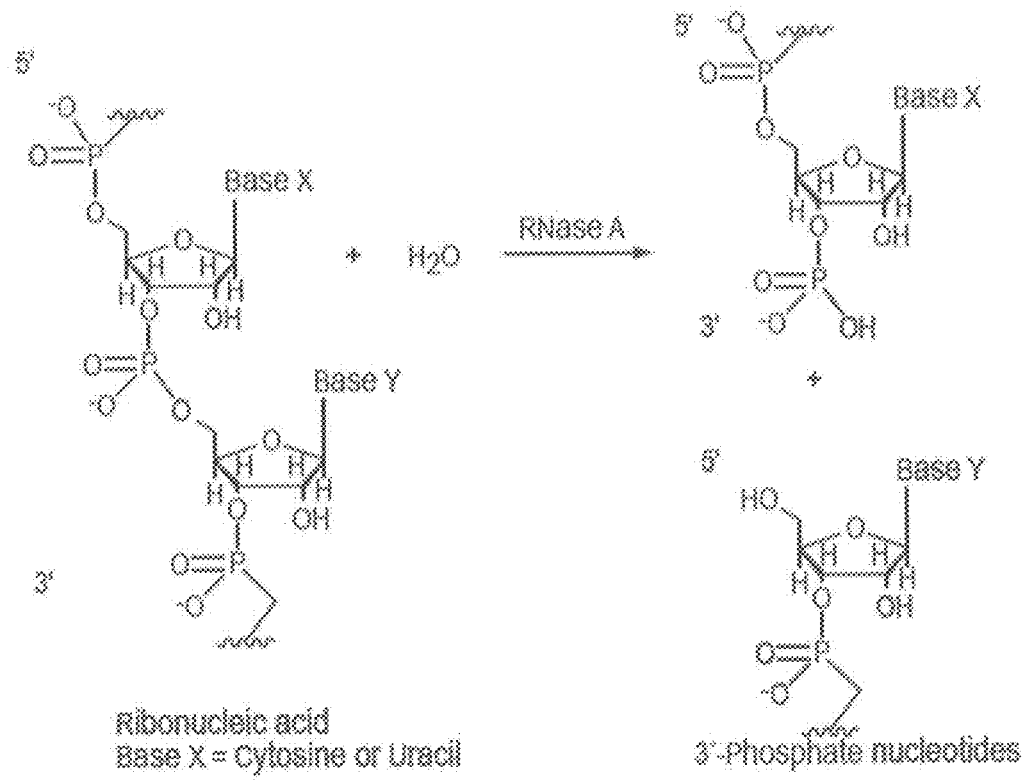
FIG. 5A is a schematic illustration of the reaction of RNase A with RNA.
Figure 5B:
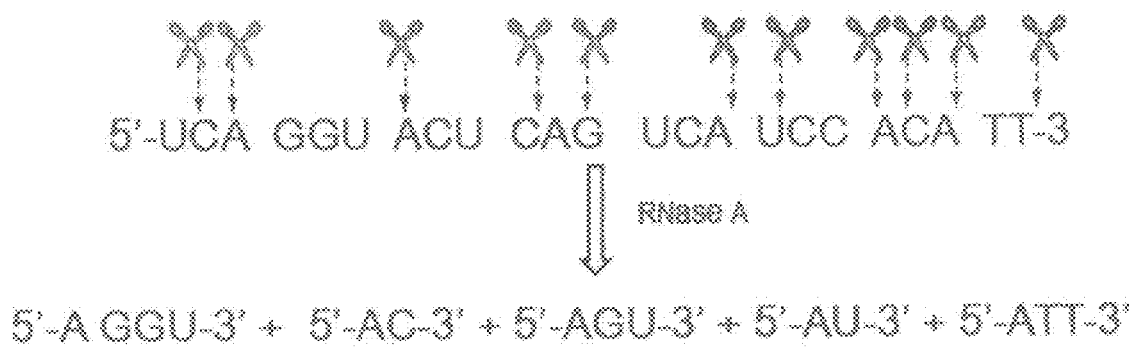
FIG. 5B is a schematic illustration of possible reaction products obtained after site specific cleavage of ss-BCL-2 siRNA (anti-sense) by RNase A. Mass peaks of 5'-AU-3', 5'-AGU-3' and 5'-AGGU-3' can be found in the MALDI/TOF-MS spectra in FIG. 4E.
Figure 5C:
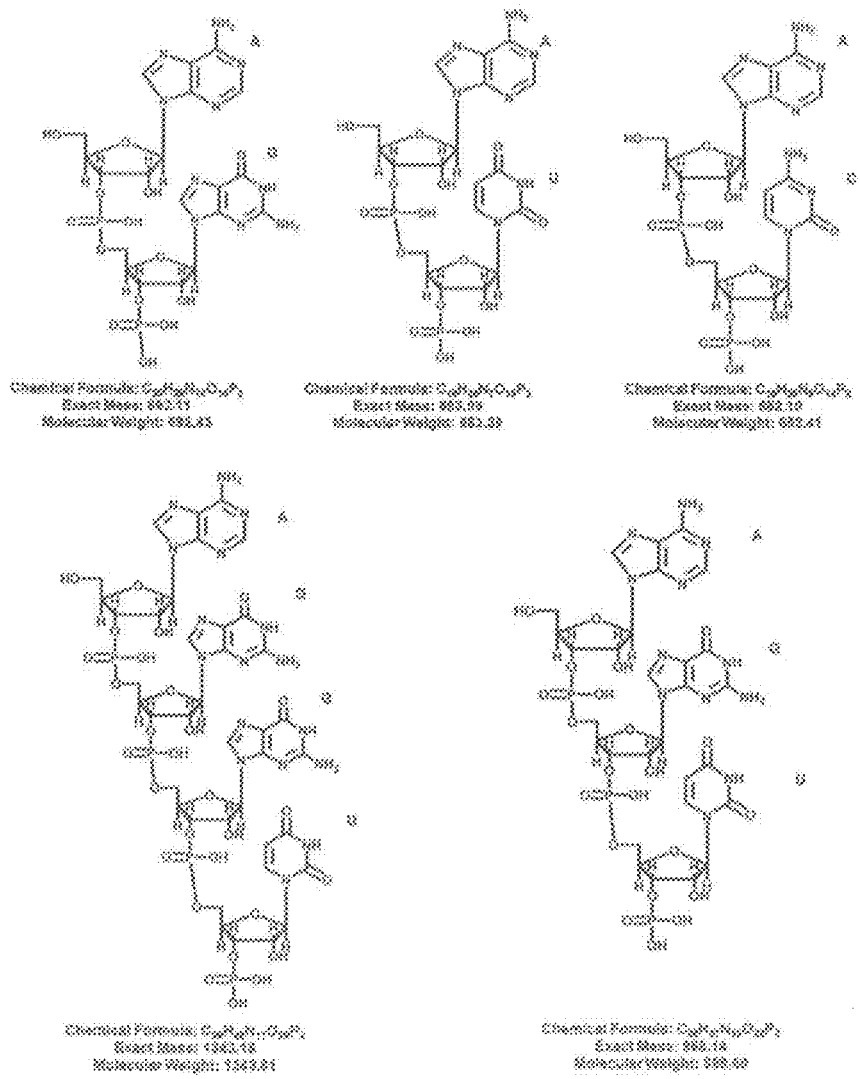
FIG. 5C is the structure, chemical formula, exact mass, and molecular weight of possible reaction products obtained after site specific cleavage of ss-BCL-2 siRNA (anti-sense) by RNase A. Mass peaks of 5'-AU-3', 5'-AGU-3' and 5'-AGGU-3' can be found in the MALDI/TOF-MS spectra in FIG. 4E.
Figure 5D:
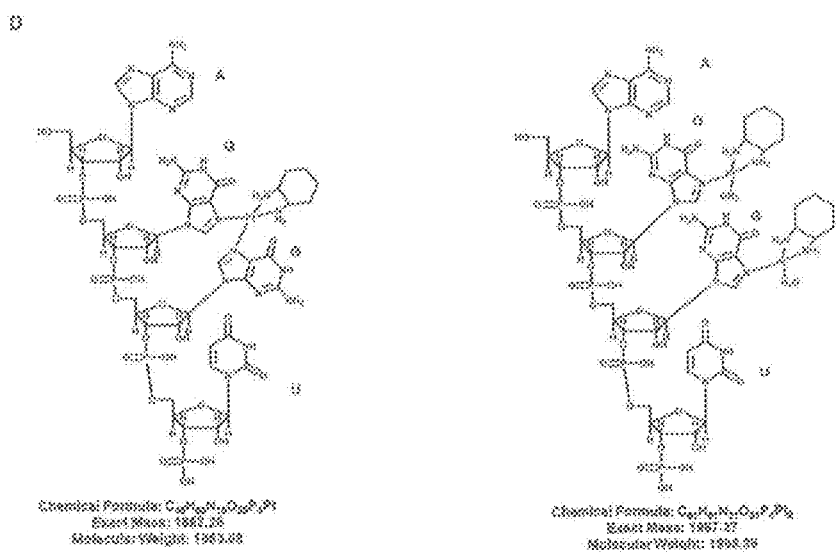
FIG. 5D is the structure, chemical formula, exact mass, and molecular weight of the possible oligo-nucleotide reaction products of platinated ss-BCL-2 siRNA after cleavage by RNase A; note, 5'-AG(Pt)GU-3' and 5'-AG(Pt)G(Pt)U-3' are the potential cleavage products. Note, "Pt" here denotes "DACHPt".

MALDI/TOF MS was used to ascertain the kinetics of platinum-RNA adduct formation using BCL-2 siRNA that was incubated with a 10-fold excess of various platinum(II) or platinum(IV) species. These experiments demonstrated that Pt-siRNA adducts could be detected as early as 1 h in the presence of oxaPt(II) and by 30 m when incubated with CisPt(II) (FIG. 4D). Notably, no Pt-siRNA adducts were detected in solutions of BCL-2 siRNA containing OxaPt(IV) or CisPt(IV) even after 24 h of co-incubation under physiological conditions (pH 7.4; FIG. 4E). AAS measurements of siRNA that had been isolated after co-incubation with various platinum species was conducted to determine the concentration of Pt-siRNA adducts formed over time. These results indicate that >50% of the siRNA transcripts were platinated by 3 h of incubation with OxaPt(II) (FIG. 4F). To determine the platination sites on the transcripts, MALDI/TOF MS experiments using a model SS oligonucleotide of DNA that contained a single GG site were used to verify the formation of mono- and bis-Pt-DNA adducts in the presence of OxaPt(II) but not OxaPt(IV) (data not shown). MALDI/TOF MS was then conducted after enzymatic cleavage of the antisense chain of BCL-2 siRNA by RNase A before (FIG. 4G) and after incubation (FIG. 4H) incubation with OxaPt (II), demonstrating two distinct reaction sites (FIG. 5).

Figure 6:
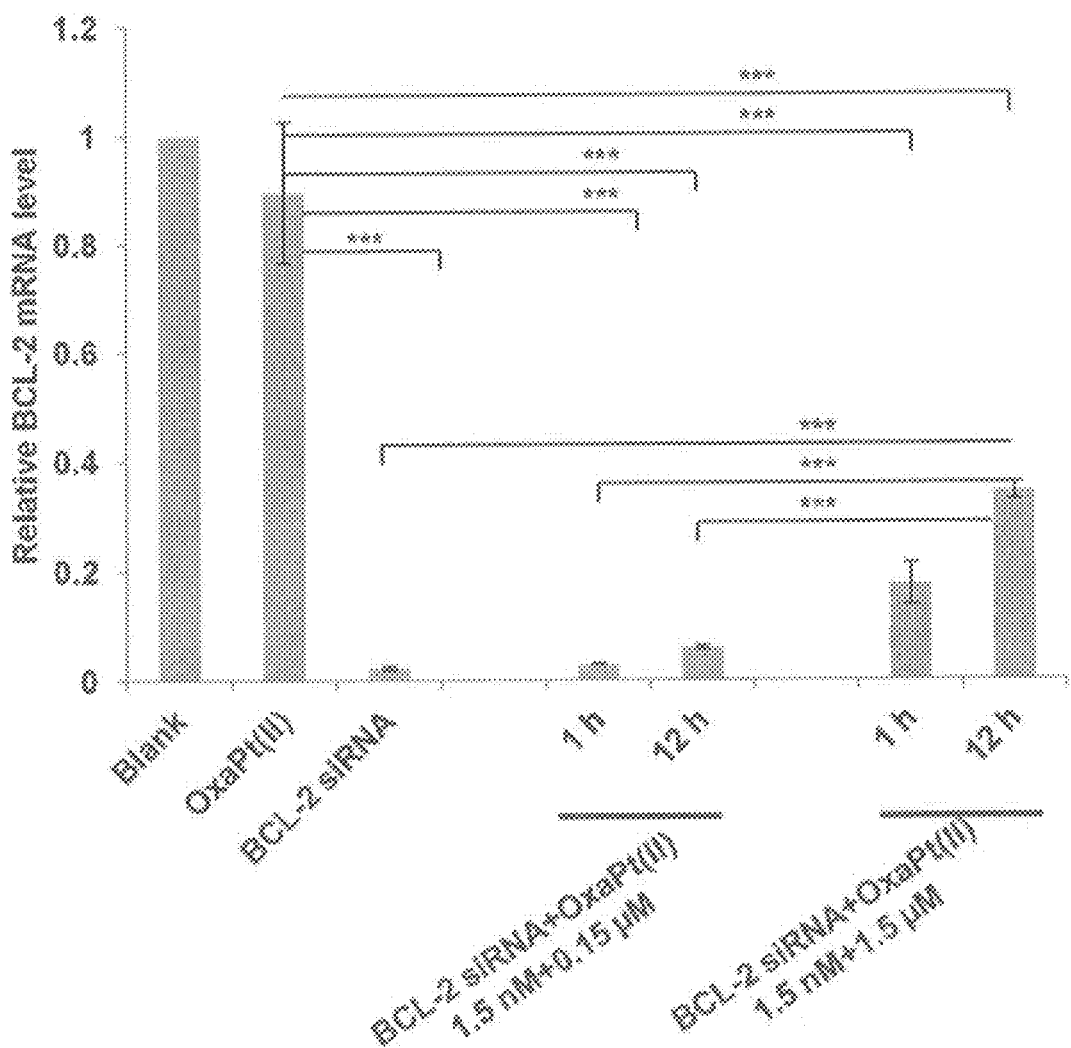
FIG. 6 is a bar graph of relative BCL-2 mRNA levels. These data show that incubation of OxaPt(II) with siRNA results in a concentration and time-dependent decrease in silencing efficiency. Relative BCL-2 mRNA levels in MCF-7 breast cancer cells were determined by RT-qPCR at 48 h after lipofectamine-based transfection with BCL-2 siRNA. The siRNA was either used directly or after pre-incubation with different concentrations of OxaPt(II) for various durations of time (1 vs. 12 h). Significance is denoted by ***p<0.001.
Figure 7A:
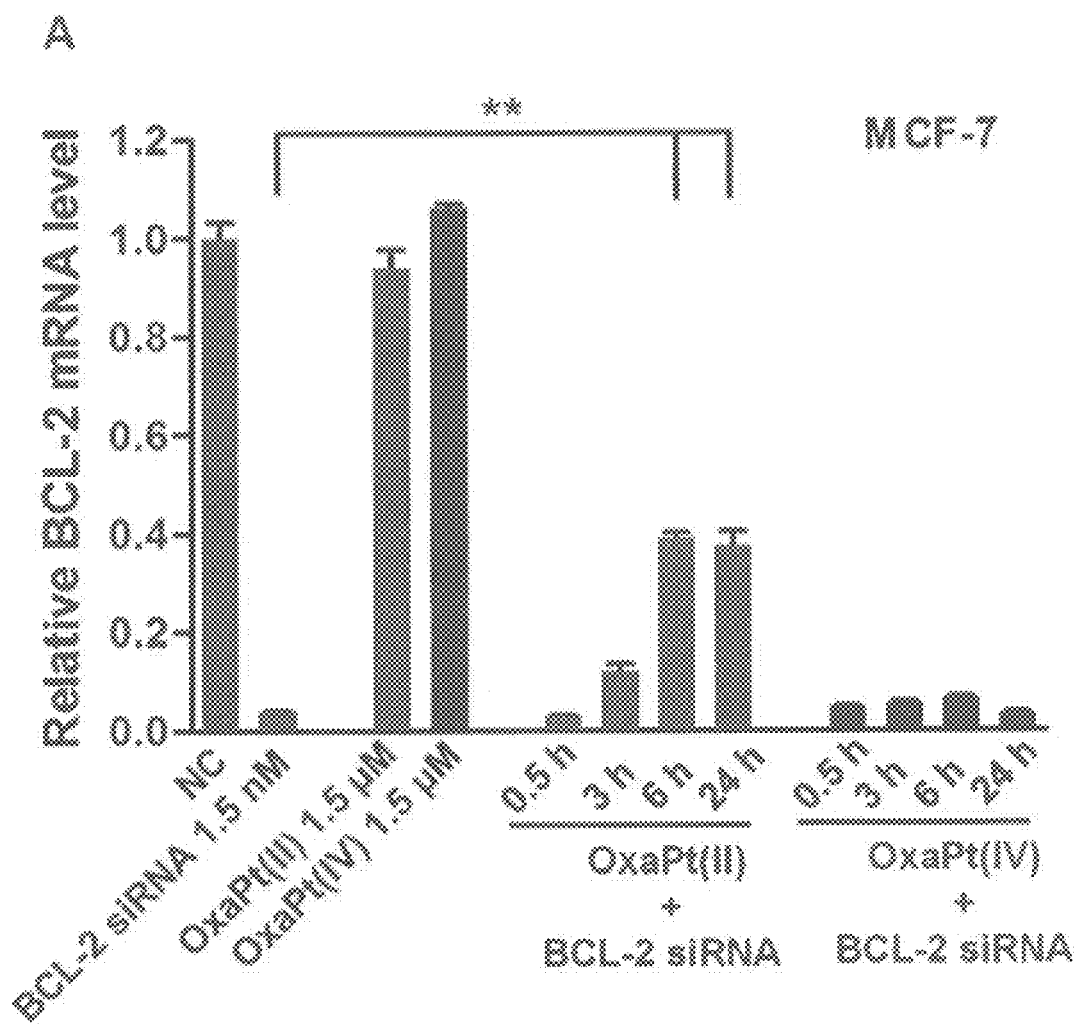
FIG. 7A is a bar graph of relative BCL-2 mRNA levels in MCF-7 breast cancer cells at 37° C. and at 24 h after lipofectamine-based transfection of BCL-2 siRNA. (1.5 nM) siRNA was utilized as is or similarly preincubated with either (1.5 uM) platinum(II) or platinum(IV) species for various time periods (as indicated) prior to transfection. Data are depicted as mean values±standard deviations of the mean (n=3 technical replicates per condition; note, 3 experimental replicates were similar conducted for each cell line and treatment, yielding analogous results. Significance is defined as p<0.01; *p<0.001.
Figure 7B:
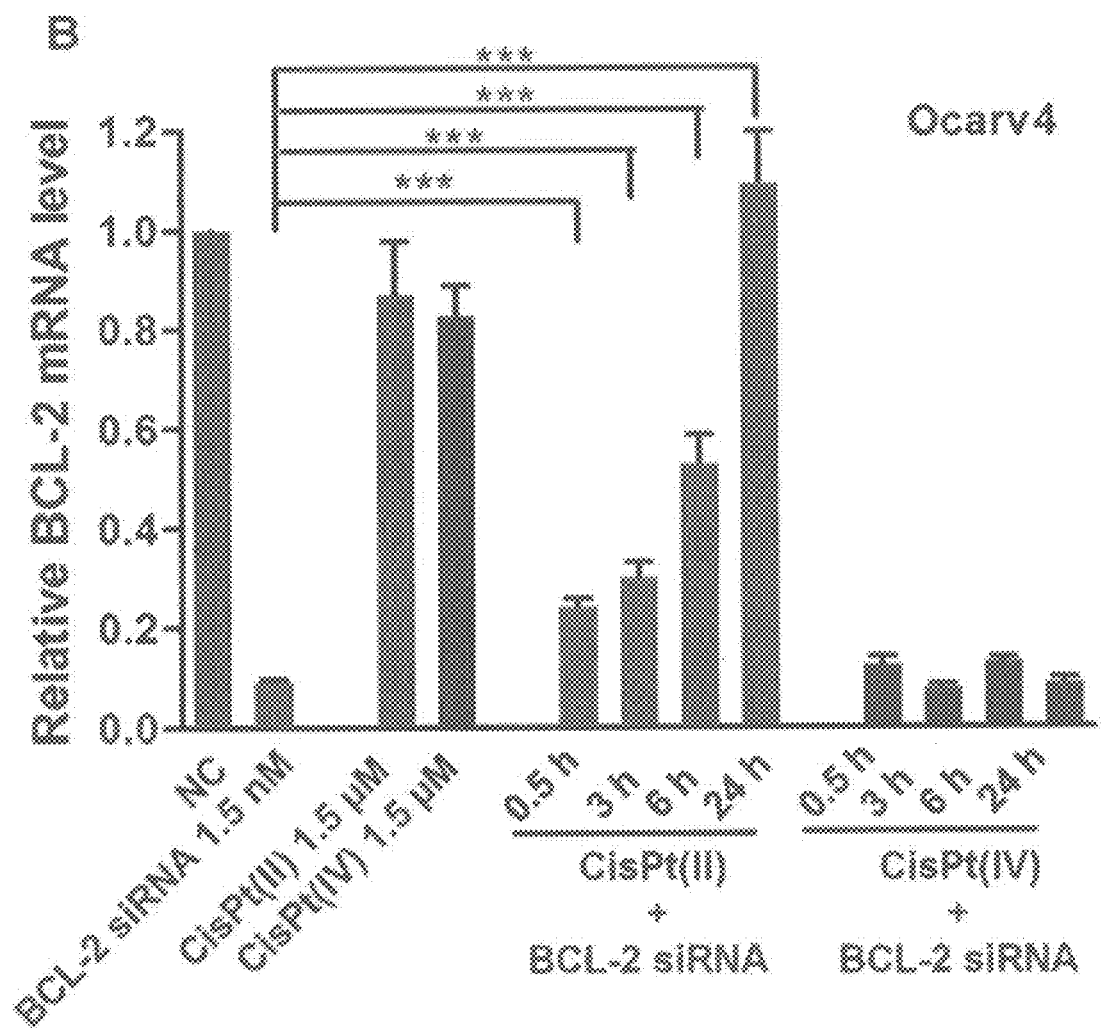
FIG. 7B is a bar graph of relative BCL-2 mRNA levels in OVCAR-4 ovarian cancer cells at 37° C. and at 24 h after lipofectamine-based transfection of BCL-2 siRNA. (1.5 nM) siRNA was utilized as is or similarly preincubated with either (1.5 uM) platinum(II) or platinum(IV) species for various time periods (as indicated) prior to transfection. Data are depicted as mean values±standard deviations of the mean (n=3 technical replicates per condition; note, 3 experimental replicates were similar conducted for each cell line and treatment, yielding analogous results. Significance is defined as p<0.01; *p<0.001.

Changes in the relative silencing activity of BCL-2 siRNA that was preincubated with platinum(II) vs. platinum (IV) species prior to cellular exposure were determined. Various incubation times were examined in order to control the number of Pt-RNA adducts that would be present on the RNAi transcript. The commercially available cationic liposome-based transfection reagent lipofectamine (RNAi-MAX) was utilized for siRNA delivery and various concentrations of platinum to siRNA were first explored (FIG. 6). qRT-PCR of BCL-2 mRNA isolated from MCF-7 or OVCAR4 cells at 24 h after treatment showed ineffective BCL-2 silencing (i.e. >30% of baseline mRNA expression) by siRNA that had be pre-incubated for >3 h with a 1000 fold excess of either OxaPt(II) or CisPt(II) (FIG. 7); the activity of the siRNA was unperturbed by 24 h of exposure to similar concentrations of either OxaPt(IV) or CisPt(IV).

Example 3—Characterization of Nanoparticles

Figure 8:
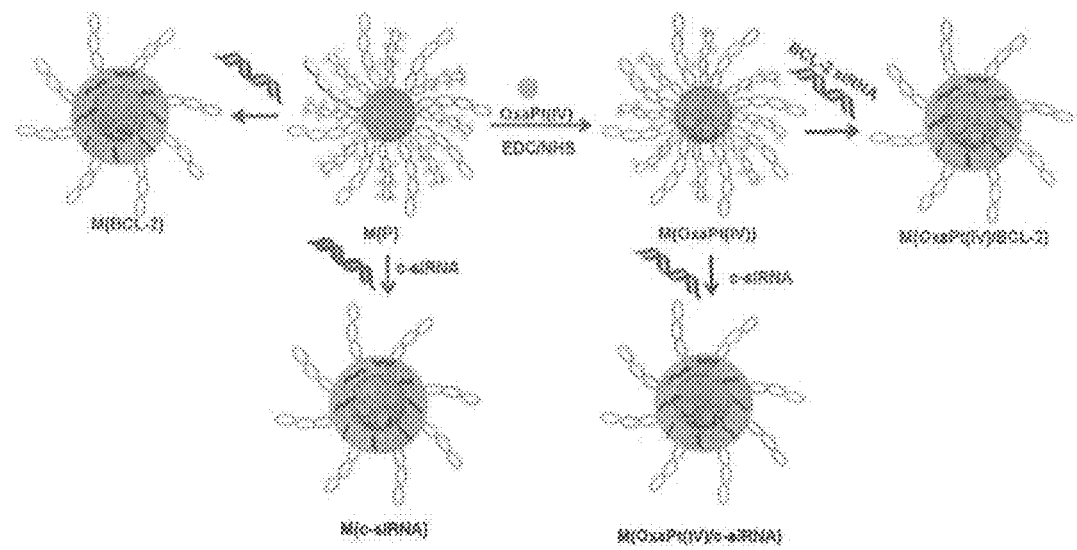
FIG. 8 is a schematic representation of the preparation of various siRNA-loaded micelles. Starting with empty polymer micelles (M(P)), M(c-siRNA) and M(BCL-2) represent micelles that are formed by electrostatic complexation of the mPEG-b-PCL-PLL polymer with either c-siRNA or BCL-2 siRNA, respectively. M(OxaPt(IV)) represent polymeric micelles that are formed after chemical conjugation of the free carboxylic acid moieties of OxaPt(IV) with amines on the surfaces of M(P) in the presence of EDC/NHS reagent. Further electrostatic complexation of these resultant micelles with either c-siRNA or BCL-2 siRNA yields M(OxaPt(IV)/c-siRNA) and M(OxaPt(IV)/BCL-2), respectively.

In order to deliver the largest intracellular concentrations of both siRNA and platinum-based small molecules while preserving their individual and synergistic activities, a transfection reagent comprised of the biodegradable triblock copolymer of methoxyl-terminated poly(ethylene glycol)-block-poly-(ε-caprolactone)-block-poly(L-lysine) (i.e. mPEG$_{114}$-b-PCL$_{25}$-b-PLL$_{25}$; "P") was synthesized. This polymer was designed to self-assemble into micelles with a hydrophobic PCL core and a corona that consisted of hydrophilic mPEG and positively-charged PLL segments (i.e. M(P), where "M" stands for micelles; FIG. 1B). OxaPt (IV) was coupled to the PLL polymer through formation of an amide bond between the carboxyl group of its auxiliary ligand and the free amino group in lysine, forming micelles that contained oxaPt(IV) species (i.e. M(oxaPt(IV)). Similarly, siRNA could be complexed with unreacted PLL chains through electrostatic interactions, forming micelles that contained BCL-2 (i.e. M(BCL-2)) or control siRNA (i.e. M(c-siRNA)) (FIG. 8). Note, both OxaPt(IV) and siRNA species may also be combined in a single micelle construct (i.e. M(oxaPt(IV)/BCL-2) or M(oxaPt(IV)/c-siRNA), respectively), consisting of a hydrophilic mPEG corona, a middle layer comprised of PLL/siRNA, and a hydrophobic core of PCL and PLL-OxaPt(IV) conjugates. In this later construct, the siRNA is protected from platination both through physical separation in different layers of the nanocomplex as well as by utilization of an unreactive platinum(IV) species (i.e. OxaPt(IV)). Each of these constructs was generated to examine its relative utility for protecting the siRNA transcript from platination and subsequent deactivation. Notably, when taken up intracellularly, the platinum species in M(Oxa(IV)) is reduced by ascorbic acid and/or glutathione, liberating free OxaPt(II) only after intracellular siRNA delivery; free oxaPt(II) is then capable of reacting with nuclear DNA (FIG. 1E).

Figures 9A, 9B, 9C:
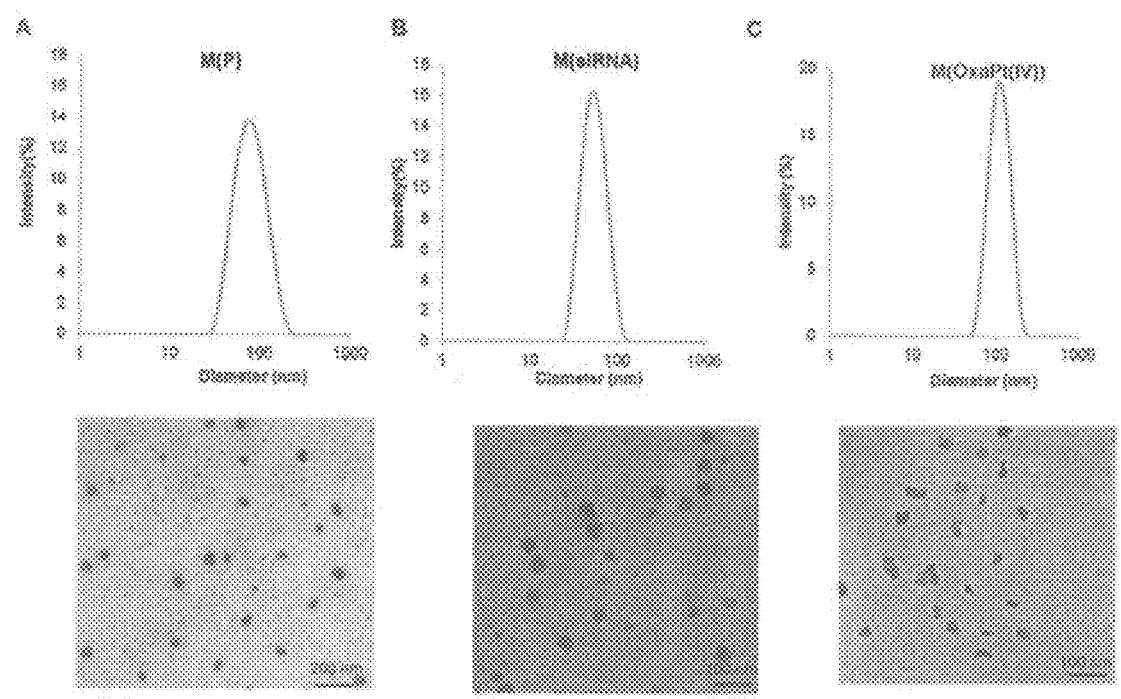
FIG. 9A is a DLS plot (% intensity vs. diameter (nm)) (upper) and a TEM image (lower) of empty polymeric micelles comprised of mPEG-b-PCL-b-PLL in water (i.e. M(P)).
FIG. 9B is a DLS plot (% intensity vs. diameter (nm)) (upper) and a TEM image (lower) of polymeric micelles complexed with BCL-2 siRNA (i.e. M(BCL-2)) in water.
FIG. 9C is a DLS plot (% intensity vs. diameter (nm)) (upper) and a TEM image (lower) of micelles that were chemically conjugated to OxaPt(IV) species (i.e. M(OxaPt(IV)) in water.
Figures 10A, 10B:
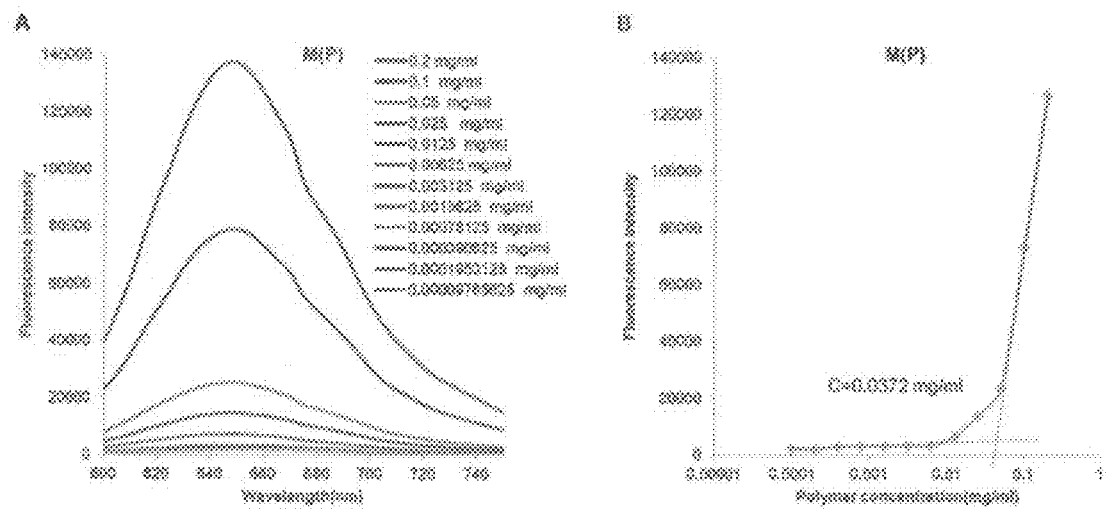
FIG. 10A is a plot of fluorescence intensity as a function of wavelength. These data were detected by Nile Red fluorescence for mPEG-PCL-PLL at various concentrations, which forms M(P) in solution.
FIG. 10B is a plot of fluorescence intensity as a function of polymer concentration (mg/mL). These data were used to determine the critical micelle concentration (CMC) for mPEG-PCL-PLL, which forms M(P) in solution.
Figures 10C, 10D:
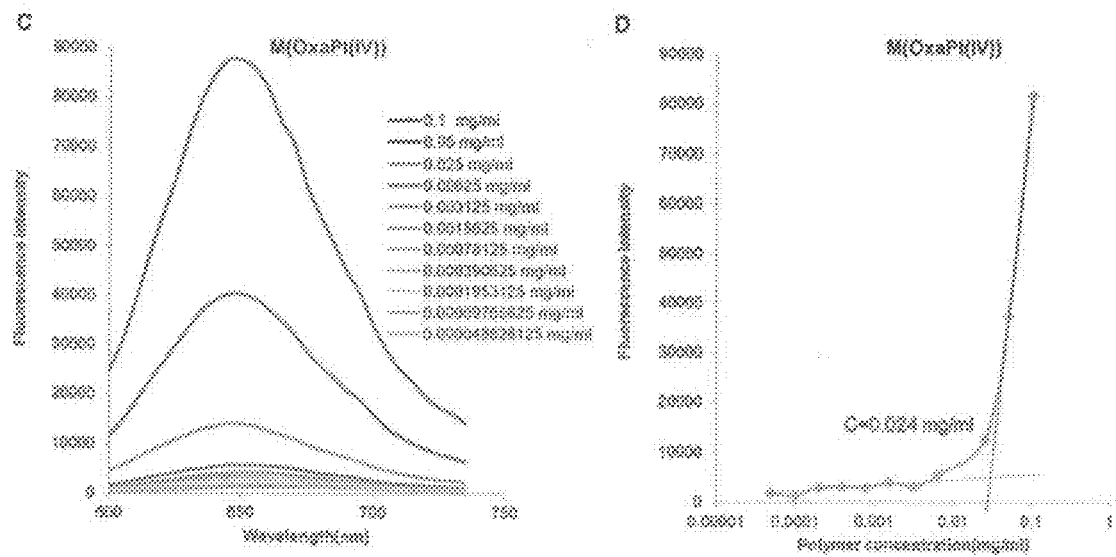
FIG. 10C is a plot of fluorescence intensity as a function of wavelength. These data were detected by Nile Red fluorescence for mPEG-PCL-PLL-OxaPt(IV) at various concentrations, which generates M(OxaPt(IV)).
FIG. 10D is a plot of fluorescence intensity as a function of polymer concentration (mg/mL). These data were used to determine the critical micelle concentration (CMC) for represent analogous plots for mPEG-PCL-PLL-OxaPt(IV), which generates M(OxaPt(IV)).

The $mPEG_{114}$-b-$PCL_{25}$-b-$PLL_{25}$ polymer was found to have a critical micelle concentration (CMC) of 31.9 µg/mL. It formed M(P) with a mean diameter of 70.8+/−0.5 nm (as assessed by DLS) and with a zeta potential of +46.1+/−4.2 mV (FIG. 9). Notably, once coupled to the PLL polymer, the OxaPt(IV) conjugate becomes less water soluble, driving its segregation within the PCL core and leaving unreacted PLL chains in the outer layer of M(OxaPt(IV)); this assertion is supported by experimental evidence that demonstrated a decrease in the CMC from 37 to 24 µg/mL (FIG. 10), an increase in the mean particle diameter to 92.6+/−2.6 nm by DLS, and a reduction in the zeta potential to +34.8+/−1.9 for M(OxaPt(IV)) as compared to M(P) (Table 1).

TABLE 1

Physical characterization of various polymeric micelle compositions

| Samples | Size TEM (nm) | Size DLS (nm) | PDI | Zeta Potential (mV) |
|---|---|---|---|---|
| M(P) | 58.6 ± 6.2 | 70.8 ± 0.5 | 0.196 ± 0.038 | 46.1 ± 4.2 |
| M(BCL-2) | 39.8 ± 7.8 | 55.4 ± 0.7 | 0.265 ± 0.029 | 35.5 ± 0.6 |
| M(OxaPt(IV)) | 41.1 ± 9.5 | 92.6 ± 2.6 | 0.203 ± 0.017 | 34.8 ± 1.9 |
| M(OxaPt(IV)/BCL-2) | 78.9 ± 10.4 | 104.9 ± 2.1 | 0.199 ± 0.018 | 26.6 ± 1.5 |

Figures 11A, 11B, 11C, 11D:
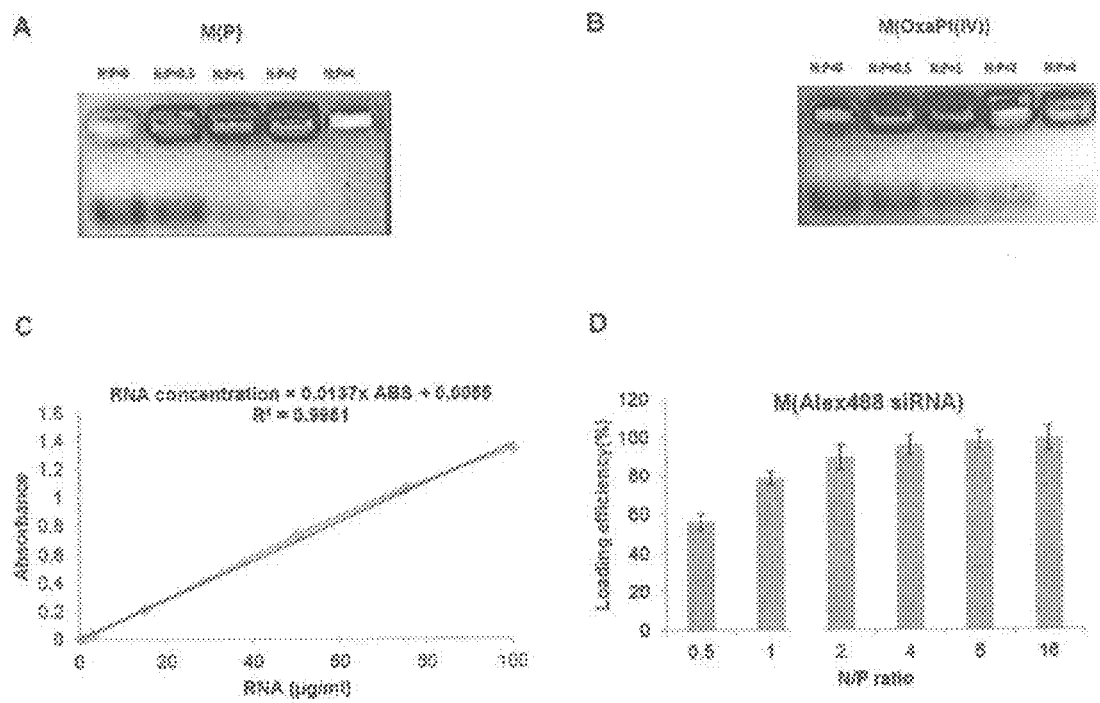
FIG. 11A is an image of a gel. These data show the electrophoretic mobility of siRNA on agarose gels before and after complexation with M(P) at different initial N/P ratios (0, 0.5, 1, 2, and 4 from left to right, respectively).
FIG. 11B is an image of a gel. These data show the electrophoretic mobility of siRNA on agarose gels before and after complexation with M(OxaPt(IV)) at different initial N/P ratios (0, 0.5, 1, 2, and 4 from left to right, respectively).
FIG. 11C is the standard curve (absorbance vs. RNA concentration (μg/mL)) for quantifying siRNA concentrations as a function of Alexa488-labeled siRNA absorbance in solution ($l_{ABS}$=488 nm).
FIG. 11D is a bar graph of the loading efficiency of Alexa488-labeled siRNA to polymer in micelles formed from electrostatic complexation of Alexa448-labeled siRNA and M(P) (i.e. M(Alexa488 siRNA), as a function of the initial N/P ratio from 0.5 to 16.
Figure 11E:
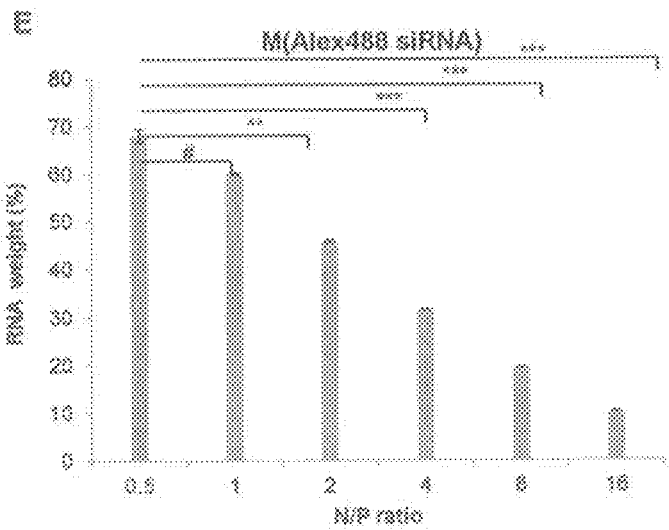
FIG. 11E is a bar graph of the final weight percentage of Alexa488-labeled siRNA to polymer in micelles formed from electrostatic complexation of Alexa448-labeled siRNA and M(P) (i.e. M(Alexa488 siRNA), as a function of the initial N/P ratio from 0.5 to 16. Significance is defined as p<0.01, *p<0.001. Note, # denotes p>0.05.
Figures 12A, 12B, 12C, 12D, 12E, 12F, 12G:
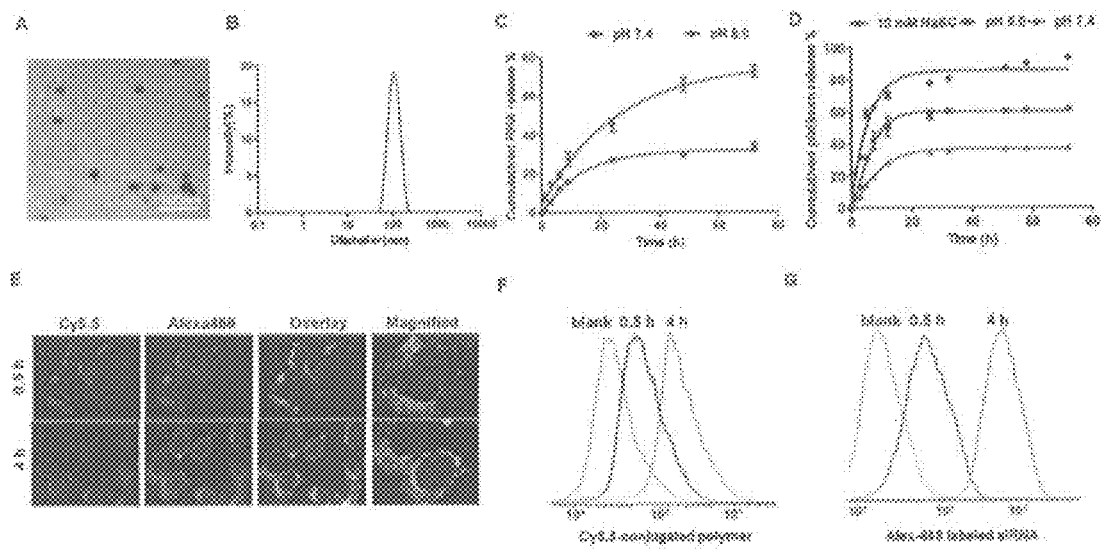
FIG. 12A is a TEM image showing the average size distribution of M(OxaPt(IV)/BCL-2) formed at an amine (monomer unit) to phosphate (nucleic acid) ratio (N/P) of 4. The resultant micelles had a mean particle diameter of 78.9+/−10.4 nm by TEM.
FIG. 12B is a DLS plot (intensity (%) vs. diameter (nm)), which shows the average size distribution of M(OxaPt(IV)/BCL-2) formed at an amine (monomer unit) to phosphate (nucleic acid) ratio (N/P) of 4. The resultant micelles had a mean particle diameter of 104.9+/−2.1 nm by DLS.
FIG. 12C is a plot of the cumulative RNA release (%) as a function of time (h). These data show that the in situ release of free oxaPt(II) species occurs rapidly in reducing environments while a more controlled release profile is observed dependent upon pH.
FIG. 12D is a plot of the cumulative platinum release (%) as a function of time (h). These data show that the in situ release of Alexa488-labeled siRNA loaded on the same micelles as those used to produce the data shown in FIG. 12C; release is slower but similarly pH-dependent.
FIG. 12E is a series of confocal laser scanning microscopy (CLSM) images visualizing cellular uptake and cytoplasmic delivery of M(Cy5.5/OxaPt(IV)/Alexa-488 siRNA). Images were taken at 30 min (upper panel) or at 4 h after incubation of micelles with MCF-7 cells (lower panel); note, cell nuclei are stained with DAPI. Cy5.5-conjugated PEG-b-PCL-b-PLL polymer and Alexa488-labeled BCL-2 siRNA were simultaneously utilized to independently track polymer and RNA species over time (scale bar=100 μm).
FIG. 12F is a plot of the uptake of Cy5.5-conjugated polymer in MCF-7 cells treated with M(Cy5.5/OxaPt(IV)/Alexa488 siRNA), as quantified by flow cytometry. Signals generated from the untreated (blank) cells are included for reference. Data shown are expressed as mean values±standard deviation of the mean (n=3 experimental replicates per condition).
FIG. 12G is a plot of the uptake of Alexa488-labeled BCL-2 siRNA in MCF-7 cells treated with M(Cy5.5/OxaPt(IV)/Alexa488 siRNA), as quantified by flow cytometry.

The reaction of OxaPt(IV) with $mPEG_{114}$-b-$PCL_{25}$-b-$PLL_{25}$ polymer was conducted at an initial molar ratio of 0.6:1 Pt to $NH_2$ groups (on the PLL block). Overall, M(OxaPt(IV)) was found to be comprised of 10 wt % Pt, corresponding to a final oxaliplatin content of 20.4 wt % (as determined by AAS). This degree OxaPt(IV) functionalization would be expected to yield 72% unreacted amine groups on the PLL corona of M(OxaPt(IV)), which would enable further complexation of siRNA through electrostatic interactions. To prove M(OxaPt(IV)) was able to complex with Bcl-2 siRNA, agarose gel electrophoresis experiments were conducted for siRNA after coincubation with either M(P) or M(OxaPt(IV)) (FIG. 11A and FIG. 11B). The results showed that the mobility of siRNA was completely inhibited when electrostatically complexed with M(P) above a N/P ratio (defined as the ratio of nitrogen atoms on the polymer to phosphate units on the siRNA) equal to 2; the mobility of siRNA was similarly reduced when it was complexed with M(OxaPt(IV)) above a N/P=4. Using Alexa488-labeled BCL-2 siRNA, the loading efficiency was found to be approximately 100% and the final micellar composition consisted of 30% RNA by weight (FIG. 11C, FIG. 11D, and FIG. 11E). Representative micelles containing both BCL-2 siRNA and OxaPt(IV) formed at a N/P=4 (i.e. M(OxaPt (IV)/Bcl-2)) exhibited spherical structure with mean particle diameter of 78.9+/−10.4 nm and 104.9+/−2.1 nm by TEM and DLS, respectively (FIG. 12A and FIG. 12B); M(OxaPt (IV)/Bcl-2) had a reduced zeta potential of +26.6+/−1.5 mV as compared to either M(P) or M(oxaPt(IV)) (Table 1), further supporting shielding of free amines on the PLL block by siRNA. M(OxaPt(IV)/BCL-2) demonstrated controlled release of both platinum and siRNA species (FIG. 12C and FIG. 12D). Notably, BCL-2 siRNA was also directly complexed to M(P) to generated M(Bcl-2) with a mean diameter of 55.4+/−0.7 nm (DLS) and a zeta potential of +35.5+/−0.6 mV.

Example 4—siRNA Activity

Different concentrations of luciferase and BCL-2 siRNAs were used to achieve mRNA knockdown of their respective targets in a LUC+MCF-7 cell line. For both M(P) and M(OxaPt(IV)), an N/P=4 was utilized for siRNA complexation. Maximal RNAi was obtained by utilizing 100 nM siRNA (FIG. 13). To better study the mechanisms of nanoparticle uptake, a Cy5.5-labeled PEO-b-PCL-b-PLL polymer was synthesized using EDC/NHS chemistry (FIG. 14). Alexa488-conjugated siRNA was then complexed to micelles comprised of this Cy5.5-labeled polymer (i.e. M(cy5.5/Alexa488 siRNA)) or Cy5.5-labeled polymer and OxaPt(IV) (i.e. M(Cy5.5/OxaPt(IV)/Alexa488 siRNA) to enable independent tracking of both siRNA and polymer species (FIG. 15); M(Cy5.5/OxaPt(IV)/Alexa488 siRNA) was subsequently incubated with MCF-7 cells for different time intervals and the cells were visualized by confocal laser scanning microscopy (CLSM) (FIG. 12E). Flow cytometry was also utilized to quantify intracellular levels of Cy5.5-labeled polymer and Alexa488-siRNA in MCF-7 (FIG. 12F and FIG. 12G) and in OVCAR-4 cells (FIG. 16). Notably, cells that were treated with either M(Cy5.5/Alexa488-siRNA) or M(Cy5.5/OxaPt(IV)/Alexa488 siRNA) showed that the siRNA was distributed throughout the cytoplasm, indicating effective intracellular distribution after endosomal uptake of each micellar construct (FIG. 17).

Example 5—Combining RNAi and Platinum Based Small Molecules

Intracellular platinum delivery and relative BCL-2 silencing efficiency were compared for various combinations of siRNA and oxaliplatin species. MCF-7 cells were treated with different concentrations of either free OxaPt(II), free OxaPt(IV), or M(OxaPt(IV)), either individually or in combination with M(BCL-2) or M(c-siRNA); cells were also treated with micelles that combined siRNA and platinum species in a single nanoparticle construct (i.e. M(OxaPt(IV)/BCL-2) or M(OxaPt(IV)/c-siRNA)). In all cases, BCL-2 mRNA levels were measured by qRT-PCR, intracellular platinum and Pt-DNA adducts were quantified via AAS, and cell viability was determined via MTT assays of cells treated with each combination. For all siRNA containing groups, the concentration of siRNA species was 100 nM, transfected using various mPEG-b-PCL-b-PLL-based micelles formed at an N/P ratio of 8:1, which showed no inherent effects on cellular viability in the absence of platinum species (FIG. 18).

When comparing the intracellular content of platinum after 1 and 4 h of treatment, decreased amounts of free OxaPt(IV) were retained as compared to free OxaPt(II) at each time point (FIG. 19A and Table 2).

TABLE 2

Quantification of platinum uptake (pg Pt/cell) over time (at 1 and 4 h) and the amount of Pt-DNA adducts formed in MCF-7 cells at 24 h after treatment with various combinations of oxaliplatin species and/or siRNA.

| Treatment groups | Platinum uptake (pg Pt/cell) | | Pt-DNA adducts (ng Pt/μg DNA) |
|---|---|---|---|
| | 1 h ($\times 10^{-4}$) | 4 h ($\times 10^{-4}$) | After 24 h |
| OxaPt(II) | 369 ± 24 | 535 ± 16 | 41.10 ± 9.84 |
| OxaPt(II) + M(c-siRNA) | 194 ± 51 | 395 ± 123 | 28.84 ± 6.70 |
| OxaPt(II) + M(BCL-2) | 194 ± 40 | 256 ± 62 | 25.98 ± 7.16 |
| OxaPt(IV) | 180 ± 20 | 205 ± 38 | 29.10 ± 9.80 |
| OxaPt(IV) + M(c-siRNA) | 57 ± 18 | 186 ± 45 | 32.42 ± 8.03 |
| OxaPt(IV) + M(BCL-2) | 77 ± 21 | 138 ± 11 | 35.9 ± 11.20 |
| M(OxaPt(IV)) | 1338 ± 20 | 2572 ± 169 | 225.40 ± 23.54 |
| M(OxaPt(IV)) + M(c-siRNA) | 686 ± 23 | 1720 ± 469 | 138.90 ± 17.42 |
| M(OxaPt(IV)) + M(BCL-2) | 488 ± 45 | 1440 ± 102 | 134.20 ± 17.97 |
| M(OxaPt(IV)/c-siRNA) | 1286 ± 34 | 2760 ± 156 | 214.48 ± 21.79 |
| M(OxaPt(IV)/BCL-2) | 1494 ± 28 | 2480 ± 122 | 245.30 ± 32.53 |

The intracellular levels were markedly enhanced by using M(OxaPt(IV)) as opposed to various free drug formulations of oxaliplatin. Co-administration of M(OxaPt(IV)) with a separate nanoparticle construct containing micellar-complexed siRNA (e.g. M(BCL2)), however, resulted in a relative decrease in the intracellular content of platinum as compared to M(OxaPt(IV)) or administration of M(OxaPt(IV)/BCL2); these results would support a saturated limit for nanoparticle uptake at each time point. This phenomena were further supported by measurements of the numbers of intracellular Pt-DNA adducts that could be detected after 24 h of treatment (FIG. 19B and Table 2). A markedly enhanced number of adducts were obtained after treatment with M(OxaPt(IV)) as opposed to either free OxaPt(II) or free OxaPt(IV). Co-administration of two separate nanoparticle constructs of M(BCL-2) and M(OxaPt(IV)) resulted in fewer Pt-DNA adducts as opposed to M(OxaPt(IV)) or M(OxaPt(IV)/BCL-2)), again supporting a saturated limit for nanoparticle uptake by MCF-7 cells. The relative BCL-2 mRNA levels within the cells after 24 h of treatment with each experimental group were also examined (FIG. 19C and FIG. 20). While all platinum-containing treatments were able to decrease BCL-2 levels, consistent with the known pro-apoptotic effects of oxaliplatin, maximal mRNA suppression was achieved with BCL-2 siRNA treatment. Co-administration of free OxaPt(II), free OxaPt(IV) or M(OxaPt(IV)) along with M(BCL-2) did not further inhibit mRNA levels beyond those that were obtained with M(BCL-2) treatment alone. Notably, co-incorporation of BCL-2 siRNA and OxaPt(IV) in the same nanoparticle construct (i.e. M(OxaPt(IV)/BCL-2)) did achieve a statistically significant improvement in BCL-2 mRNA knockdown. Given the results described above with Alexa488-labeled siRNA delivery, this would again indicate that incorporation of siRNA and OxaPt(IV) species in a single nanoparticle construct not only ensures transcript stability but further results in maximal RNAi activity.

Ultimately, the goals of combining RNAi with platinum-based therapies are to explore changes in treatment responses and biological activity mediated by suppression of specific gene products. As such, changes in MCF-7 cellular viability upon in vitro treatment with various experimental combinations of oxaliplatin species and BCL-2 siRNA were also investigated. Changes in cellular viability as a function of increasing quantities of free OxaPt(II), free OxaPt(IV), or M(OxaPt(IV)), either as single treatments or in combinations with either M(BCL-2) or M(c-siRNA) were measured (FIG. 19D and FIG. 21); cells were also treated with M(OxaPt(IV)/BCL-2) and M(OxaPt(IV)/c-siRNA) at equivalent platinum concentrations for comparison. Synergistic treatment responses from any of the combinations of siRNA and oxaliplatin species were defined as a decrease in the $IC_{50}$ as compared to cells that were exposed to the same platinum therapy alone. While combinations of free OxaPt(IV) with M(BCL-2) did show synergistic treatment effects, which were not obvious in similar combinations with free OxaPt(II) species, free OxaPt(IV) treatments were approximately 10-fold less potent at inducing cellular toxicity (FIG. 19E). Much of this activity was restored by combining M(BCL-2) with M(OxaPt(IV)) instead of employing free OxaPt(IV). Notably, the highest potency and synergistic activity were obtained from M(OxaPt(IV)/BCL-2), which was corroborated by testing the various treatment combinations on additional cell lines (i.e. OVCAR4, A2780 and A2780DDP; Table 3).

TABLE 3

Summary of $IC_{50}$ values (μM) for MCF-7, OVCAR4, A2780 and A2780DDP cells treated with various combinations of oxaliplatin species and/or siRNA.

| Treatment groups | MCF-7 | OVCAR4 | A2780 | A2780DDP |
|---|---|---|---|---|
| OxaPt(II) | 23.05 ± 0.25 | 15.45 ± 0.50 | 2.90 ± 0.28 | 18.80 ± 0.99 |
| OxaPt(II) + M(c-siRNA) | 28.51 ± 0.34 | 21.60 ± 0.71 | 3.75 ± 0.91 | 22.25 ± 1.63 |
| OxaPt(II) + M(BCL-2) | 19.20 ± 0.42 | 9.24 ± 1.50 | 1.60 ± 0.14 | 10.55 ± 1.34 |
| OxaPt(IV) | >100 | >100 | 15.85 ± 2.76 | >100 |
| OxaPt(IV) + M(c-siRNA) | >100 | >100 | 8.60 ± 1.13 | >100 |
| OxaPt(IV) + M(BCL-2) | >100 | >100 | 12.65 ± 1.20 | >100 |
| M(OxaPt(IV)) | 0.54 ± 0.03 | 1.79 ± 0.10 | 0.87 ± 0.13 | 1.45 ± 0.07 |
| M(OxaPt(IV)) + M(c-siRNA) | 0.43 ± 0.01 | 1.37 ± 0.12 | 0.72 ± 0.09 | 1.06 ± 0.20 |
| M(OxaPt(IV)) + M(BCL-2) | 0.17 ± 0.02 | 0.43 ± 0.01 | 0.51 ± 0.03 | 0.60 ± 0.08 |
| M(OxaPt(IV)/c-siRNA) | 0.43 ± 0.02 | 1.80 ± 0.25 | 0.59 ± 0.06 | 0.72 ± 0.05 |
| M(OxaPt(IV)/BCL-2) | 0.06 ± 0.01 | 0.12 ± 0.01 | 0.39 ± 0.02 | 0.42 ± 0.08 |

To investigate the biological mechanisms underlying this improved cytotoxicity, we next performed flow cytometry analyses for apoptosis on MCF-7 cells after 24 h of treatment with each combination therapy (FIG. 19F and FIG. 22). These experiments confirmed that M(OxaPt(IV)/BCL-2) induced the highest fractions of both early and late apoptotic events as compared to all other strategies for combining siRNA and oxaliplatin (FIG. 22).

Example 6—Preparation of Polymer

Synthesis of PEG-Block Precursor

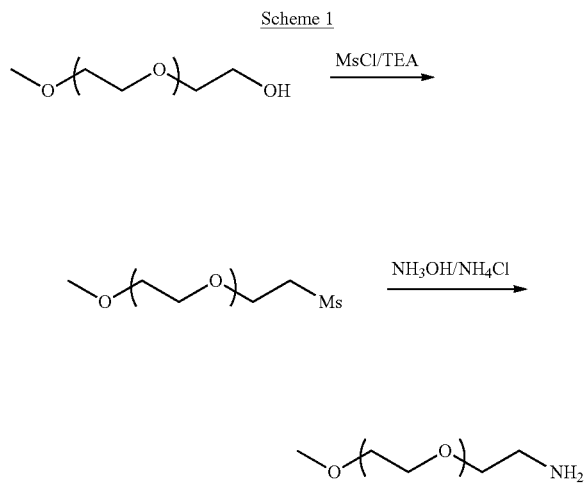

To 30 mL DCM with mPEG5000 (10 g, 2 mmol) was added TEA (0.7 ml) and MsCl (0.3 ml, 2 equiv.) at zero degree. The mixture was stirred overnight and precipitated by large amount of ether. The filtered product was dissolved in 100 ml ammonia/NH$_4$Cl under stirring for 3 days. Then the solution was exacted by DCM, washed by water and brine, dried by MgSO$_4$, and precipitated by ether to get the amino-functionalized mPEG.

Synthesis of Lyz(Z)-NCA

Lys(Z) (5 g) was dried with P2O5 under vacuum by oil pump over 0.5 h, suspended in freshly anhydrous THF (100 mL) under nitrogen protection, and heated to 50° C. A solution of triphosgene (3 g) in dry THF (10 mL) was added in. After reaction at 50° C. for 2 h, the solution became completely clear. The mixture was cooled to room temperature, and purged with nitrogen for 0.5 h to remove extra HC. To the residue with a volume of 200 mL was slowly added hexane, the precipitation was resolve by ethyl acetate and washed by cold NaHCO$_3$aq. and water. And then, the ethyl acetate was removed by rotate evaporator, the NCA achieved was soluble in 10 ml THF in 40° C. and add 5 ml of hexane and resoluble in 60° C., and then cold to room temperature.

On the next morning, the supernatant was removed. The snow-shaped NCA crystals were filtered, rinsed with copious ether, and dried under vacuum by oil pump, repeat the circles for three times.

Synthesis of BLA-NCA

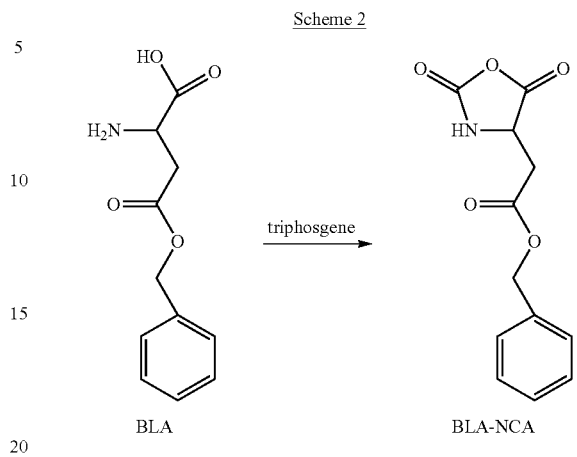

BLA (5 g) was dried with P2O5 under vacuum by oil pump over 0.5 h, suspended in freshly anhydrous THF (100 mL) under nitrogen protection, and heated to 50° C. A solution of triphosgene (3 g) in dry THF (10 mL) was added in. After reaction at 50° C. for 3 h, the solution became completely clear. The mixture was cooled to room temperature, and purged with nitrogen for 0.5 h to remove extra HC. To the residue with a volume of 200 mL was slowly added hexane, the precipitation was resolve by ethyl acetate and washed by cold NaHCO$_3$aq. and water. And then, the ethyl acetate was removed by rotate evaporator, the NCA achieved was soluble in 10 ml THF in 40° C. and add 5 ml of hexane and resoluble in 60° C., and then cold to room temperature.

On the next morning, the supernatant was removed. The snow-shaped NCA crystals were filtered, rinsed with copious ether, and dried under vacuum by oil pump, repeat the circles for three times.

Synthesis of mPEG-PZLL

The Lys(Z) NCA was dissolved in anhydrous DMF with PEG-NH2. The mixture was stirred in 30 degree for 4 days followed by precipitating in ether to get PEG-PZLL.

Synthesis of mPEG-PZLL-PBLA

The Asp(Bzl) NCA was dissolved in anhydrous DMF with PEG-PZLL-NH2. The mixture was stirred in 30 degree for 4 days followed by precipitating in ether to get PEG-PZLL-Pasp(Bzl).

Synthesis of mPEG-PZLL-PAspatamine

Briefly, PEG-PZLL-PBLA was dissolved in NMP containing 1 M thiourea at 35 degree and cooled to 4 C. Next, DET (0.6 mL, 50 equiv. To Bzl groups) was diluted with NMP/thiourea (1.2 mL) and PEG-PZLL-PBLA solution was added dropwise into the DET solution. The mixture was stirred for 1 h at 15 C under argon atmosphere. Then, the reaction mixture was added drop wise into ice-cold 5 M HCl (5 mL) for neutralization. The polymer product was purified by dialysis against 0.01 M HCl overnight and then deionized water for 3 days at 4 C. The dialyzed solution was lyophilized to obtain the final product.

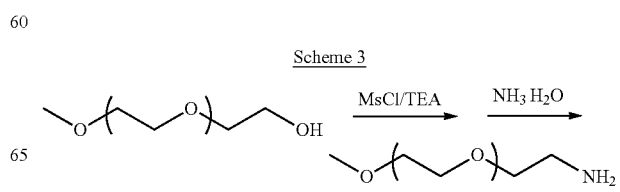

-continued

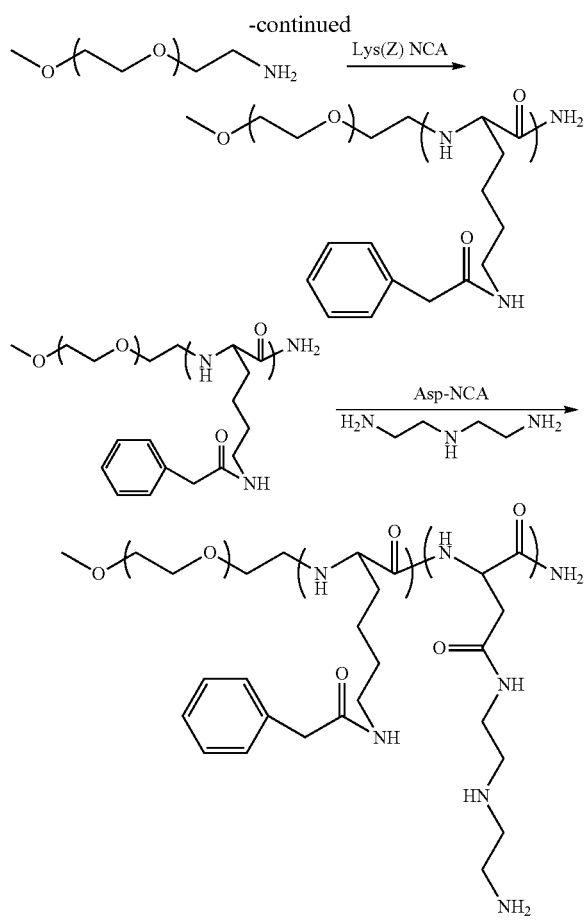

Synthesis of mPEG-PLL-OTC mPEG-PLL was dissolved in NaHCO3 Buffer (pH 9), Cis-aconitic anhydride (10 equiv. to amine group) was added dropwise and stirred for 24 h. The reaction system was dialysis against water for 3 days and lyophilized to get mPEG-PLL-OTC.

Example 7—Formation of Core/Shell Compositions

Positively charged nanoparticles (e.g., PEO-PCL-PLL or PEO-PBzLL-PASP) may be coated with negatively charged diblock copolymers (e.g. PEO-b-PGA). See FIGS. 23A, 23B, 24A, 24B, 25A, 25B, 26A, and 26B.

Example 8—Delivery of CRISPR/CAS9 with Small Molecule Chemotherapeutics

FIGS. 27-30 show data indicating that CRISPR/Cas9 components may be delivered to cells, with or without co-delivery of platinum. Details of the experiments for obtaining these data are summarized in the Brief Description of the Figures for FIGS. 27-30.

Example 9—Combined Delivery of CRISPR/Cas9 and Small Molecule Anticancer Agents

Methods

Chemical and RNA Species: Cisplatin (Pt(II)) was purchased from ChemiChem International Development Co., Ltd (Shenzhen, China). Other small molecule anticancer agents, including doxorubicin, gemcitabine, camptothecin (CPT) and melphalan, as well as the various small molecule inhibitors of cellular uptake, including wortmannin (WNM), sodium azide (NaN3), methyl-1-cyclodextrin (MCD), chlorpromazine (CL) and genistein (Gen) were purchased from Sigma-Aldrich; these reagent grade chemicals and all solvents were used without further purification. Pt(IV), Pt(IV)-OH and Pt(IV)-COOH prodrugs were synthesized from Pt(II); their structural properties were verified by $^1$H NMR, $^{13}$C NMR and by ESI-MS. The purity of Pt(IV) was verified by high-performance liquid chromatography (HPLC). Cas9 mRNA, Cy5-labeled EGFP mRNA and various sgRNA were purchased from TriLink Biotechnology, Inc. (FIG. 34); Cy5.5-labeled Cas9 mRNA was synthesized de novo using EDC/NHS chemistry. Reagents utilized for conjugation, including N-hydroxysuccinimide (NHS), 1-(3-dimethyl aminopropyl)-3-ethylcarbodiimide hydrochloride (EDC-HCl), as well as the reducing agent sodium ascorbate (NaSC) were purchased from Sigma-Aldrich; fluorescent labels, including FITC, 5-FAM-NHS, and Cy5.5-NHS, were obtained from Luminiprobe INC. The Annexin V-FITC Apoptosis Detection Kit (ab 14085, Abcam) was used for the cellular apoptosis assay.

General measurements: NMR, ESI-MS and MALDI/TOF MS were performed to characterize the various platinum(IV) prodrugs and to monitor the reactions of different small molecule anticancer agents with sgRNA. Briefly, $^1$H and $^{13}$C spectra at room temperature were measured at 400 and at 100 MHz, respectively, using a Bruker NMR spectrometer (Bruker Corporation, Billerica, Mass.). MS measurements were performed on a Quattro Premier XE system equipped with an electrospray interface (ESI-MS; Waters, Milford, Mass.) and with a matrix-assisted laser-desorption ionization and time-of-flight MS (MALDI/TOF MS) machine (Bruker model MicroFlex). Dynamic light scattering (DLS) and zeta potential measurements of nanoparticle suspensions were conducted using on a Zetasizer Nano ZS90; transmission electron microscope (TEM) images of the same suspensions were obtained with a JEOL-1100 Transmission Electronic Microscope at 200 kV and with negative staining. The critical micelle concentrations (CMCs) of various nanoparticle suspensions were determined by the Nile red assay. UV-vis and fluorescence measurements were performed for Cy5.5-labeled mRNA loading and release from nanoparticles as well as to quantify levels within treated cellular populations, using an Infinite® M200 Pro microplate reader (Tecan Systems, Inc., CA, USA). Graphite furnace atomic absorption spectroscopy (GFAAS) measurements were conducted to determine Pt levels in cells as well as in excised tissue samples, using an AAnalyst 600 GFAAS instrument (Perkin Elmer, Waltham, Mass.). Inductively coupled plasma mass spectroscopy (ICP-MS; ICP-MS 7900 instrument, Agilent Technologies, CA, USA) was performed for quantification of trace Pt levels and to determine the amounts of intracellular Pt-DNA adducts in cancer cells.

Cell Culture: A2780 (Pt(II)-sensitive), A2780DDP (Pt(II)-resistant), SKOV3 (human ovarian cancer), COV362 (human ovarian cancer), OVCAR4 (human ovarian cancer), and OVSAHO (human ovarian cancer) cell lines were obtained from ATCC and cultured at 37° C., 5% CO2 in RPMI 1640 supplemented with 10% fetal bovine serum (FBS, Gibco) and 1% penicillin/streptomycin (Corning, USA). Obtained from the laboratory of Dr. David Pepin under an IRB approved protocol (MGH), primary cells (ptAM-sph) were collected from the ascites of a patient with advanced-stage and "platinum-resistant" HGSOC49. Cell pellets from ascites were first plated in regular flasks for 24 h; and, non-adherent cells were collected and transferred into new ultra-low attachment flasks. The resultant spheroid cultures were passaged by dissociation and diluted 1:10 for at least 5 passages to derive stable homogenous cell lines. The primary cell lines were maintained in RPMI-1640 supplemented with 1% MEM-NEAA (Life technologies, USA), 2% B-27 (Gibco, USA), 1% insulin-transferrin-selenium (Gibco, USA) and 1% penicillin/streptomycin (Corning, USA).

Generation of Cas9- and luciferase-expressive cells through lentiviral labeling: To generate the lentiviral vectors encoding for either Cas9 or firefly luciferase (LUC), cDNA was first amplified from their respective plasmids and inserted into lentiviral vectors under the control of the SV40 promoter. The vectors were transfected into the 293T cell line by the calcium method to produce the lentiviral particles. SKOV3 and primary patient-derived ovarian cancer cells were then infected twice within a 48 h period with PEG-it-concentrated viral particles (10 mL) containing the respective Cas9 or LUC-expressive plasmids; puromycin selection of transduced cells ensued for an additional 7 days period; and, finally, FACS-GFP sorting was conducted to create cell lines that stably expressed either the Cas9 or LUC protein.

Activity of sgRNA after incubation with various small molecule anticancer agents: To determine the effects of platination or alkylation of sgRNA on silencing efficiency, SMAD4 sgRNA was first pre-incubated with various small molecules including Pt(II), Pt(IV)-COOH, doxorubicin, gemcitabine, camptothecin, or melphalan for either 12 h or 24 h, at 37° C., and at a drug to sgRNA molar ratio of 10:1 in RNase free water. The sgRNA was then purified by ultracentrifugation (Mw=3 kDa) and quantified by Nanodrop. The RNAi-MAX (Invitrogen, Thermo-fisher, USA) was utilized to transfect the reacted sgRNA (10 nM) into Cas9-expressing SKOV3 cells in 6-well plates. After 72 h, protein was recovered from cell lysates and analyzed by WB to quantify SMAD4 and GAPDH (product of a housekeeping gene; control) levels with respect to those of untreated cells. In addition, to compare the effects of Pt(II) and Pt(IV)-COOH interference with sgRNA-mediated recognition and target gene silencing by Cas9, various incubation periods were examined (i.e. 3, 6, and 9 h).

Determination of the reactions of sgRNA with anticancer agents by MALDI/TOF MS: A 20-mer of RNA comprising the seed region of SMAD4 sgRNA (s-SMAD4) was mixed with Pt(II), Pt(IV)-COOH, doxorubicin, gemcitabine, camptothecin or melphalan at a molar ratio of 1:10 in RNase free water (RNA final concentration (10 µM); small molecule (100 µM)). The reaction mixture was shaken in a 37° C. incubator for a prescribed time interval (30 min, 1 h, 3 h, 6 h, 9 h, 12 h, or 24 h); and, 10 µL of each solution was analyzed by MALDI/TOF MS (positive mode), employing hydroxipicolinic acid as the matrix.

Nanoparticle fabrication: mPEG-b-PZLL-b-PASP(DET) was synthesized de novo. $^1$H-NMR spectroscopy measurements provided the structure of the final construct as mPEG$_{114}$-b-PZLL$_{25}$-b-PAS$_{30}$(DET); the subscript denotes the degree of polymerization of each individual monomer in a given block; and, this triblock copolymer is hereafter abbreviated as "P". Aqueous dispersion of P resulted in the generation of a mono-disperse nanoparticle (NP) suspension. For chemical coupling to P, Pt(IV) (26 mg) was first dissolved in dry DMF (10 mL); EDC (19 mg) and NHS (12 mg) were subsequently added; and, the mixture was stirred for 30 min. A solution of water (0.5 mL) and P (100 mg) was then mixed with N,N-Diisopropylethylamine (DIEA) (10 µL) and stirred for 12 h at 4° C. Afterwards, the mixtures was dialyzed against milli-Q water for 72 h and at 4° C. to obtain Pt(IV)-conjugated nanoparticles (NP(Pt(IV)). Note, P was also modified by conjugation to various fluorophores, including Cy7.5-NHS, Cy5.5-NHS or iFluor™ 405-NHS, that were added to aqueous suspensions of either NP or NP(Pt(IV)) at a 1:10 mass ratio; the reaction mixtures were stirred for 12 h followed by dialysis against milli-Q water for 3 additional days and at 4° C.

For electrostatic complexation of various RNA species, NP or NP(Pt(IV) suspensions were diluted to different final concentrations. Equal volume solutions containing the various mRNA (e.g. Cas9, Cy5.5-Cas9 or Cy5-EGFP) and sgRNA species (e.g. SMAD4, sg1, sg2, sg3, VIM, ESR1, or scramble) in RNase free water were then mixed with these nanoparticle suspensions. The N/P ratios at which the polymer and RNA species were combined varied from 8 to 16. The formed complexes were allowed to stand at room temperature for 30 min to generate the RNA-bound nanoparticles (e.g. NP(Cas9,sgRNA) and NP(Pt(IV);Cas9, sgRNA). The complexation of RNA to the nanoparticles was verified through a gel retardation assay and the rates of release of both RNA and Pt(IV) species were measured in different in situ environments (vide supra). Electrostatic complexation of Cy5-EGFP or Cy5.5-Cas9 resulted in labeled nanoparticles in which the mRNA species could be independently monitored by in vitro and/or in vivo fluorescence imaging. To generate coated nanoparticles with neutral surface charge for in vivo applications, a concentrated solution of mPEG-b-poly(glutamic acid) (mPEG-b-PGA) was added to the platinum-conjugated and/or RNA-complexed nanoparticles at a molar ratio of 1:1 mPEG-b-PGA to P. The sizes of the resultant nanoparticles (e.g. CNP(Pt(IV)) and CNP(PT(IV);Cas9,sg1)) were verified by TEM and DLS; neutralization of their surface charge was further confirmed (i.e. the neutral charge of CNP(Pt(IV) as compared to the cationic charge of NP(Pt(IV)).

Preparation and characterization of Pt(IV)-loaded and/or RNA-complexed nanoparticles: Detailed descriptions of nanoparticle fabrication, verification of RNA complexation, and evaluation of the rates of release of both RNA and Pt(IV) species in different in situ environments may be found elsewhere in this specification). A summary of the various nanoparticle formulations may be found in FIG. 35.

Visualization of the cellular uptake of nanoparticles by confocal laser scanning microscopy and by flow cytometry: SKOV3 and A2780 cells (5×10$^5$ cells/well) were seeded in 6-well plates and were placed in a 37° C. incubator for 12 h. Cells were treated with various nanoparticle (NP) formulations, including NP(Pt(IV),Cy5.5) (for tracking of core nanoparticles), NP(FITC,Pt(IV);Cy5-EGFP mRNA, sgRNA) (for mRNA uptake and release studies), CNP (iFluro™ 405,Pt(IV);Cy5-EGFP mRNA,sgRNA) (for monitoring mRNA expression and nanoparticle co-localization), and CNP(iFluro™ 405,5-FAM,Pt(IV);Cy5.5-Cas9 mRNA, sgRNA) (for intracellular localization of core-shell nanoparticles with respect to mRNA). The cells were then washed prior to confocal laser scanning microscopy or flow cytometry analysis. To determine the pathways that were utilized for intracellular uptake of the nanoparticles, multiple endocytosis inhibitors were subsequently added, including sodium azide (NaN$_3$, 120 µm; general endocytosis), genistein (gen, 200 µg/mL; clathrin-independent endocytosis), chlorpromazine (CL, 20 µg/ml; clathrin-dependent endocytosis), wortmannin (WMN, 0.2 µM; macropinocytosis), or methyl-3-cyclodextrin (MCD, 200 µM; caveolae-dependent endocytosis). Cells were then tested by flow cytometry as previously described.

Initial cellular viability screens to determine the activity of NP(Pt(IV)) on various ovarian cancer cell lines: A2780, A2780DDP, SKOV3, OVCAR4, COV362, and OVSAHO were seeded at 5,000 cells/well; cisplatin (Pt(II)) or nanoparticle-conjugated Pt(IV) (NP(Pt(IV))) were incubated with the cells at different concentrations; and cellular viability was assessed after 72 h using the calorimetric MTT assay. Primary ovarian cancer cells were similarly placed in suspended cultures at a density of 10,000 cells/mL; Pt(II) and NP(Pt(IV)) were added to equivalent final concentrations of Pt and allowed to incubate with the cells for 72 h; and, the CCK8 colorimetric assay was utilized to determine relative viability thereafter.

Comparisons of the rates of uptake and the numbers of Pt-DNA adducts that are formed after the addition of Pt(II) vs. NP(Pt(IV)) to various cell lines: A2780, A2780DDP, SKOV3, and primary ovarian cancer cells were seeded in 6-well plates at a density of 2 million cells/well. Pt(II) and NP(Pt(IV)) were subsequently added to an equivalent final concentration of Pt (40 µM) and were allowed to incubated with the cells for 1, 3 or 7 h. All cells were then washed with PBS. 2 mL of $HNO_3/H_2O_2$ (v:v=1:1) were added to each well and allowed to incubate overnight. Finally, the recovered suspensions was diluted with 3% $HNO_3$:$H_2O$ (2 mL) and the Pt content in each sample was quantified by ICP-MS. For determination of the numbers of intracellular Pt-DNA adducts as a function of cellular treatment, SKOV3 and primary ovarian cancer cells were treated with cisplatin and NP(Pt(IV)) at an equivalent final concentration of Pt (40 µM) for 24 h. The cellular DNA was then extracted using a DNAzol kit (Thermo Fischer Scientific, USA), purified, and quantified by Nanodrop 2000 (Thermo Fischer Scientific, USA). The associated Pt content on a per mass basis of DNA was subsequently enumerated by ICP-MS.

Cellular migration and invasion assays: Cas9 mRNA (1 nM) and SMAD4 sgRNA (10 nM) were complexed with nanoparticles at a N/P ratio of 16 and transfected into SKOV3 and A2780 cells. After 72 h, transfected cells were harvested and 2×105 cells were subjected to a Boyden chamber with 8.0-µm pore membrane to check the migratory activity upon a chemotaxis of FBS from 0% to 10%50. A similar approach was used for the invasion assay, except that the Boyden chambers were pre-coated with 150 µg of Matrigel (BD Biosciences, Maryland, USA). At the completion of the assays, the cells on the lower surfaces of the membranes were stained with 0.05% crystal violet and counted under bright-field microscopy (Olympus Corp., Tokyo, Japan). Experiments were repeated in triplicate and the reported results are representative of subsequent runs.

Immunofluorescence (IF) staining: Cells were plated on glass coverslips and fixed with 4% paraformaldehyde for 20 min prior to permeabilization, using 0.1% Triton X-100 in PBS for 15 min. An Odyssey® Blocking Buffer (PBS) (LI-COR, P/N 927-40000) was applied for 1 h at room temperature. Immunostaining signals and DAPI-stained nuclei were analyzed (Fluoview Software, V4.3, Olympus) by confocal microscopy (FLV 1200; Olympus) at 10× magnification, using a 0.30 NA objective lens (Olympus).

Cytotoxicity assays: SKOV3, A2780, or primary ovarian cancer cells were seeded at a density of 2×103 cells/well in 96-well plates with 150 µL of RPMI1640 supplemented with 10% FBS. After 24 h, the cells were treated with cisplatin (Pt(II)), nanoparticle-complexed Cas9 mRNA and BCL-2 sgRNA (i.e. NP(Cas9;sg1) and NP(Cas9;sg3)) or their combinations at escalating concentrations of Pt; nanoparticle-conjugated Pt(IV) alone (NP(Pt(IV)) or after further complexation with BCL-2 sgRNA (i.e. NP(Pt(IV);Cas9;sg1) or NP(Pt(IV);Cas9;sg3)) were also compared. In all cases, Cas9 mRNA (1 nM) and sgRNA (10 nM) were complexed with nanoparticles at an N/P ratio equal to 16. After 72 h of incubation with each treatment, cellular viability was measured, using the Cell-Titer Blue Assay and by following the manufacturer's instructions (Promega). All experiments were conducted in triplicate. For primary ovarian cancer cells, a density of 10,000 cells per well was utilized; and, cellular viability was measured by the CCK8 assay. The same cell numbers and treatment schedules were employed for the colony formation assay except that the SKOV3 or A2780 cells were seeded sparsely in 6-well plates and treated to a final equivalent concentration of Pt (1 µM for SKOV3 and 0.1 µM for A2780). At 7 or 14 days after treatment, colonies were fixed, using 75% ethanol for 30 min; and, they were subsequently stained with Giemsa solution (Fisher Scientific).

Apoptosis assay: Cells were seeded in 6-well plates (2×10$^5$ cells/well) and incubated with cisplatin (Pt(II)), nanoparticle-complexed Cas9 mRNA and BCL-2 sgRNA (i.e. NP(Cas9;sg1) and NP(Cas9;sg3)) or their combinations; nanoparticle-conjugated Pt(IV) alone (NP(Pt(IV)) or after further complexation with BCL-2 sgRNA (i.e. NP(Pt(IV);Cas9;sg1) or NP(Pt(IV);Cas9;sg3)) were also compared. Each treatment was added to the media to a final equivalent concentration of Pt (10 µM for SKOV3 and 2 µM for A2780). In all cases, Cas9 mRNA (1 nM) and BCL-2 sgRNA (10 nM) were complexed with nanoparticles at a fixed N/P ratio of 16; and, non-treated cells were used as a control. After 48 or 72 h of incubation with each treatment group, the cells were harvested using trypsin. The Annexin V-FITC Detection Kit (BD Biosciences) was used to determine the fraction of cells undergoing apoptosis using flow cytometry. Cells were stained according to the manufacturer's protocol and subject to fluorescence-activated cell-sorting (BD). Data were analyzed using the Modfit software (BD).

Western blotting (WB): Cells were seeded in 6-well plates (1×10$^6$ cells/well) and incubated with cisplatin (Pt(II)), nanoparticle-complexed Cas9 mRNA and BCL-2 sgRNA (i.e. NP(Cas9;sg1) and NP(Cas9;sg3)) or their combinations; nanoparticle-conjugated Pt(IV) alone (NP(Pt(IV)) or after further complexation with BCL-2 sgRNA (i.e. NP(Pt(IV);Cas9;sg1) or NP(Pt(IV);Cas9;sg3)) were also compared. In all cases, the platinum-containing treatments were added to the media to a final equivalent concentration of Pt (10 µM for SKOV3 and 2 µM for A2780); Cas9 mRNA (1 nM) and sgRNA (e.g. SMAD4 or BCL-2; 10 nM) were complexed with nanoparticles at a fixed N/P ratio of 16; and, non-treated cells were used as a control. After 72 h of incubation, total protein was extracted from the entire culture (i.e. from both adherent and floating cells) and subjected to immunoblot analysis. The following primary antibodies were used: SMAD4 (Santa Cruz), BCL-2, cleaved-PAPR1, cleaved-Caspase3, GAPDH (Cell Signaling Technology), and β-actin (Sigma Aldrich).

Animal Handling: All animal studies were performed under protocols approved by the MIT CAC (0615-069-1) and by the Massachusetts General Hospital IACUC (2009N000117).

Toxicity (MTD) study: BALB/c mice at 4-6 weeks old were purchased from Taconic Bioscience and were administered one of the following treatments by IP injection: cisplatin (Pt(II); at either 1.75 or 3.5 mg/kg of Pt), core-shell nanoparticles that conjugated Pt(IV) alone (CNP(Pt(IV); at 1.75 mg/kg of Pt), or with core-shell nanoparticles that conjugated Pt(IV) and electrostatically complexed Cas9 mRNA and BCL-2 sgRNA (CNP(Pt(IV);Cas9;sg1; at 1.75 mg/kg of Pt, 2.5 mg/kg of Cas9 mRNA, and 1.25 mg/kg of sg1). The body weight of each animal was monitored every other day starting with the day of injection (Day 0). At the end of the study, mice were sacrificed and blood was collected via cardiac puncture for serum chemistries and complete blood counts. The major tissues and organs from each animal were also collected, fixed with 4% formalin, and stained with H&E.

Establishment of the PDX model: C.B-17/Icr-SCID/Sed mice were purchased from Charles River and bred at MGH. They were implanted with primary cells obtained from a patient with "platinum-resistant" and advanced-stage HGSOC after lentiviral transduction of firefly luciferase (10 million cells/animal; 0.5 mL PBS; IP injection). Tumor growth was monitored by BLI.

Biodistribution study: Once the BLI radiant efficiency of their PDX tumors reached >1×10$^7$ photons/s/cm$^2$/sr, mice were grouped into cohorts with similar mean radiant efficiency values (n=3 mice per group). The animals were subsequently administered core-shell nanoparticles that were conjugated to Cy7.5 and electrostatically complexed with Cy5-labeled EGFP mRNA (CNP(Cy7.5,Pt(IV);Cy5-EGFP mRNA; at 1.75 mg/kg of Pt and 35 µg Cy5 EGFP per mice by IP injection). Whole animal fluorescence imaging was conducted by gating on Cy7.5- and Cy5-based emission signals, which were used to determine the location of the nanoparticles (Cy7.5) and mRNA species (Cy5) with respect to the tumors (BLI). To verify the in vivo stability of the core shell nanoparticles, mice were also treated with nanoparticles in which the core polymer was labeled with Cy5.5 and the shell polymer was conjugated to Cy7.5 (CNP(Cy7.5, Cy5.5,Pt(IV)). At 24 h after IP administration, the mice were injected with 225 mg/kg of d-luciferin (Promega) and anaesthetized 10 min later before BLI imaging, using the IVIS instrument (Caliper LS; auto exposition mode). Imaging was also performed after laparotomy upon animal sacrifice. The following imaging parameter were utilized: Cy5 ($\lambda_{ex}$=640 nm; $\lambda_{end-em}$=680 nm) along with Cy7.5 ($\lambda_{ex}$=745 nm; $\lambda_{end-em}$=840 nm); or Cy5.5 ($\lambda_{ex}$=640 nm; $\lambda_{end-em}$=680 nm) along with Cy7.5 ($\lambda_{ex}$=740 nm; $\lambda_{end-em}$=820 nm). For mice treated with CNP(Cy7.5,Cy5.5,Pt(IV)), computed tomography (CT) imaging was also conducted in vivo, after sacrifice, and upon organ collection. Half of each of the excised organs was subject to HNO3/H2O2 digestion followed by ICP-MS to quantify the content of Pt per mass tissue.

Pharmacodynamics study: Once the BLI radiant efficiency of their PDX tumors reached >1×10$^7$ photons/s/cm$^2$/sr, mice were administered ×2 weekly doses one of the following treatments by IP injection: PBS, cisplatin alone (Pt(II); at 1.75 mg/kg of Pt), or Pt(II) along with core-shell nanoparticles that complexed Cas9 mRNA and BCL-2 sgRNA (at 1.75 mg/kg of Pt, 2.5 mg/kg of Cas9 mRNA, and 1.25 mg/kg of sg1); additional treatment groups included core-shell nanoparticles that were conjugated to Pt(IV) alone (CNP(Pt(IV); at 1.75 mg/kg of Pt) or that were further complexed with Cas9 mRNA and BCL-2 sgRNA (CNP(Pt(IV);Cas9,sg1; at 1.75 mg/kg of Pt, 2.5 mg/kg of Cas9 mRNA, and 1.25 mg/kg of sg1). 72 h after receiving the second dose, the mice were sacrificed and their tumors were harvested. The tumors were sectioned for confocal imaging after IF staining for cleaved Caspase-3; WB was conducted for BCL-2 levels with respect to that of GAPDH (product of a house-keeping gene; control); and next-generation sequencing was performed to determine the numbers of indels within the BCL-2 gene of each treated tumor. The sequences of the primers used for PCR amplification of the BCL-2 locus were as follows—Forward: 5'-CTGGGGCGAGAGGTGCCGTTG-3'; Reverse: 5'-CTCGGCGAAGTCGCGGCGGTAGC-3'.

Tumor growth inhibition: Once the BLI radiant efficiency of their PDX tumors reached >1×10$^7$ photons/s/cm2/sr, mice were grouped into cohorts with similar mean radiant efficiency values (n=5 mice per group) and were administered ×4 weekly doses one of the following treatments by IP injection: PBS, cisplatin alone (Pt(II); at 1.75 mg/kg of Pt), or Pt(II) along with core-shell nanoparticles that complexed Cas9 mRNA and BCL-2 sgRNA (at 1.75 mg/kg of Pt, 2.5 mg/kg of Cas9 mRNA, and 1.25 mg/kg of sg1); additional treatment groups included core-shell nanoparticles that were conjugated to Pt(IV) alone (CNP(Pt(IV); at 1.75 mg/kg of Pt) or that were further complexed with Cas9 mRNA and BCL-2 sgRNA (CNP(Pt(IV);Cas9,sg1; at 1.75 mg/kg of Pt, 2.5 mg/kg of Cas9 mRNA, and 1.25 mg/kg of sg1). Mice were monitored twice per week for toxicity (i.e. weight change and by behavioral inventory); and, their tumor burden was monitored weekly by BLI using the IVIS instrument. Once animals reached the designated study endpoint (>15% loss in body-weight and/or moribund status), they were sacrificed; their tumors were collected and weighed; and, their major organs were harvested for H&E staining.

Results

Reactions of sgRNA with Various Small Molecule Anticancer Agents and their Effects on the Fidelity of CRISPR/Cas9 Mediated Gene Silencing Combination therapies have long been utilized to enhance antitumor efficacy. For in vivo delivery, it is imperative to administer all agents within a narrow temporal window in order to overcome challenges associated with fluctuations in tumor blood flow, continued tumor cell propagation, invasion and metastasis, as well as secondary mutations that may arise to inhibit therapeutic efficacy. When combining CRISPR/Cas9 and small molecule chemotherapeutics, both types of anticancer agents must further be delivered with the same tumor cell in order to take advantage of therapeutic synergies. Having established the rapidity by which platinum-based anticancer agents chemically react with siRNA to induce thermal destabilization of these double stranded (ds-)RNA macromolecules, thereby preventing effective RNAi, we first sought to determine how similar interactions with reactive small molecule chemotherapeutics could disrupt CRISPR/Cas9 function.

To model reactions that could occur in vivo, we utilized an in vitro system that consisted of the established SKOV3 ovarian cancer cell line, which was engineered to constitutively express the Cas9 protein via lentiviral transduction. SMAD4 sgRNA was subsequently incubated with various small molecule chemotherapeutics for various durations, ranging from 3 to 24 h; the sgRNA was subsequently purified, recovered by centrifugation filtration, and delivered intracellularly within these Cas9-expressing SKOV3 cells. Cell lysates for protein were isolated at 72 h after lipofectamine-based delivery of sgRNA (10 nM); and, western blot (WB) was conducted to measure relative SMAD4 levels with respect to the product of the housekeeping gene GAPDH and in comparison to cells that did not receive SMAD4 sgRNA. This experimental system allowed for facile screening of the relative activity of sgRNA after incubation with one of an extensive set of chemotherapeutic species, which included the platinum(II)-based anticancer agent cisplatin (Pt(II)), two chemically inert platinum(IV) prodrugs (Pt(IV)-OH and Pt(IV)-COOH), the topoisomerase inhibitors doxorubicin and camptothecin, the antimetabolite gemcitabine, and the DNA alyklator melphalan. By 12 h of coincubation with either Pt(II) or melphalan, SMAD4 sgRNA was unable to effectively suppress expression of SMAD4 protein (to levels<30% of baseline) within Cas9-expressing SKOV3 cells. When examining the rapidity of sgRNA deactivation in the presence of these two reactive small molecule chemotherapeutics, we found that sgRNAs that had been incubated with Pt(II) for >3 h or with melphalan for >6 h were unable to prevent protein expression from the target gene. Notably, co-incubation with either of the chemically inert platinum(IV) species (Pt(IV)-OH and Pt(IV)-COOH) or with any of the nonreactive chemotherapeutics (doxorubicin, gemcitabine, and camptothecin) for even up to 24 h prior to transfection did not alter the ability of SMAD4 sgRNA to effectively suppress expression levels.

Cisplatin (Pt(II)) is known to undergo rapid aqueous hydrolysis of its planar chloride ligands to interact with guanosine (G) and adenine (A) bases within both DNA and RNA macromolecules). As such, we next utilized MALDI/TOF MS to measure the rapidity of the reaction of free sgRNA with an excess of either Pt(II) or Pt(IV)-COOH in aqueous solution and at 37° C., using a model 20-mer consisting of the seed portion of SMAD4 sgRNA (s-SMAD4). The results confirmed that significant numbers of Pt-RNA adducts were formed as rapidly as 30 min after s-SMAD4 was incubated with Pt(II). Similarly to Pt(II), melphalan is known to lose its chloride atoms in aqueous solution to react with the same nucleobases in DNA and RNA (i.e. G and A). MALDI/TOF MS measurements of s-SMAD4 that had been incubated with excess amounts of melphalan revealed the formation of melphalan-RNA adducts as rapidly as 1 h in solution. Notably, no adducts were detected in the RNA macromolecule despite even 24 h of incubation with Pt(IV)-COOH, gemcitabine, or camptothecin and under identical conditions, verifying the unreactive nature of these species. MALDI/TOF MS spectra of s-SMAD4 that had been incubated with doxorubicin confirmed the presence of physical association multimers in non-covalent complexes with RNA; but, these complexes did not hinder Cas9-mediated recognition of SMAD4 sgRNA nor did they prevent CRISPR/Cas9 cleavage to silence expression.

The kinetics of Pt-RNA adduct formation in solution were further verified by atomic absorption spectroscopy (AAS), which confirmed that up to 6 Pt atoms could bind per RNA macromolecule when s-SMAD4 was incubated with Pt(II); the kinetics of adduct formation matched well with those that had been previously measured for the reactions of siRNA with a fixed and excess amount of Pt(II): i.e. the results revealed pseudo-first order kinetics, an apparent second-order rate constant of >10 μM-1s-1, and that >50% of the RNA was platinated when it was incubated for 1 h with >10 μM of Pt(II), which is typically employed to induce cytotoxicity of tumor cells. AAS measurements further independently confirmed that no Pt-RNA adducts were detected in solutions of s-SMAD4 that had been incubated with Pt(IV) for up to 24 h. Platinated s-SMAD4 was also exposed to RNase A followed by MALDI/TOF MS measurements of the cleavage products, which confirmed the formation of the 5'-A[$(NH_3)_2$Pt]GU-3' adduct within the native RNA macromolecule due to reaction with Pt(II); this adduct was not detected in the cleavage products of s-SMAD4 that had been incubated with Pt(IV)-COOH prior to RNase A addition.

To elucidate the mechanism(s) by which platination or alkylation of sgRNA resulted in ineffective cleavage of target genomic DNA by Cas9, we conducted a PicoGreen based assay to determine the melting temperature (Tm) of a heterodimer comprised of s-SMAD4 and its complementary single-stranded (ss-)DNA. The Tm of the unreacted 20-mer and the ss-DNA (41° C.) resembled the calculated Tm of the heterodimer of the native SMAD4 sgRNA with DNA (43° C.). Pretreatment of s-SMAD4 with Pt(IV)-COOH did not significantly alter its ability to bind ss-DNA; but, s-SMAD4 that was preincubated with Pt(II) could not heterodimerize with ss-DNA at any temperature.

Intracellular Delivery of Nanoparticles Incorporating a Platinum(IV)-Based Prodrug and RNA Components for Expression of the CRISPR/Cas9 Machinery To overcome inherent challenges in the spatial and temporal delivery of CRISPR/Cas9 components and small molecule anticancer agents to the same tumor cell, as well as to avoid deactivation of sgRNA when combined with reactive chemotherapeutics, we sought to develop an appropriate vehicle that could combine and deliver both types of agents. We synthesized a novel triblock copolymer of mPEG-b-PZLL-b-PASP(DET)) in which a lipophilic and chemically-inert platinum(IV) prodrug (Pt(IV)) could be covalently bound to free amino groups in the PASP(DET) chain of the polymer. We characterized the material properties of these nanoparticles, which could complex with Cas9 mRNA and sgRNA by varying the ratios of free amino groups of the polymer (N) to total phosphate groups of the RNA macromolecules (P) in solution (i.e. N/P ratio) (FIG. 35 and FIG. 36 and Table 4).

TABLE 4

Characterization of Different Nanoparticle Formulations Developed for the Incorporation of Cas9 mRNA, sgRNA and/or Pt(IV).

| Sample | Diameter by TEM* (nm) | Diameter by DLS** (nm) | PDI | ZP (mV) |
| --- | --- | --- | --- | --- |
| NP | 54 ± 17 | 110.1 ± 5.7 | 0.139 ± 0.02 | 41.9 ± 0.7 |
| NP(Cas9, sgRNA) | 43 ± 21 | 92.3 ± 2.0 | 0.175 ± 0.05 | 35.8 ± 0.6 |
| NP(Pt(IV)) | 62 ± 19 | 89.8 ± 1.8 | 0.177 ± 0.01 | 35.6 ± 0.3 |
| NP(Pt(IV); Cas9, sgRNA) | 67 ± 15 | 81.1 ± 1.6 | 0.18 ± 0.07 | 30.8 ± 0.8 |

*As determined by TEM measurements of at least 20 separate nanoparticles from 3 individual imaging fields.
**As determined from DLS histograms In vitro cellular viability measurements conducted on pairs of cisplatin-sensitive and resistant cells lines (A2780 and A2780 DDP), on established cell lines that possessed genetic signatures that resembled those of HGSOCs (OVCAR4, COV362, OVSAHO), and on primary cells from a patient with "platinum-resistant" HGSOC demonstrated enhanced activity of nanoparticles containing Pt(IV) (i.e. NP(Pt(IV)) as compared to free cisplatin (Pt(II)) (FIG. 37); inductively coupled plasma mass spectrometry (ICP-MS) of cell lysates confirmed substantially higher concentrations of intracellular Pt and Pt-DNA adducts from nanoparticle delivery of Pt(IV) (FIG. 38).

In the context of intracellular assembly of active CRISPR/Cas9 machinery from nanoparticles that contained Cas9 mRNA and sgRNA, several challenges had to be addressed, including endosomal escape of the mRNA species to enable effective cytoplasmic translation of Cas9 protein. To track this process in vitro, we fluorescently labeled nanoparticles through covalent conjugation of FITC to the PASP chains of the polymer; we further complexed these FITC-labeled nanoparticles with Cy5-labeled mRNA at an N/P ratio of 8; and, confocal scanning laser microscopy was performed at various time points after incubation with SKOV3 cells. These experiments confirmed uptake of nanoparticles within a punctate distribution followed by time-dependent release and redistribution of mRNA throughout the cytoplasm (FIG. 39A). Utilizing nanoparticles complexed to Cy5-labeled EGFP mRNA (NP(Cy5-EGFP mRNA,sgRNA)), we verified time-dependent translation of EGFP protein within the cytoplasm of SKOV3 cells. Flow cytometry was used to quantify the kinetics of uptake for these nanoparticles into SKOV3 (FIG. 39B) and A2780 cells, demonstrating that >93% of the cells contained Cy5-EGFP mRNA by 24 h. These experiments were also repeated after first incubating the cells with one of several small molecule inhibitors of cellular uptake (FIG. 39C); the results implicated multiple pathways but with a predominance of clatherin-dependent and -independent endocytosis.

While these experiments confirmed cellular uptake, endosomal escape, and cytoplasmic translation of mRNA after in vitro delivery, several additional challenges to in vivo administration included methods by which to protect the RNA macromolecules from environmental nucleases and mechanisms to neutralize their remaining cationic charge so as to minimize nonspecific biological binding and clearance. To address these issues, we utilized layer-by-layer assembly to coat the nanoparticles with a polymeric shell comprised of the diblock copolymer of mPEG-b-PGA. It was imperative to first verify that the coating did not prevent uptake nor intracellular release of the mRNA. As such, we generated complexes of Cy5.5-labeled Cas9 mRNA with iFluor™ 405-conjugated nanoparticles and further coated them with a 5-FAM-labeled shell polymer. These constructs enabled simultaneous but independent in vitro tracking of Cas9 mRNA (by Cy5.5; red), the core nanoparticles (by iFluor™ 405; blue) and the shell polymer (by 5-FAM; green) during confocal microscopy and flow cytometry experiments. The results of these studies confirmed that core-shell nanoparticles are taken up intact into cells, that the water-soluble shell polymers and mRNA species dissociate from the core nanoparticles intracellularly, and that the nanoparticle-complexed mRNA is able redistribute throughout the cellular cytoplasm.

In Vitro Synergistic Activity Afforded by Concurrent Delivery of a Platinum(IV) Prodrug, Cas9 mRNA, and sgRNA Against Different Gene Targets Using a fixed concentration of Cas9 mRNA (Cas9; 1 nM) and sgRNA against SMAD4 (SMAD4; 10 nM), we examined the amounts of polymeric nanoparticles (NP) that were required to promote CRISPR/Cas9-mediated gene silencing (FIG. 39D). The results confirmed that nanoparticle complexation of Cas9 mRNA/sgRNA at an N/P ratio of >8 resulted in effective in vitro cleavage and suppressed SMAD4 expression in both SKOV3 and A2780 cells (FIG. 39E). Migration assays evinced the biological effects of SMAD4 silencing in these cells, demonstrating reduced migration and invasion as compared to cells that were treated with NP alone (FIG. 39F). By employing Cas9 mRNA with several different sgRNA constructs against BCL-2 (sg1, sg2, sg3) and a negative control (NC sgRNA), we confirmed specific suppression of additional target gene products mediated by nanoparticle delivery of CRISPR/Cas9 machinery (FIG. 40A).

Nanoparticles that delivered Pt(IV), Cas9 mRNA and BCL-2 sgRNA (sg1 or sg3) conferred enhanced cytotoxicity to SKOV3 cells (FIG. 40B). Measurements of $IC_{50}$ values confirmed their augmented activity as compared to free cisplatin (Pt(II)), nanoparticle-conjugated Pt(IV) alone (NP (Pt(IV)), or combinations of free Pt(II) with nanoparticle-complexed Cas9 mRNA and BCL-2 sgRNA (e.g. Pt(II)+NP (Cas9,sg1)). Note that nanoparticles that delivered negative control sgRNA along with Cas9 mRNA and Pt(IV) did not induce cytotoxicity at levels beyond that which was seen with nanoparticle delivery of Pt(IV) alone, confirming that the synergy that was imparted between the small molecule anticancer agent and CRISPR/Cas9 was specific to silencing of BCL-2. When combining free Pt(II) with nanoparticles that contained Cas9 mRNA and BCL-2 sgRNA (i.e. Pt(II)+NP(Cas9,sg1)), co-incubation of the two species for as little as 30 min prior to cellular exposure resulted in decreased in vitro cytotoxicity as compared to free Pt(II) alone. These results support that nanoparticle complexation of the RNA macromolecules did not effectively shield them from reacting with free Pt(II), which resulted in their deactivation. They further highlighted the need to combine CRISPR/Cas9 along with an inert Pt(IV) prodrug, which afforded synergistic treatment effects when both agents were delivered into the same cell using a single nanoparticle vehicle.

SKOV3 cells that were treated with nanoparticles that combined Pt(IV), Cas9 mRNA and one of two different sgRNA (sg1 or sg3) against BCL-2 (e.g. NP(Pt(IV);Cas9, sg1)) demonstrated maximal suppression of colony formation and the highest levels of apoptosis as assessed by flow cytometry (FIGS. 40C and 40D). WB confirmed that BCL-2 suppression mediated by these nanoparticles resulted in the upregulation of cleaved PARP1 (cPARP1) and cleaved caspase 3 (c-Caspase 3), which were not evident in cells treated with free Pt(II), nanoparticle-bound platinum(IV) alone (NP(Pt(IV)), nanoparticles that only complexed Cas9 mRNA and BCL-2 sgRNA (e.g. NP(Cas9,sg1)), or their combinations. Note that analogous results were obtained with A2780 cells (data not shown), confirming that synergistic treatment effects were conferred only from intracellular delivery of Pt(IV), Cas9 mRNA, and BCL-2 sgRNA using a single nanoparticle construct.

Circumventing Platinum Resistance Through In Vivo Delivery of a Platinum(IV) Prodrug and RNA Components for CRISPR/Cas9-Mediated Silencing of BCL-2

Having validated synergistic activity in established cell lines, we next sought to determine whether combined delivery of platinum-based anticancer agents with CRISRP/Cas9 machinery aimed at silencing BCL-2 could be utilized to overcome resistance in heavily treated human tumors. For our model system, we utilized primary cells obtained from a patient with "platinum-resistant" HGSOC. In vitro delivery of nanoparticles that contained Pt(IV), Cas9 mRNA and sgRNA against BCL-2 (sg1) effectively silenced BCL-2 expression and potentiated the activity of the platinum-based agent (FIGS. 33A and 33B). A PDX model of advanced ovarian cancer was then established in C.B-17/Icr-SCID/Sed mice via IP dissemination of the primary cells after lentiviral based transfection of firefly luciferase, enabling bioluminescence imaging (BLI) to track tumor growth and metastasis; core-shell nanoparticles (CNPs) conjugated with Cy7.5 and containing Cy5-labeled mRNA confirmed co-localization of both species within peritoneal tumor implants after IP administration (FIG. 33C). CT imaging of the same mice detected high platinum (Pt) contrast within the tumors, corresponding to the nanoparticle-conjugated Pt(IV) species (FIG. 33D). Ex vivo fluorescence and CT imaging of excised organs confirmed that the nanoparticles (Cy7.5), mRNA (Cy5) and Pt(IV) (enhanced Pt contrast on CT) were distributed predominantly within the peritoneal tumor implants (FIG. 33E). Confocal microscopy of tumor sections demonstrated a predominance of mRNA-containing nanoparticles within the periphery as opposed to the core of the tumors (FIG. 33F).

To address concerns over potential toxicities imparted by nanoparticles containing Pt(IV) alone or in conjunction with Cas9 mRNA and sgRNA against BCL-2, single dose toxicity studies in immunocompetent BALB/c mice were undertaken. The mice demonstrated no changes in their daily weights over a two-week period; and, terminal blood draws for serology studies confirmed no nephrotoxicity, hepatotoxicity, nor myelosuppression from nanoparticles administered at up to 1.75 mg/kg of Pt per mouse and with or without Cas9 mRNA (2.5 mg/kg) and BCL-2 sgRNA (1.25 mg/kg). Pathologic examination of tissue sections after H&E staining showed no signs of gross toxicity or microarchitectural distortion in any organ and in every mouse (n=3 mice/group). Pharmacodynamic studies were undertaken in which various nanoparticle and control formulations were administered at this equivalent dose level of Pt and/or Cas9 mRNA/sgRNA and in two weekly IP injections into the PDX model. The mice were sacrificed at 72 h after the second injection; immunofluorescence for cleaved Caspase 3 was conducted on excised tumors; and, the results confirmed that the highest levels of cleaved Caspase 3 were found in the periphery of tumors from mice that were treated with core-shell nanoparticles containing Pt(IV), Cas9 mRNA, and BCL-2 sgRNA (i.e. CNP(Pt(IV);Cas9,sg1)) (FIG. 33G). WB of lysates from the same tumors confirmed suppression of BCL-2 levels in the periphery of the tumors (FIG. 33H); and, next-generation sequencing showed effective cleavage of the BCL-2 gene in the same tumor locations and only after nanoparticle delivery of all three components (FIG. 33I).

Finally, a preliminary therapeutic efficacy study was conducted in the PDX model in which mice were treated with PBS (negative control), free cisplatin (Pt(II)), core-shell nanoparticles containing only Pt(IV) (CNP(Pt(IV)), combinations of free cisplatin and core-shell nanoparticles complexed with Cas9 mRNA and BCL-2 sgRNA (Pt(II)+CNP (Cas9,sg1)), or core-shell nanoparticles that contained Pt(IV), Cas9 mRNA, and BCl-2 sgRNA on the same delivery vehicle (CNP(Pt(IV);Cas9,sg1)). Tumor growth was monitored by BLI; the animals received the first of four weekly injections when the radiant efficiency of their tumors reached $1 \times 10^7$ photons/s/cm$^2$/sr, which was the level that enabled accurate quantitative comparisons of luminescence signals; and, the study was concluded when animals were moribund or exhibited >15% loss in body weight. The results confirmed that core-shell nanoparticles that delivered Pt(IV), Cas9 mRNA and BCL-2 sgRNA maximally inhibited tumor growth (FIG. 33J) and significantly prolonged survival (FIG. 33K). Measurements of tumors excised upon sacrifice confirmed statistically significant reductions in tumor weights from animals that had received this treatment and as compared to all other experimental groups (FIG. 33L). Gross and pathologic examination of excised organs confirmed that these mice, nevertheless, died from complications of metastatic disease.

Example 10—Implantation of Cancer Cells into Mice (for Following Examples Unless Otherwise Indicated)

1) Implantation of luciferized (LUC+) and red fluorescent-protein (RFP+) expressing SKOV3 cells (an established human ovarian cancer cell line) into the peritoneal cavity of nude (NCr Nu/Nu) mice, establishing an orthotopic murine model of disseminated and advanced-stage human ovarian cancer: SKOV3 human ovarian cancer cells that expressed LUC and RFP were constructed as previously described (vide supra). LUC and RFP expression were assayed and confirmed using a plate reader (Infinite 200 PRO; Tecan group Ltd., Switzerland) and an IVIS Spectrum Bioluminescent and Fluorescent Imaging System (PerkinElmer; Akron, Ohio). To establish an orthotopic xenograft model of human ovarian cancer, LUC+/RFP+ SKOV3 cells (200 µl of a suspension of $10^7$ cells/mL; i.e., 2 million cells) were implanted into female athymic nude mice (NCRNU-F, Taconic Biosciences; Hudson, N.Y.) by IP injection. Tumor growth was monitored weekly by imaging bioluminescence and RFP signals emanating from the animals, using the IVIS imaging instrument. For bioluminescence measurements, luciferin (200 µl of a 15 mg/mL solution in PBS) was administered to each animal by IP injection; after 10 min, mice were imaged both for bioluminescence and RFP signals ($\lambda_{ex}$=535 nm; $\lambda_{em}$=600 nm).

2) Implantation of luciferized (LUC+) and red fluorescent-protein (RFP+) expressing OVCAR8 cells (an established human ovarian cancer cell line) into the peritoneal cavity of nude (NCr Nu/Nu) mice, establishing an orthotopic murine model of disseminated and advanced-stage human ovarian cancer: Female NCR nu/nu mice were purchased from Taconic Co. (USA). All experimental procedures involving animals were carried out in accordance with the guidelines of the animal protocol of Massachusetts Institute of Technology. For tumor implant, $8 \times 10^5$ Luc+/red fluorescent protein-expressing OVCAR 8 cells were injected into the belly region of the 5-weeks old mice.

3) Implantation of luciferized (LUC+) expressing primary human cells from a patient with "platinum-resistant", advanced-stage, and high-grade serous ovarian cancer into the peritoneal cavity of SCID (C.B-17/Icr-SCID/Sed) mice, establishing an orthotopic patient-derived xenograft (PDX) model of disseminated, advanced-stage, and "platinum-resistant" human ovarian cancer: C.B-17/Icr-SCID/Sed mice were purchased from Charles River and bred at MGH. They were implanted with primary cells obtained from a patient with "platinum-resistant" and advanced-stage HGSOC after lentiviral transduction of firefly luciferase (2-10 million cells/animal; 0.5 mL PBS; IP injection). Tumor growth was monitored by BLI.

Example 11—IP Delivery of CRISPR/Cas9 Gene Editing Tools

A diblock copolymer of PEO-b-PGA coating nanoparticles formed from a triblock copolymer of PEO-b-PZLL-b-PASP conjugated to a platinum(IV) (Pt(IV)) prodrug and electrostatically complexed to Cas9 mRNA and sgRNA (FIG. 31) were introduced via IP injection into SCID mice that had been orthotopically xenografted with platinum-resistant patient-derived ovarian cancer cells (PDX) (FIG. 32).

Confocal images of in vivo and ex vivo biodistribution data showed co-localization of nanoparticles with peritoneal tumors in ovarian cancer PDX mice after IP injection; the images are shown in FIG. 32.

The in vivo efficacy of the nanoparticles was also studied. FIG. 33 shows images and data showing improved treatment.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicant reserves the right to physically incorporate into this application any and all materials and information from any such articles, patents, patent applications, or other physical and electronic documents.

EQUIVALENTS

The inventions have been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The inventions are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of embodiments of the invention. Further, each of the narrower species and subgeneric groupings falling within the generic disclosure also form parts of the inventions. This includes the generic description of embodiments of the invention with a proviso or negative limitation removing any subject matter from the genus, regardless of whether or not the excised material is specifically recited herein.

We claim:

1. A composition comprising:
   an agent, wherein the agent is (a) a nuclease selected from the group consisting of Cas9, TALEN, and zinc finger, or (b) a nucleic acid encoding a nuclease selected from the group consisting of Cas9, TALEN, and zinc finger;
   an optional pharmaceutically acceptable carrier;
   an optional DNA editing template; and
   a block copolymer comprising:
   (i) a first block comprising a plurality of first monomers, wherein each first monomer is hydrophilic;
   (ii) a second block comprising a plurality of second monomers, wherein each second monomer has the structure of Formula II:

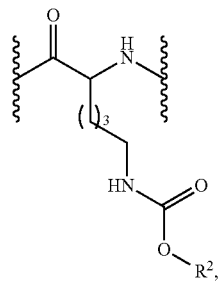

Formula II wherein $R^2$ is $C_1$-$C_6$alkyl, $C_3$-$C_6$alkenyl, $C_5$-$C_{22}$carbocyclyl-substituted $C_1$-$C_6$alkyl, or 5-22-membered heterocyclyl-substituted $C_1$-$C_6$alkyl; and
   (iii) a third block comprising a plurality of third monomers, wherein each third monomer is positively charged at a pH from about 6.8 to about 7.4,
   wherein
   the agent is non-covalently associated with the block copolymer; and
   the DNA editing template, when present, is non-covalently associated with the block copolymer.

2. The composition of claim 1, wherein the agent is Cas9 or a nucleic acid encoding Cas9; and a guide nucleic acid non-covalently associated with the block copolymer.

3. The composition of claim 1, wherein each third monomer comprises a -NHR$_2^+$ functionality at pH about 7, wherein R is H or $C_1$-$C_6$ alkyl.

4. The composition of claim 1, wherein each third monomer is selected from the group consisting of lysine, arginine, asparagine, side-chain aminoalkyl-functionalized asparagine, aspartamide, side-chain aminoalkyl-functionalized aspartamide, and ethyleneimine.

5. The composition of claim 1, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin.

6. The composition of claim 1, wherein each first monomer is ethylene glycol.

7. The composition of claim 1, wherein each third monomer has the structure of Formula III or Formula IV:

Formula III

Formula IV wherein

L³ is a bond or —C(=O)—;
p is 1, 2, or 3;
R is H or $C_1$-$C_6$alkyl; and
n is 1, 2, 3, 4, 5, or 6.

8. The composition of claim 1, wherein the block copolymer has the following structure:

A¹-(first block)-L¹-(second block)-L²-(third block)-A² wherein

A¹ is OH or -O-($C_1$-$C_6$)alkyl;
A² is H, an amine protecting group, or an amino acid;
L¹ is a covalent bond or a first linker; and
L² is a covalent bond or a second linker.

9. The composition of claim 8, wherein L¹ is —$C_1$-$C_6$alkylene-NR-; and R is H or $C_1$-$C_6$alkyl.

10. The composition of claim 1, wherein the nucleic acid encoding the Cas9 is a Cas9 mRNA and the composition further comprises a guide RNA which is non-covalently associated with the block copolymer.

11. The composition of claim 1, wherein the composition further comprises a DNA repair template non-covalently associated with the block copolymer.

12. The composition of claim 1, wherein the composition further comprises a second block copolymer non-covalently associated with the block copolymer, wherein the second block copolymer is a diblock copolymer.

13. The composition of claim 12, wherein the second block copolymer comprises a fourth block comprising a plurality of fourth monomers, and a fifth block comprising a plurality of first monomers.

14. The composition of claim 13, wherein at least one fourth monomer comprises a —$CO_2$ functionality at pH about 7.

15. The composition of claim 13, wherein each fourth monomer is selected from the group consisting of aspartic acid, glutamic acid, glycolic acid, acrylic acid, and methacrylic acid.

16. The composition of claim 1, wherein the composition further comprises an anticancer agent.

17. The composition of claim 16, wherein the anticancer agent is covalently bound to the block copolymer.

18. The composition of claim 17, wherein the anticancer agent is an alkylating agent or a nucleic acid cross-linking agent.

19. The composition of claim 17, wherein the anticancer agent comprises Pt(II) or Pt(IV).

20. The composition of claim 17, wherein the anticancer agent is covalently bound to at least one third monomer.

21. The composition of claim 17, wherein at least one third monomer has the structure of Formula I:

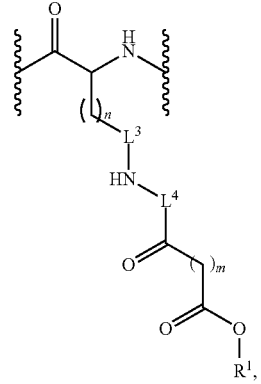

Formula I wherein

R¹ comprises the anticancer agent;
L³ is a bond or —C(=O)—;
L⁴ is a bond or [—($C_1$-$C_6$)alkylene-NR-]$_p$;
p is 1, 2, or 3;
R is H or $C_1$-$C_6$alkyl;
n is 1, 2, 3, 4, 5, or 6; and
m is 1, 2, 3, 4, 5, or 6.

22. The composition of claim 21, wherein the anticancer agent comprises Pt(II) or Pt(IV).

23. The composition of claim 21, wherein R¹ is

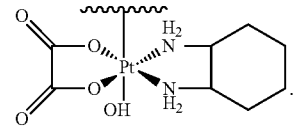

24. The composition of claim 16, wherein the anticancer agent is non-covalently associated with the block copolymer.

25. The composition of claim 24, wherein the anticancer agent is an alkylating agent or a nucleic acid cross-linking agent.

26. The composition of claim 24, wherein the anticancer agent comprises Pt(II) or Pt(IV).

27. The composition of claim 1, wherein the block copolymer does not comprise polyhistidine.

28. A method of treating cancer comprising administering to a subject in need thereof a therapeutically effective amount of a composition of claim 1.

* * * * *